US011826569B2

(12) United States Patent
Mishra et al.

(10) Patent No.: US 11,826,569 B2
(45) Date of Patent: Nov. 28, 2023

(54) APPARATUS WITH SEQUENTIALLY IMPLANTED STIMULATORS

(71) Applicant: Nalu Medical, Inc., Carlsbad, CA (US)

(72) Inventors: Lakshmi Narayan Mishra, Carlsbad, CA (US); Andre Castillo, Encinitas, CA (US); Lee Fason Hartley, Carlsbad, CA (US); Christopher Linden, Vista, CA (US); Joseph Christopher Flaherty, Auburndale, FL (US)

(73) Assignee: Nalu Medical, Inc., Carlsbad, CA (US)

( * ) Notice: Subject to any disclaimer, the term of this patent is extended or adjusted under 35 U.S.C. 154(b) by 55 days.

(21) Appl. No.: 17/487,535

(22) Filed: Sep. 28, 2021

(65) Prior Publication Data
US 2022/0218994 A1    Jul. 14, 2022

Related U.S. Application Data

(63) Continuation of application No. 16/539,977, filed on Aug. 13, 2019, now Pat. No. 11,160,980, which is a
(Continued)

(51) Int. Cl.
*A61N 1/36* (2006.01)
*A61N 1/378* (2006.01)

(52) U.S. Cl.
CPC ..... *A61N 1/36071* (2013.01); *A61N 1/36125* (2013.01); *A61N 1/3787* (2013.01)

(58) Field of Classification Search
CPC ............... A61N 1/3787; A61N 1/0551; A61N 1/37223; A61N 1/37229; A61N 1/3756;
(Continued)

(56) References Cited

U.S. PATENT DOCUMENTS

| 3,902,501 A | 9/1975 | Citron et al. |
| 3,939,843 A | 2/1976 | Smyth et al. |

(Continued)

FOREIGN PATENT DOCUMENTS

| EP | 2155330 B1 | 10/2014 |
| WO | WO-2005105201 A2 | 11/2005 |

(Continued)

OTHER PUBLICATIONS

Buhlmann, J. et al., "Modeling of a segmented electrode for desynchronizing deep brain stimulation" Frontiers in Neuroengineering (2011) vol. 4, Article 15, pp. 1-8.
(Continued)

*Primary Examiner* — Carl H Layno
*Assistant Examiner* — Anh-Khoa N Dinh
(74) *Attorney, Agent, or Firm* — Cooley LLP

(57) ABSTRACT

A stimulation apparatus for a patient may include an external system configured to transmit transmission signals and an implantable system configured to receive the transmission signals from the external system. The implantable system may include at least one implantable lead, a first implantable device for connecting to the implantable lead during a first time period, and a second implantable device for subsequently connecting to the implantable lead for a second time period.

44 Claims, 19 Drawing Sheets

Related U.S. Application Data continuation of application No. PCT/US2018/019522, filed on Feb. 23, 2018.

(60) Provisional application No. 62/463,328, filed on Feb. 24, 2017.

(58) Field of Classification Search
CPC ............ A61N 1/36071; A61N 1/36125; A61N 1/3752; A61N 1/0558; A61N 1/36062; A61N 1/36185; A61N 1/37247; A61N 1/37252; A61N 1/37518; A61N 1/05; A61N 1/0553; A61N 1/37205; A61N 1/16; G16H 40/40; G16H 40/63; G16H 20/30; G16H 20/40; G16H 40/67; G16H 50/50; G16Z 99/00; A61M 2025/0007; A61M 2025/0057; A61M 25/0026; A61M 25/0043; A61M 25/007; A61M 5/14
See application file for complete search history.

(56) References Cited

U.S. PATENT DOCUMENTS

| | | |
|---|---|---|
| 4,033,357 A | 7/1977 | Helland et al. |
| 4,236,529 A | 12/1980 | Little |
| 4,262,678 A | 4/1981 | Stokes |
| 4,269,198 A | 5/1981 | Stokes |
| 4,301,815 A | 11/1981 | Doring |
| 4,407,303 A | 10/1983 | Akerstroem |
| 4,409,994 A | 10/1983 | Doring |
| 4,469,104 A | 9/1984 | Peers-Trevarton |
| 4,506,679 A | 3/1985 | Mann |
| 4,578,598 A | 3/1986 | Faulhaber |
| 4,582,069 A | 4/1986 | McArthur |
| 4,592,356 A | 6/1986 | Gutierrez |
| 4,658,835 A | 4/1987 | Pohndorf |
| 4,716,888 A | 1/1988 | Wesner |
| 4,721,118 A | 1/1988 | Harris |
| 4,796,643 A | 1/1989 | Nakazawa et al. |
| 4,841,971 A | 6/1989 | Hess |
| 4,883,070 A | 11/1989 | Hanson |
| 4,898,173 A | 2/1990 | Daglow et al. |
| 4,945,922 A | 8/1990 | Van |
| 4,957,118 A | 9/1990 | Erlebacher |
| 5,031,618 A | 7/1991 | Mullett |
| 5,143,067 A | 9/1992 | Rise et al. |
| 5,193,539 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,545,206 A | 8/1996 | Carson |
| 5,662,697 A | 9/1997 | Li et al. |
| 5,735,887 A | 4/1998 | Barreras, Sr. et al. |
| 5,807,397 A | 9/1998 | Barreras |
| 5,868,741 A | 2/1999 | Chia et al. |
| 5,908,433 A | 6/1999 | Eager et al. |
| 5,957,965 A | 9/1999 | Moumane et al. |
| 6,141,591 A | 10/2000 | Weber et al. |
| 6,169,925 B1 | 1/2001 | Villaseca et al. |
| 6,482,152 B2 | 11/2002 | Kim |
| 6,510,347 B2 | 1/2003 | Borkan |
| 6,516,227 B1 | 2/2003 | Meadows et al. |
| 6,522,926 B1 | 2/2003 | Kieval et al. |
| 6,561,975 B1 | 5/2003 | Pool et al. |
| 6,884,122 B2 | 4/2005 | Robinson et al. |
| 6,895,280 B2 | 5/2005 | Meadows et al. |
| 6,909,917 B2 | 6/2005 | Woods et al. |
| 6,950,706 B2 | 9/2005 | Rodriguez et al. |
| 6,999,819 B2 | 2/2006 | Swoyer et al. |
| 7,092,763 B1 | 8/2006 | Griffith et al. |
| 7,096,070 B1 | 8/2006 | Jenkins et al. |
| 7,239,921 B2 | 7/2007 | Canfield et al. |
| 7,616,990 B2 | 11/2009 | Chavan et al. |
| 7,711,419 B2 | 5/2010 | Armstrong et al. |
| 7,717,848 B2 | 5/2010 | Heruth et al. |
| 7,734,340 B2 | 6/2010 | De |
| 7,734,354 B1 | 6/2010 | Cox |
| 7,742,818 B2 | 6/2010 | Dinsmoor et al. |
| 7,801,615 B2 | 9/2010 | Meadows et al. |
| 7,899,550 B1 | 3/2011 | Doan et al. |
| 7,912,555 B2 | 3/2011 | Swoyer et al. |
| 7,991,479 B2 | 8/2011 | Phillips et al. |
| 8,000,805 B2 | 8/2011 | Swoyer et al. |
| 8,036,756 B2 | 10/2011 | Swoyer et al. |
| 8,086,317 B2 | 12/2011 | Finch et al. |
| 8,170,675 B2 | 5/2012 | Alataris et al. |
| 8,224,453 B2 | 7/2012 | De |
| 8,359,102 B2 | 1/2013 | Alataris et al. |
| 8,364,273 B2 | 1/2013 | De |
| 8,369,959 B2 | 2/2013 | Meskens |
| 8,401,655 B2 | 3/2013 | De |
| 8,423,147 B2 | 4/2013 | Alataris et al. |
| 8,433,415 B2 | 4/2013 | Leiter et al. |
| 8,437,853 B2 | 5/2013 | Inman et al. |
| 8,452,421 B2 | 5/2013 | Thenuwara et al. |
| 8,469,971 B2 | 6/2013 | Barker |
| 8,504,138 B1 | 8/2013 | Pivonka et al. |
| 8,538,523 B2 | 9/2013 | Sommer et al. |
| 8,538,541 B2 | 9/2013 | Milojevic et al. |
| 8,620,435 B2 | 12/2013 | Rooney et al. |
| 8,626,314 B2 | 1/2014 | Swoyer et al. |
| 8,634,928 B1 | 1/2014 | O'Driscoll et al. |
| 8,649,842 B2 | 2/2014 | Atalar et al. |
| 8,655,451 B2 | 2/2014 | Klosterman et al. |
| 8,706,240 B2 | 4/2014 | Bradley et al. |
| 8,712,533 B2 | 4/2014 | Alataris et al. |
| 8,718,781 B2 | 5/2014 | Alataris et al. |
| 8,768,472 B2 | 7/2014 | Fang et al. |
| 8,774,927 B2 | 7/2014 | Deridder |
| 8,792,988 B2 | 7/2014 | Alataris et al. |
| 8,798,773 B2 | 8/2014 | Mashiach |
| 8,868,192 B2 | 10/2014 | Alataris et al. |
| 8,874,217 B2 | 10/2014 | Alataris et al. |
| 8,874,222 B2 | 10/2014 | Alataris et al. |
| 8,880,177 B2 | 11/2014 | Alataris et al. |
| 8,880,191 B2 | 11/2014 | Pyles et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,897,870 B2 | 11/2014 | De |
| 8,903,502 B2 | 12/2014 | Perryman et al. |
| 8,934,981 B2 | 1/2015 | De |
| 8,954,165 B2 | 2/2015 | Sharma et al. |
| 8,972,502 B2 | 3/2015 | Beslic et al. |
| 9,031,664 B2 | 5/2015 | Trier |
| 9,044,612 B2 | 6/2015 | Mashiach et al. |
| 9,061,151 B2 | 6/2015 | Mashiach et al. |
| 9,144,681 B2 | 9/2015 | Decre et al. |
| 9,220,897 B2 | 12/2015 | Perryman et al. |
| 9,254,393 B2 | 2/2016 | Perryman et al. |
| 9,327,125 B2 | 5/2016 | Alataris et al. |
| 9,327,126 B2 | 5/2016 | Alataris et al. |
| 9,327,127 B2 | 5/2016 | Alataris et al. |
| 9,333,357 B2 | 5/2016 | Alataris et al. |
| 9,333,358 B2 | 5/2016 | Alataris et al. |
| 9,403,020 B2 | 8/2016 | Wingeier |
| 9,433,750 B2 | 9/2016 | Pivonka et al. |
| 9,452,288 B2 | 9/2016 | Whitehurst et al. |
| 9,462,398 B2 | 10/2016 | Deridder |
| 9,463,318 B2 | 10/2016 | Mashiach et al. |
| 9,480,842 B2 | 11/2016 | Alataris et al. |
| 9,555,248 B2 | 1/2017 | De |
| 9,555,257 B2 | 1/2017 | Mashiach et al. |
| 9,585,642 B2 | 3/2017 | Dinsmoor et al. |
| 9,623,245 B2 | 4/2017 | King et al. |
| 9,623,253 B2 | 4/2017 | Perryman et al. |
| 9,643,010 B2 | 5/2017 | Ranu |
| 9,656,077 B2 | 5/2017 | De |
| 9,656,085 B2 | 5/2017 | Moffitt et al. |
| 9,656,089 B2 | 5/2017 | Yip et al. |
| 9,707,406 B1 | 7/2017 | Dellamano et al. |
| 9,717,921 B2 | 8/2017 | Perryman et al. |
| 9,731,140 B1 | 8/2017 | Perryman et al. |
| 9,764,135 B2 | 9/2017 | De |

(56) References Cited

U.S. PATENT DOCUMENTS

| | | |
|---|---|---|
| 9,770,592 B2 | 9/2017 | Lin et al. |
| 9,789,314 B2 | 10/2017 | Perryman et al. |
| 9,789,321 B2 | 10/2017 | Dixit et al. |
| 9,826,963 B2 | 11/2017 | Scott et al. |
| 9,833,629 B2 | 12/2017 | Dellamano et al. |
| 9,913,975 B2 | 3/2018 | Carbunaru et al. |
| 9,993,646 B2 | 6/2018 | Parramon et al. |
| 10,004,635 B2 | 6/2018 | Kahook |
| 10,016,603 B2 | 7/2018 | Sachs et al. |
| 10,016,608 B2 | 7/2018 | Peterson et al. |
| 10,016,615 B2 | 7/2018 | Simon et al. |
| 10,016,627 B2 | 7/2018 | Viitala et al. |
| 10,022,549 B2 | 7/2018 | Dellamano et al. |
| 10,022,552 B2 | 7/2018 | Stahler et al. |
| 10,035,017 B2 | 7/2018 | Thakkar et al. |
| 10,035,020 B2 | 7/2018 | Wang et al. |
| 10,052,481 B2 | 8/2018 | Mcclure et al. |
| 10,076,668 B2 | 9/2018 | De |
| 10,086,201 B2 | 10/2018 | Chang et al. |
| 10,092,758 B2 | 10/2018 | De |
| 10,149,976 B1 | 12/2018 | Andresen et al. |
| 10,238,872 B2 | 3/2019 | Pivonka et al. |
| 10,238,874 B2 | 3/2019 | Perryman et al. |
| 10,245,436 B2 | 4/2019 | Perryman et al. |
| 10,272,239 B1 | 4/2019 | Andresen et al. |
| 10,315,039 B2 | 6/2019 | Perryman et al. |
| 10,320,232 B2 | 6/2019 | Pivonka et al. |
| 10,328,265 B2 | 6/2019 | Moffitt et al. |
| 10,335,596 B2 | 7/2019 | Yakovlev et al. |
| 10,411,760 B2 | 9/2019 | Yakovlev et al. |
| 10,420,947 B2 | 9/2019 | Perryman et al. |
| 10,471,262 B2 | 11/2019 | Perryman et al. |
| 10,644,539 B2 | 5/2020 | Pivonka et al. |
| 10,849,643 B2 | 12/2020 | Castillo et al. |
| 10,898,719 B2 | 1/2021 | Pivonka et al. |
| 10,967,183 B2 | 4/2021 | Yakovlev et al. |
| 11,018,721 B2 | 5/2021 | Yakovlev et al. |
| 11,090,491 B2 | 8/2021 | Mishra et al. |
| 11,097,096 B2 | 8/2021 | Linden et al. |
| 11,133,709 B2 | 9/2021 | Pivonka et al. |
| 11,160,980 B2 | 11/2021 | Mishra et al. |
| 11,318,315 B2 | 5/2022 | Hartley et al. |
| 11,331,493 B2 | 5/2022 | Pivonka et al. |
| 11,451,265 B2 | 9/2022 | Yakovlev et al. |
| 11,511,121 B2 | 11/2022 | Sit et al. |
| 11,633,151 B2 | 4/2023 | Pivonka et al. |
| 2002/0014039 A1 | 2/2002 | Merlet |
| 2002/0140399 A1 | 10/2002 | Echarri et al. |
| 2003/0055406 A1 | 3/2003 | Lebel et al. |
| 2003/0135253 A1 | 7/2003 | Kokones et al. |
| 2004/0059392 A1 | 3/2004 | Parramon et al. |
| 2004/0106954 A1 | 6/2004 | Whitehurst et al. |
| 2004/0215287 A1 | 10/2004 | Swoyer et al. |
| 2005/0043765 A1 | 2/2005 | Williams et al. |
| 2005/0222656 A1 | 10/2005 | Wahlstrand et al. |
| 2005/0245989 A1 | 11/2005 | Davis |
| 2005/0278000 A1 | 12/2005 | Strother et al. |
| 2005/0288596 A1 | 12/2005 | Eigler et al. |
| 2006/0004429 A1 | 1/2006 | Mrva et al. |
| 2006/0074450 A1 | 4/2006 | Boveja et al. |
| 2006/0074458 A1 | 4/2006 | Imran |
| 2006/0095078 A1 | 5/2006 | Tronnes |
| 2006/0122653 A1 | 6/2006 | Bradley et al. |
| 2006/0149330 A1 | 7/2006 | Mann et al. |
| 2006/0224225 A1 | 10/2006 | Ransbury et al. |
| 2007/0049986 A1 | 3/2007 | Imran |
| 2007/0049989 A1 | 3/2007 | Rossing et al. |
| 2007/0142874 A1 | 6/2007 | John |
| 2007/0270928 A1 | 11/2007 | Erlebacher |
| 2007/0288076 A1 | 12/2007 | Bulkes et al. |
| 2008/0103569 A1 | 5/2008 | Gerber |
| 2008/0103570 A1 | 5/2008 | Gerber |
| 2008/0103578 A1 | 5/2008 | Gerber |
| 2008/0132981 A1 | 6/2008 | Gerber |
| 2008/0146871 A1 | 6/2008 | Arneson et al. |
| 2008/0161803 A1 | 7/2008 | Oral et al. |
| 2008/0215110 A1 | 9/2008 | Gunderson |
| 2008/0269591 A1 | 10/2008 | Halperin et al. |
| 2008/0300654 A1 | 12/2008 | Lambert et al. |
| 2008/0300660 A1 | 12/2008 | John |
| 2009/0088817 A1 | 4/2009 | Starkebaum et al. |
| 2009/0088819 A1 | 4/2009 | Starkebaum et al. |
| 2009/0112282 A1 | 4/2009 | Kast et al. |
| 2009/0171408 A1 | 7/2009 | Solem |
| 2009/0187230 A1 | 7/2009 | Dilorenzo |
| 2009/0204170 A1 | 8/2009 | Hastings et al. |
| 2009/0216296 A1 | 8/2009 | Meskens |
| 2009/0275956 A1 | 11/2009 | Burnes et al. |
| 2009/0281597 A1 | 11/2009 | Parramon et al. |
| 2009/0319005 A1 | 12/2009 | Lineaweaver |
| 2010/0036454 A1 | 2/2010 | Bennett et al. |
| 2010/0082087 A1 | 4/2010 | Silipo et al. |
| 2010/0114189 A1 | 5/2010 | Donofrio et al. |
| 2010/0125312 A1 | 5/2010 | Stevenson et al. |
| 2010/0161002 A1 | 6/2010 | Aghassian et al. |
| 2010/0168817 A1 | 7/2010 | Yamamoto et al. |
| 2010/0249888 A1 | 9/2010 | Glenn et al. |
| 2010/0274314 A1 | 10/2010 | Alataris et al. |
| 2010/0274316 A1 | 10/2010 | Alataris et al. |
| 2010/0274318 A1 | 10/2010 | Walker et al. |
| 2011/0034886 A1 | 2/2011 | Elbe et al. |
| 2011/0054583 A1 | 3/2011 | Litt et al. |
| 2011/0093032 A1 | 4/2011 | Boggs, II et al. |
| 2011/0106214 A1* | 5/2011 | Carbunaru ......... A61N 1/36125 607/66 |
| 2011/0172737 A1 | 7/2011 | Davis et al. |
| 2011/0184337 A1 | 7/2011 | Evans et al. |
| 2011/0184488 A1 | 7/2011 | De |
| 2011/0218593 A1 | 9/2011 | Rubinstein et al. |
| 2011/0257707 A1* | 10/2011 | Kothandaraman .. A61N 1/0551 607/60 |
| 2011/0264163 A1 | 10/2011 | Tracey et al. |
| 2011/0301670 A1 | 12/2011 | Gross et al. |
| 2011/0301687 A1 | 12/2011 | Van |
| 2011/0307032 A1 | 12/2011 | Goetz et al. |
| 2012/0004708 A1 | 1/2012 | Chen et al. |
| 2012/0012630 A1 | 1/2012 | Lui et al. |
| 2012/0041508 A1 | 2/2012 | Rousso et al. |
| 2012/0197352 A1 | 8/2012 | Carbunaru et al. |
| 2012/0221074 A1 | 8/2012 | Funderburk et al. |
| 2012/0283800 A1 | 11/2012 | Perryman et al. |
| 2012/0296329 A1 | 11/2012 | Ng |
| 2012/0296444 A1 | 11/2012 | Greenberg et al. |
| 2013/0004925 A1* | 1/2013 | Labbe ................ A61N 1/36128 434/262 |
| 2013/0012866 A1 | 1/2013 | Deem et al. |
| 2013/0023943 A1 | 1/2013 | Parramon et al. |
| 2013/0053767 A1 | 2/2013 | Pivonka |
| 2013/0073007 A1 | 3/2013 | Parker et al. |
| 2013/0096650 A1 | 4/2013 | Aghassian |
| 2013/0150925 A1 | 6/2013 | Vamos et al. |
| 2013/0197609 A1 | 8/2013 | Moore et al. |
| 2013/0204321 A1 | 8/2013 | Alataris et al. |
| 2013/0215979 A1 | 8/2013 | Yakovlev et al. |
| 2013/0310706 A1 | 11/2013 | Stone et al. |
| 2013/0310901 A1 | 11/2013 | Perryman et al. |
| 2013/0317564 A1 | 11/2013 | Lin et al. |
| 2013/0331638 A1 | 12/2013 | Cameron et al. |
| 2013/0345202 A1 | 12/2013 | Amselem |
| 2014/0025140 A1 | 1/2014 | Lui et al. |
| 2014/0046402 A1 | 2/2014 | Saoji |
| 2014/0046413 A1 | 2/2014 | Kane et al. |
| 2014/0094876 A1 | 4/2014 | Wingeier et al. |
| 2014/0100636 A1 | 4/2014 | Mashiach et al. |
| 2014/0107709 A1 | 4/2014 | Schmitz et al. |
| 2014/0142507 A1 | 5/2014 | Armes |
| 2014/0163580 A1 | 6/2014 | Tischendorf et al. |
| 2014/0163638 A1 | 6/2014 | Marnfeldt et al. |
| 2014/0163646 A1 | 6/2014 | Tischendorf et al. |
| 2014/0172047 A1 | 6/2014 | Spitaels et al. |
| 2014/0222106 A1 | 8/2014 | Sharma et al. |
| 2014/0275847 A1 | 9/2014 | Perryman et al. |
| 2014/0277282 A1 | 9/2014 | Jaax |
| 2014/0288393 A1 | 9/2014 | Grevious et al. |

(56) References Cited

U.S. PATENT DOCUMENTS

| | | |
|---|---|---|
| 2014/0288616 A1 | 9/2014 | Rawat et al. |
| 2014/0304773 A1 | 10/2014 | Woods et al. |
| 2014/0336727 A1 | 11/2014 | Perryman et al. |
| 2014/0346078 A1 | 11/2014 | Chang |
| 2014/0371515 A1 | 12/2014 | John |
| 2015/0018728 A1 | 1/2015 | Gross et al. |
| 2015/0035378 A1 | 2/2015 | Calhoun et al. |
| 2015/0080982 A1 | 3/2015 | Van Funderburk |
| 2015/0100110 A1 | 4/2015 | Towe et al. |
| 2015/0119673 A1 | 4/2015 | Pellinen et al. |
| 2015/0164401 A1 | 6/2015 | Toth et al. |
| 2015/0224326 A1 | 8/2015 | Toth et al. |
| 2015/0321000 A1 | 11/2015 | Rosenbluth et al. |
| 2015/0321002 A1 | 11/2015 | Khalil et al. |
| 2015/0335285 A1 | 11/2015 | Poon et al. |
| 2016/0023022 A1 | 1/2016 | Zarins et al. |
| 2016/0030666 A1 | 2/2016 | Lozano et al. |
| 2016/0106994 A1 | 4/2016 | Crosby et al. |
| 2016/0113671 A1 | 4/2016 | Berger |
| 2016/0121102 A1 | 5/2016 | Tockman et al. |
| 2016/0135917 A1 | 5/2016 | Mickle et al. |
| 2016/0136438 A1 | 5/2016 | Perryman et al. |
| 2016/0136443 A1 | 5/2016 | Grandhe et al. |
| 2016/0144184 A1 | 5/2016 | Marnfeldt |
| 2016/0166835 A1 | 6/2016 | De Ridder |
| 2016/0199658 A1 | 7/2016 | Nassif et al. |
| 2016/0218433 A1 | 7/2016 | Nghiem et al. |
| 2016/0331956 A1 | 11/2016 | Yakovlev et al. |
| 2016/0346546 A1 | 12/2016 | Zhu |
| 2016/0375237 A1 | 12/2016 | Hahn et al. |
| 2017/0001003 A1 | 1/2017 | Pivonka et al. |
| 2017/0028199 A1 | 2/2017 | Roehrlein et al. |
| 2017/0050021 A1 | 2/2017 | Cosman, Sr. |
| 2017/0054324 A1 | 2/2017 | Pivonka et al. |
| 2017/0054332 A1 | 2/2017 | Pivonka et al. |
| 2017/0087353 A1 | 3/2017 | Thota et al. |
| 2017/0095667 A1 | 4/2017 | Yakovlev et al. |
| 2017/0165491 A9 | 6/2017 | De |
| 2017/0189683 A1 | 7/2017 | Perryman et al. |
| 2017/0197082 A1 | 7/2017 | Pang et al. |
| 2017/0216602 A1 | 8/2017 | Waataja et al. |
| 2017/0252552 A1 | 9/2017 | Cook et al. |
| 2017/0368339 A1 | 12/2017 | De Ridder |
| 2018/0028824 A1 | 2/2018 | Pivonka et al. |
| 2018/0056080 A1 | 3/2018 | Reinke et al. |
| 2018/0064944 A1 | 3/2018 | Grill et al. |
| 2018/0071512 A1 | 3/2018 | Feldman et al. |
| 2018/0071536 A1 | 3/2018 | Skelton et al. |
| 2018/0083668 A1 | 3/2018 | Yakovlev et al. |
| 2018/0085593 A1 | 3/2018 | Fayram et al. |
| 2018/0169423 A1 | 6/2018 | Perryman et al. |
| 2018/0236237 A1 | 8/2018 | Kent et al. |
| 2018/0243563 A1 | 8/2018 | Vallejo et al. |
| 2018/0256906 A1 | 9/2018 | Pivonka et al. |
| 2018/0296834 A1 | 10/2018 | John et al. |
| 2018/0326220 A1 | 11/2018 | Kaula et al. |
| 2018/0333578 A1 | 11/2018 | Mock et al. |
| 2018/0368875 A1 | 12/2018 | Castillo et al. |
| 2019/0001139 A1 | 1/2019 | Mishra et al. |
| 2019/0008556 A1 | 1/2019 | Perryman et al. |
| 2019/0009097 A1 | 1/2019 | Hartley et al. |
| 2019/0143124 A1 | 5/2019 | Perryman et al. |
| 2019/0151659 A1 | 5/2019 | Mishra et al. |
| 2019/0247198 A1 | 8/2019 | Zellmer et al. |
| 2019/0262610 A1 | 8/2019 | Kent et al. |
| 2019/0269913 A1 | 9/2019 | Pivonka et al. |
| 2019/0374776 A1 | 12/2019 | Mishra et al. |
| 2020/0101291 A1 | 4/2020 | Yakovlev et al. |
| 2020/0108253 A1 | 4/2020 | Crowder et al. |
| 2020/0129108 A1 | 4/2020 | Parker et al. |
| 2020/0139138 A1 | 5/2020 | Sit et al. |
| 2020/0171313 A1 | 6/2020 | Dinsmoor et al. |
| 2020/0204209 A1 | 6/2020 | Yakovlev et al. |
| 2020/0222000 A1 | 7/2020 | Poon et al. |
| 2020/0306528 A1 | 10/2020 | Linden et al. |
| 2020/0398058 A1 | 12/2020 | Pivonka et al. |
| 2021/0099015 A1 | 4/2021 | Pivonka et al. |
| 2021/0196957 A1 | 7/2021 | Yakovlev et al. |
| 2021/0330981 A1 | 10/2021 | Mishra et al. |
| 2021/0399765 A1 | 12/2021 | Yakovlev et al. |
| 2022/0016103 A1 | 1/2022 | Baltcheva et al. |
| 2022/0016430 A1 | 1/2022 | Hartley et al. |
| 2022/0072300 A1 | 3/2022 | Yakovlev et al. |
| 2022/0080189 A1 | 3/2022 | Mishra et al. |
| 2022/0118251 A1 | 4/2022 | Buddha et al. |
| 2022/0134108 A1 | 5/2022 | Dinsmoor et al. |
| 2022/0176108 A1 | 6/2022 | Linden et al. |
| 2022/0176120 A1 | 6/2022 | Kulkarni et al. |
| 2022/0176133 A1 | 6/2022 | Buddha et al. |
| 2022/0263346 A1 | 8/2022 | Pivonka et al. |
| 2023/0029600 A1 | 2/2023 | Pivonka et al. |
| 2023/0129373 A1 | 4/2023 | Sit et al. |

FOREIGN PATENT DOCUMENTS

| | | |
|---|---|---|
| WO | WO-2007051146 A1 | 5/2007 |
| WO | WO-2007068284 A1 | 6/2007 |
| WO | WO-2008066556 A1 | 6/2008 |
| WO | WO-2009045297 A1 | 4/2009 |
| WO | WO-2010062517 A1 | 6/2010 |
| WO | WO-2013035092 A2 | 3/2013 |
| WO | WO-2014071079 A1 | 5/2014 |
| WO | WO-2014089299 A2 | 6/2014 |
| WO | WO-2014153124 A1 | 9/2014 |
| WO | WO-2014153219 A1 | 9/2014 |
| WO | WO-2014153228 A1 | 9/2014 |
| WO | WO-2014205129 A1 | 12/2014 |
| WO | WO-2015139053 A1 | 9/2015 |
| WO | WO-2015179177 A1 | 11/2015 |
| WO | WO-2015196164 A2 | 12/2015 |
| WO | WO-2015196164 A3 | 2/2016 |
| WO | WO-2016028608 A1 | 2/2016 |
| WO | WO-2016113832 A1 | 7/2016 |
| WO | WO-2016127130 A1 | 8/2016 |
| WO | WO-2016191055 A1 | 12/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018023057 A1 | 2/2018 |
| WO | WO-2018126062 A1 | 7/2018 |
| WO | WO-2018144631 A1 | 8/2018 |
| WO | WO-2018156953 A1 | 8/2018 |
| WO | WO-2018208992 A1 | 11/2018 |
| WO | WO-2021003439 A1 | 1/2021 |
| WO | WO-2021067873 A1 | 4/2021 |
| WO | WO-2021133947 A1 | 7/2021 |
| WO | WO-2021262762 A1 | 12/2021 |
| WO | WO-2022047077 A1 | 3/2022 |
| WO | WO-2022103774 A1 | 5/2022 |

OTHER PUBLICATIONS

Butson, C. et al., "Current steering to Control the Volume of Tissue Activated During Deep Brain Stimulation" Brain Stimul. (2008) (1): 7-15.
EP14813206 Examination Report dated Apr. 23, 2020. 2 pages.
European Search Report and Written Opinion in EP Application No. 16845235.7, dated Apr. 24, 2019, 8 pages.
European Search Report and Written Opinion in EP Application No. 13852295.8, dated May 12, 2016, 10 pages.
European Search Report and Written Opinion in EP Application No. 16747389.1, dated Jul. 5, 2018, 8 pages.
European Search Report and Written Opinion in EP Application No. 17753756.0, dated Nov. 11, 2019, 9 pages.
European Search Report and Written Opinion in EP Application No. 17770982.1, dated Sep. 26, 2019, 7 pages.
European Search Report and Written Opinion in EP Application No. 17831624.6, dated Feb. 20, 2020, 9 pages.
European Search Report and Written Opinion in EP Application No. 18756643.5, dated Dec. 3, 2020, 10 pages.

(56) References Cited

OTHER PUBLICATIONS

European Search Report and Written Opinion in EP Application No. 18797777.2, dated Jan. 14, 2021, 7 pages.
Final Office Action dated Nov. 21, 2022, for U.S. Appl. No. 16/222,959, 21 pages.
International Preliminary Report on Patentability dated Mar. 9, 2023, for PCT/US2021/047815, 5 pages.
International Search Report and Written Opinion for PCT/US2014/043023; dated Oct. 6, 2014, 13 pages.
International Search Report and Written Opinion for PCT/US2015/020808, dated Jun. 24, 2015, 8 pages.
International Search Report and Written Opinion for PCT/US2015/036821, dated Dec. 18, 2015, 13 pages.
International Search Report and Written Opinion for PCT/US2016/016888, dated Apr. 14, 2016, 8 pages.
International Search Report and Written Opinion for PCT/US2016/051177, dated Nov. 10, 2016, 18 pages.
International Search Report and Written Opinion for PCT/US2017/017978, dated May 5, 2017, 7 pages.
International Search Report and Written Opinion for PCT/US2017/023400, dated May 23, 2017, 8 pages.
International Search Report and Written Opinion for PCT/US2017/042351, dated Sep. 26, 2017, 9 pages.
International Search Report and Written Opinion for PCT/US2018/019522, dated Jun. 15, 2018, 12 pages.
International Search Report and Written Opinion for PCT/US2018/031904, dated Jul. 26, 2018, 10 pages.
International Search Report and Written Opinion for PCT/US2020/040766, dated Oct. 6, 2020, 7 pages.
International Search Report and Written Opinion for PCT/US2020/066901, dated Mar. 15, 2021, 7 pages.
Lee et al, "Predicted effects of pulse width programming in spinal cord stimulation: a mathematical modeling study" Med Biol Eng Comput 49:765-774 (2011). https://doi.org/1 0.1007 /s11517-011-0780-9.
Lenssen, Anneke et al, "Bimodal listeners are not sensitive to interaural time differences in unmodulated low-frequency stimuli," The Journal of the Acoustical Society of America, American Institute of Physics for the Acoustical Society of America, New York, NY, vol. 129, No. 6, Jun. 1, 2011, pp. 3457-3460.
Non-Final Office Action dated Feb. 24, 2023, for U.S. Appl. No. 17/240,629, filed Apr. 26, 2021, 12 pages.
Non-Final Office Action dated Apr. 14, 2023, for U.S. Appl. No. 17/726,378, filed Apr. 21, 2022, 15 pages.
Notice of Allowance dated May 22, 2023, for U.S. Appl. No. 16/222,959, filed Dec. 17, 2028, 11 pages.
Office Action dated Oct. 20, 2017 for U.S. Appl. No. 15/264,864, 14 pages.
PCT/US2017/034553 International Search Report and Written Opinion dated Oct. 10, 2017, 9 pages.
U.S. Appl. No. 63/042,293, inventors Mishra; Lakshmi Narayan et al., filed on Jun. 22, 2020.
U.S. Appl. No. 14/975,358 Office Action dated Dec. 5, 2019. 9 pages.
U.S. Appl. No. 14/975,358 Office Action dated Jul. 27, 2020. 12 pages.
U.S. Appl. No. 14/975,358 Office Action dated May 15, 2018. 9 pages.
U.S. Appl. No. 14/975,358 Office Action dated Nov. 2, 2020. 18 pages.
U.S. Appl. No. 14/975,358 Office Action dated Nov. 20, 2018. 9 pages.
U.S. Appl. No. 15/664,231 Office Action dated Aug. 6, 2020. 15 pages.
U.S. Appl. No. 15/664,231 Office Action dated Jan. 24, 2020. 16 pages.
U.S. Appl. No. 15/664,231 Office Action dated Jul. 10, 2020. 15 pages.
U.S. Appl. No. 15/664,231 Office Action dated Mar. 8, 2021. 25 pages.
U.S. Appl. No. 16/104,829 Notice of Allowance dated Jul. 6, 2021. 5 pages.
U.S. Appl. No. 16/104,829 Office Action dated Jan. 8, 2021. 20 pages.
U.S. Appl. No. 16/104,829 Office Action dated May 21, 2020. 15 pages.
U.S. Appl. No. 16/672,921 Notice of Allowance dated Apr. 23, 2021. 7 pages.
U.S. Appl. No. 16/672,921 Office Action dated Feb. 16, 2021. 11 pages.
U.S. Appl. No. 16/672,921 Office Action dated Mar. 22, 2021. 12 pages.
Extended European Search Report dated Jun. 12, 2023, for EP Application No. 20834931.6, 9 pages.
International Search Report and Written Opinion dated Jan. 31, 2022 for PCT/US2021/058673, 8 pages.
Final Office Action dated Jun. 16, 2023, for U.S. Appl. No. 17/372,095, filed Jul. 9, 2021, 31 pages.

* cited by examiner

B-B

C-C

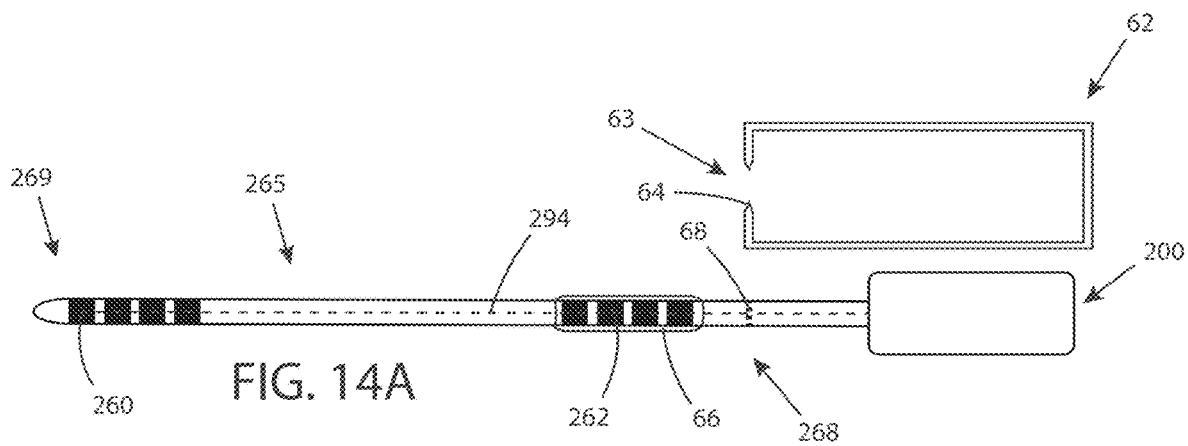
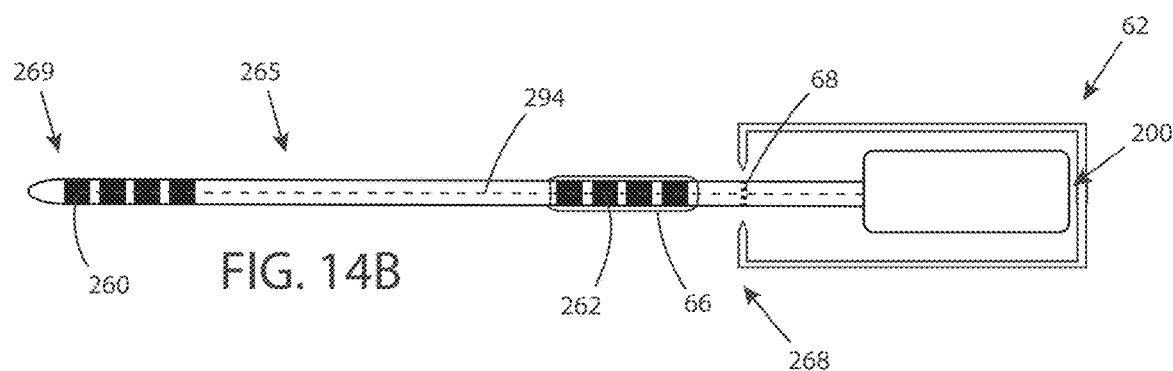
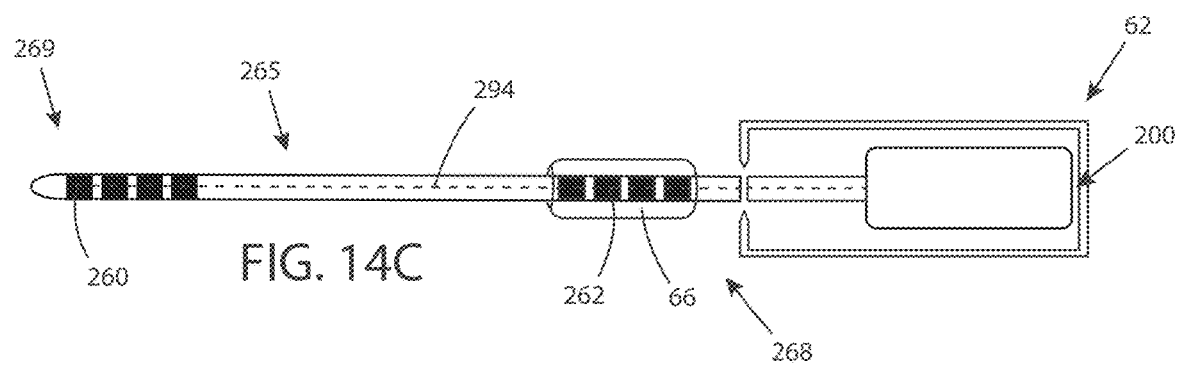
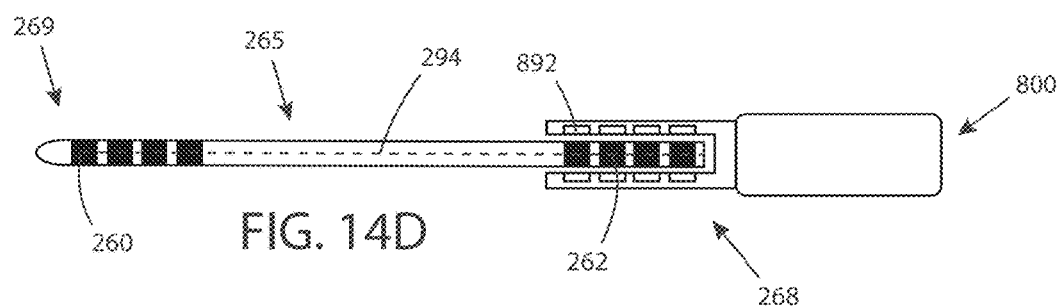

APPARATUS WITH SEQUENTIALLY IMPLANTED STIMULATORS

CROSS REFERENCE

This application is a continuation of U.S. patent application Ser. No. 16/539,977, filed Aug. 13, 2019, now U.S. Pat. No. 11,160,980, which is a continuation of PCT Application No. PCT/US2018/019522, filed Feb. 23, 2018, which claims priority U.S. Provisional Patent Application No. 62/463,328, filed Feb. 24, 2017, the contents of which are incorporated herein by reference in their entirety for all purposes.

DESCRIPTION OF THE INVENTION

Related Applications

This application is related to: U.S. patent application Ser. No. 14/424,303, titled "Wireless Implantable Sensing Devices", filed Feb. 26, 2015; U.S. patent application Ser. No. 14/975,358, titled "Method and Apparatus for Minimally Invasive Implantable Modulators", filed Dec. 18, 2015; U.S. patent application Ser. No. 15/264,864, titled "Method and Apparatus for Versatile Minimally Invasive Neuromodulators", filed Sep. 14, 2016; U.S. patent application Ser. No. 15/385,729, titled "Method and Apparatus for Neuromodulation Treatments of Pain and Other Conditions", filed Dec. 20, 2016; International PCT Patent Application Serial Number PCT/US2016/016888, titled "Medical Apparatus Including an Implantable System and an External System", filed Feb. 5, 2016; International PCT Patent Application Serial Number PCT/US2016/051177, titled "Apparatus for Peripheral or Spinal Stimulation", filed Sep. 9, 2016; International PCT Patent Application Serial Number PCT/US2017/017978, titled "Apparatus with Enhanced Stimulation Waveforms", filed Feb. 15, 2017; U.S. Provisional Patent Application Ser. No. 62/311,297, titled "Devices and Methods for Positioning External Devices in Relation to Implanted Devices", filed Mar. 21, 2016; U.S. Provisional Patent Application Ser. No. 62/341,418, titled "Methods and Systems for Insertion and Fixation of Implantable Devices", filed May 25, 2016; U.S. Provisional Patent Application Ser. No. 62/363,742, titled "Methods and Systems for Treating Pelvic Disorders and Pain Conditions", filed Jul. 18, 2016; and U.S. Provisional Patent Application Ser. No. 62/441,056, titled "Stimulation Apparatus", filed Dec. 30, 2016; the content of each of which is incorporated herein by reference in its entirety for all purposes.

FIELD OF THE INVENTION

The present invention relates generally to a medical apparatus for a patient, and in particular, an apparatus that provides sequentially implanted stimulators that perform both a stimulation trial period as well as a long-term stimulation therapy.

BACKGROUND OF THE INVENTION

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY

According to an aspect of the present inventive concepts, a stimulation apparatus for a patient comprises an external system configured to transmit transmission signals and implantable system configured to receive the transmission signals from the external system. The external system comprises a first external device comprising: at least one external antenna configured to transmit the transmission signals to the implantable system; an external transmitter configured to drive the at least one external antenna; an external power supply configured to provide power to at least the external transmitter; and an external controller configured to control the external transmitter. The implantable system comprises: at least one implantable lead for implanting under the skin of the patient and comprising at least one stimulation element configured to deliver stimulation energy to tissue of the patient, and a first implantable device. The first implantable device comprises: at least one implantable antenna configured to receive the transmission signals from the external system, the transmission signal comprising power and data; an implantable receiver configured to receive the transmission signals from the at least one implantable antenna; a first implantable connector for operably connecting to the at least one implantable lead; an implantable controller configured to deliver energy to the at least one stimulation element of the at least one implantable lead, the delivered energy provided by the transmission signal received from the external device; and an implantable housing surrounding at least the implantable controller and the implantable receiver. The implantable system comprises a second implantable device comprising: at least one implantable antenna configured to receive the transmission signals from the external system, the transmission signal comprising data; an implantable receiver configured to receive the transmission signals from the at least one implantable antenna; an implantable energy storage assembly comprising a battery and/or a capacitor; a second implantable connector for operably connecting to the at least one implantable lead; an implantable controller configured to deliver energy to the at least one stimulation element of the at least one implantable lead, the delivered energy provided by the implantable energy storage assembly; and an implantable housing surrounding at least the implantable controller and the implantable receiver. The first implantable device is configured to be attached to the at least one implantable lead for a first time period, and the second implantable device is configured to be attached to the at least one implantable lead for a second time period, subsequent to the first time period.

According to another aspect of the present inventive concepts, a stimulation apparatus for a patient comprises at least one implantable lead for implanting under the skin of the patient and comprising at least one stimulation element; an external system comprising: a first external device maintained outside of the patient and configured to transmit power and/or data; and an implantable system comprising: a first implantable device for implanting under the skin of the patient and configured to receive the power and/or data from the first external device; and a second implantable device for implanting under the skin of the patient. The first implantable device is configured to be attached to the at least one implantable lead for a first time period; and the second implantable device is configured to be attached to the at least one implantable lead for a second time period, subsequent to the first time period.

In some embodiments, the at least one implantable device comprises a single implantable lead, and the first implantable device and the second implantable device each attach to the single implantable lead.

In some embodiments, the at least one implantable lead comprises a first implantable lead and a second implantable lead, and the first implantable device attaches to the first implantable lead and the second implantable device attaches to the second implantable lead. The first implantable lead can be pre-attached to the first implantable device. The second implantable lead can be pre-attached to the second implantable device.

In some embodiments, the apparatus further comprises a filament extending from the first implantable device housing, and the filament operably attaches to the first implantable connector. The apparatus can further comprise a fitting which surrounds the filament and the first implantable connector.

In some embodiments, the apparatus further comprises a filament extending from the second implantable device housing, and the filament operably attaches to the second implantable connector. The apparatus can further comprise a fitting which surrounds the filament and the second implantable connector.

In some embodiments, the at least one implantable lead comprises a proximal portion and a distal portion, and the distal portion is detachable from the proximal portion. The detachable distal portion can be configured to attach to the second implantable connector. The proximal portion can be pre-attached to the first implantable device.

In some embodiments, the first implantable device housing comprises a clam-shell design configured to be compressed to operably connect the first implantable connector to the at least one implantable lead. The apparatus can further comprise at least one gasket configured to seal the first implantable device to the at least one implantable lead.

In some embodiments, the apparatus further comprises a tool configured to slidingly engage and expand the first implantable connector, after which the at least one implantable lead is inserted into and operably connected to the first implantable connector. The tool can be configured to be removed after the at least one implantable lead is inserted into the first implantable connector. The apparatus can further comprise at least one gasket configured to seal the first implantable device to the at least one implantable lead.

In some embodiments, the apparatus further comprises a sleeve configured to slidingly receive the at least one implantable lead, slidingly engage the first implantable connector, and operably connect the at least one implantable lead to the first implantable connector. The sleeve can include multiple connecting segments which connect the at least one implantable lead to the first implantable connector. The apparatus can further comprise at least one gasket configured to seal the first implantable device to the at least one implantable lead. The at least one gasket can comprise connecting segments which operably connect the at least one implantable lead to the first implantable connector.

In some embodiments, the first implantable connector comprises frictionally engaging contacts which operably connect the at least one implantable lead to the first implantable connector. The frictionally engaging contacts can comprise contacts selected from the group consisting of: electromechanical brushes; interference connector; canted springs; conductive mesh; deformable fingers; and combinations thereof. The apparatus can further comprise at least one gasket configured to seal the first implantable device to the at least one implantable lead.

In some embodiments, the first implantable connector comprises rotating contacts which operably connect the at least one implantable lead to the first implantable connector. Each rotating contact can comprise a hinge, an extension arm and a conductive pin. Each rotating contact can pass through the first implantable device housing during rotation. The housing can comprise holes through which the rotating contacts pass through. The apparatus can further comprise at least one gasket configured to seal the first implantable device to the at least one implantable lead.

In some embodiments, the first implantable connector comprises spring-loaded contacts which operably connect the at least one implantable lead to the first implantable connector. The apparatus can further comprise a compression element which compresses the first implantable connector around the at least one implantable lead. The apparatus can further comprise at least one gasket configured to seal the first implantable device to the at least one implantable lead.

In some embodiments, the first implantable device housing comprises a rollable housing configured to circumferentially surround the at least one implantable lead. The housing can comprise a flexible material and/or hinged segments.

In some embodiments, the second time period comprises a longer duration than the first time period.

In some embodiments, the first implantable device is configured to receive power and data from the external system, and the second implantable device is configured to receive data from the external system. The second implantable device does not receive power from the external system.

In some embodiments, the first implantable connector and the second implantable connector comprise similar construction and arrangement.

In some embodiments, the first implantable connector and the second implantable connector comprise dissimilar construction and arrangement. The first implantable connector can be configured to provide a contamination-preventing seal about the at least one implantable lead for at least a first time period, and the second implantable connector can be configured to provide a contamination-preventing seal about the at least one implantable lead for a second time period, and the first time period is shorter than the second time period. The first time period can be less than or equal to 3 months. The second time period can be greater than or equal to 3 months.

In some embodiments, the first implantable device comprises an implantable energy storage assembly. The second implantable device energy storage assembly can have a greater energy storage capacity than the first implantable device energy storage assembly. The second implantable device energy storage assembly can have at least 10 times the energy storage capacity as the energy storage capacity of the first implantable device energy storage assembly. The first implantable device energy storage assembly can comprise an energy storage capacity of no more than 0.6 Joules, no more than 0.7 Joules, and/or no more than 40 Joules. The second implantable device energy storage assembly can comprise an energy storage capacity of at least 60 Joules, at least 700 Joules, and/or at least 4,000 Joules.

In some embodiments, the second implantable device energy storage assembly comprises an energy storage capacity of at least 60 Joules, at least 700 Joules, and/or at least 4,000 Joules.

In some embodiments, the transmission signals comprise a frequency between 10 MHz and 10.6 GHz. The transmission signal can comprise a frequency proximate to 40.68 MHz.

In some embodiments, the apparatus is configured to provide the stimulation energy in a waveform with an amplitude between 0.01 mA and 15 mA. The apparatus can be configured to provide the stimulation energy in a waveform with an amplitude between 0.01 mA and 10 mA.

In some embodiments, the apparatus is configured to treat hernia pain. At least one of the first implantable device or the second implantable device can deliver stimulation at a frequency less than or equal to 1 kHz. At least one of the first implantable device or the second implantable device can deliver stimulation at a frequency greater than or equal to 1 kHz. The at least one stimulation element can be configured to be positioned proximate nerves and/or their branches. The at least one stimulation element can be configured to deliver subcutaneous field stimulation. The at least one stimulation element can be configured to deliver transvascular stimulation.

In some embodiments, the apparatus is configured to treat knee pain. The at least one stimulation element can be configured to stimulate nerves innervating the knee and/or tissue surrounding the knee. The at least one stimulation element can be configured to deliver subcutaneous field stimulation. The at least one stimulation element can be configured to deliver transvascular stimulation. The at least one stimulation element can be configured to stimulate one or more nerves selected from the group consisting of: medial femoral cutaneous and/or infrapatellar cutaneous branches of saphenous nerve; constant articular branches of common peroneal, lateral retinacular nerve; lateral, medial, and/or anterior cutaneous femoral nerve, infrapatellar branch of saphenous nerve, medial and/or lateral retinacular nerve and/or articular branches of peroneal nerve; obturator, posterior tibial and/or sciatic nerves; tibial nerve; superior, middle and/or inferior genicular nerves; nerves arising from the common peroneal such as the superior lateral, inferior lateral, and/or recurrent genicular nerves; nerves arising from the obturator nerve such as the genicular branch of obturator; and nerves arising from the femoral nerve such as the saphenous nerve; and combinations thereof.

In some embodiments, the apparatus is configured to treat carpal tunnel syndrome. The apparatus can be configured to deliver stimulation to tissue selected from the group consisting of: median nerve tissue; ulnar nerve tissue; radial nerve tissue; and combinations thereof.

In some embodiments, least one of the first implantable device or the second implantable device comprises a sensor configured to produce a signal correlating to a level of contamination. The sensor can comprise a sensor selected from the group consisting of: pH sensor; optical sensor; chemical sensor; and combinations thereof. The apparatus can be configured to produce an alarm when detected contamination exceeds a threshold.

In some embodiments, the apparatus is configured to treat diabetic neuropathy. The apparatus can be configured to deliver stimulation to tibial nerve tissue.

In some embodiments, the apparatus is configured to treat pain. The apparatus can be configured to treat back pain. The apparatus can be configured to treat knee pain.

In some embodiments, the apparatus is configured to treat a type of pain selected from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations thereof.

In some embodiments, the apparatus is configured to treat a pelvic dysfunction. The apparatus can be configured to treat overactive bladder.

In some embodiments, the apparatus is configured to treat a patient disease or disorder selected from the group consisting of: chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations thereof.

In some embodiments, the apparatus is further configured as a diagnostic apparatus. The apparatus can further comprise a sensor configured to record diagnostic information. The first implantable device and/or the second implantable device can comprise the sensor. The first external device can comprise the sensor. The at least one implantable lead can comprise the sensor.

In some embodiments, the apparatus is configured to deliver stimulation energy to spinal cord tissue.

In some embodiments, the apparatus is configured to deliver energy selected from the group consisting of: electrical energy; magnetic energy; electromagnetic energy; light energy; infrared light energy, visible light energy; ultraviolet light energy; mechanical energy; thermal energy; heat energy; cryogenic energy; sound energy; ultrasonic sound energy; high intensity focused ultrasound energy; low intensity focused ultrasound energy; subsonic sound energy; chemical energy; and combinations thereof.

In some embodiments, the apparatus is configured to randomly vary stimulation delivery. The apparatus can be configured to vary stimulation based on a probability distribution.

In some embodiments, the apparatus further comprises at least one functional element. The at least one functional element can comprise a sensor. The first implantable device and/or the second implantable device can comprise the sensor. The first external device can comprise the sensor. The at least one functional element can comprise a transducer. The first implantable device and/or the second implantable device can comprise the transducer. The first external device can comprise the transducer.

According to another aspect of the present inventive concepts, a method of providing stimulation therapy to a patient comprises (a) providing the stimulation apparatus according to any claim herein, (b) implanting a first implantable lead and the first implantable device in the patient, and connecting the first implantable lead to the first implantable device; (c) delivering stimulation energy to patient tissue via the first implantable device for a trial period; (d) detaching the first implantable lead from the first implantable device, explanting the first implantable device, implanting the second implantable device, and attaching an implantable lead to the second implantable device; and (e) delivering stimulation energy to the patient via the second implantable device for a therapy period.

In some embodiments, in step (d) the second implantable device is attached to the first implantable lead.

In some embodiments, the therapy period is of longer duration than the trial period.

In some embodiments, the trial period comprises a duration of at least 1 week.

In some embodiments, the trial period comprises a duration of at least 1 month.

In some embodiments, the trial period comprises a duration of at least 2 months.

In some embodiments, the trial period comprises a duration of at least 3 months.

In some embodiments, the therapy period comprises a duration of at least 3 months.

In some embodiments, during step (c), one or more stimulation parameters are varied.

In some embodiments, step (d) comprises detaching a first portion of the first implantable lead from a second portion of the first implantable lead.

In some embodiments, the at least one implantable lead comprises a distal portion including the at least one stimulation element and a proximal portion including at least one contact, and the at least one stimulation element and the at least one contact are operably connected. The distal portion can further comprise a flex circuit comprising one or more traces configured to operably connect the at least one stimulation element and the at least one contact. The distal portion can further comprise a covering surrounding the flex circuit, and the covering can comprise one or more recesses to expose the at least one stimulation element. The distal portion can further comprise a conductive rod and a layer stack applied to the conductive rod. The layer stack can comprise alternating layers of an insulator and a conductor, and an outer most layer of the layer stack can comprise the insulator. The alternating layers of insulator and conductor can be applied using one or more of the following deposition processes: sputtering; evaporation; dipping; plating; spraying; and chemical vapor deposition. The layer stack can comprise one or more recesses to expose a portion of the conductor rod and/or conductor layer, and the exposed portion of the conductor rod and/or conductor layer can comprise the at least one stimulation element. The conductive rod and/or conductor layer can be configured to operably connect to the at least one contact.

According to another aspect of the present inventive concepts, a method of treating a patient disease or disorder comprises providing a stimulation apparatus for a patient. The stimulation apparatus can comprise an implantable system. The implantable system can comprise an implantable lead comprising a distal portion including at least one stimulation element and a proximal portion including at least one contact, the at least one stimulation element and the at least one contact can be operably connected, and the at least one stimulation element can be configured to deliver stimulation energy to tissue of the patient. The implantable system can comprise an implantable device comprising a connector for operably connecting to the at least one contact of the implantable lead and a controller configured to deliver stimulation energy to the at least contact, and the at least one contact can be configured to deliver energy to the at least one stimulation element of the implantable lead. The method can comprise (a) implanting the implantable lead under the skin of the patient and operably connecting the connector of the implantable device to a first contact of the implantable lead; (b) delivering a minimum stimulation energy to patient tissue via a first stimulation element; (c) gradually increasing the minimum stimulation energy to achieve a therapeutic stimulation energy; (d) decreasing the therapeutic stimulation energy to the minimum stimulation energy; (e) operably disconnecting the connector from the first contact and operably connecting the connector to a second contact of the implantable lead; and (f) repeating (b) through (e) with remaining contacts of the implantable lead to achieve a therapeutic stimulation energy with remaining stimulation elements.

In some embodiments, the method further comprises (g) implementing a long-term therapy after a therapeutic stimulation energy is achieved with the final contact and final stimulation element, and the long-term therapy implements the therapeutic stimulation energy achieved with each contact and stimulation element.

According to another aspect of the present inventive concepts, a stimulation apparatus for a patient comprising: a first implantable device comprising an implantable lead, the implantable lead comprising at least one contact and at least one stimulation element, and the at least one contact and the at least one stimulation element are operably connected; a second implantable device; and a lead removal tool configured to remove the implantable lead from the first implantable device. The implantable lead can be configured to operably connect to the second implantable device once removed from the first implantable device.

In some embodiments, the first implantable device comprises a short-term implantable device.

In some embodiments, the second implantable device comprises a long-term implantable device.

In some embodiments, the first implantable device and the implantable lead are integrated.

In some embodiments, the implantable lead is fixedly attached to the first implantable device during a manufacturing process.

In some embodiments, the first implantable device is operably attached to the one or more stimulation elements via one or more wires.

In some embodiments, the at least one contact of the implantable lead comprises an insulating material. The insulating material can comprise a passivation layer applied to the at least one contact. The insulating material can comprise an insulating sleeve that surrounds the at least one contact. The insulating material can extend from a most proximal contact to a most distal contact of the implantable lead. The insulating material can be configured to be removed from the at least one contact. The insulating material can be removed via a peeling process.

In some embodiments, the first implantable device and the implantable lead are operably attached via a connector.

In some embodiments, the lead removal tool comprises an opening, and the opening is configured to slidingly receive the first implantable device. The opening can comprise one or more projections, and the one or more projections can be configured to engage the implantable lead. The one or more projections can be configured to engage a proximal portion of the implantable lead. The one or more projections can be configured to engage the implantable lead at pre-determined location, and the pre-determined location can comprise a marker positioned on the implantable lead. The marker can be positioned at weakened portion of the implantable lead. The one or more projections can be configured to travel inward and frictionally engage the implantable lead in response to an external force. The one or more projections can cause a break in the implantable lead, and the implantable lead can be separated from the first implantable device.

In some embodiments, the second stimulation device can slidingly receive and operably engage the at least one contact of the implantable lead.

In some embodiments, the apparatus further comprises a lead attachment assembly. The lead attachment assembly can comprise an attachment mechanism configured to attach an implantable lead to a stimulation device. The attachment mechanism can comprise a base portion comprising one or more contacts operably connected to a conduit and one or more hinged portions. The one or more hinged portions can comprise a first recess configured to slidingly receive at least a portion of the implantable lead. The one or more contacts of the base portion can be configured to extend into the first recess and operably connect to one or more contacts of the implantable lead.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 14A-D are side views of an implantable system comprising a short-term (temporary) implantable device with an integrated lead, and a lead removal tool, consistent with the present inventive concepts.

DETAILED DESCRIPTION OF THE DRAWINGS

Figure 1:
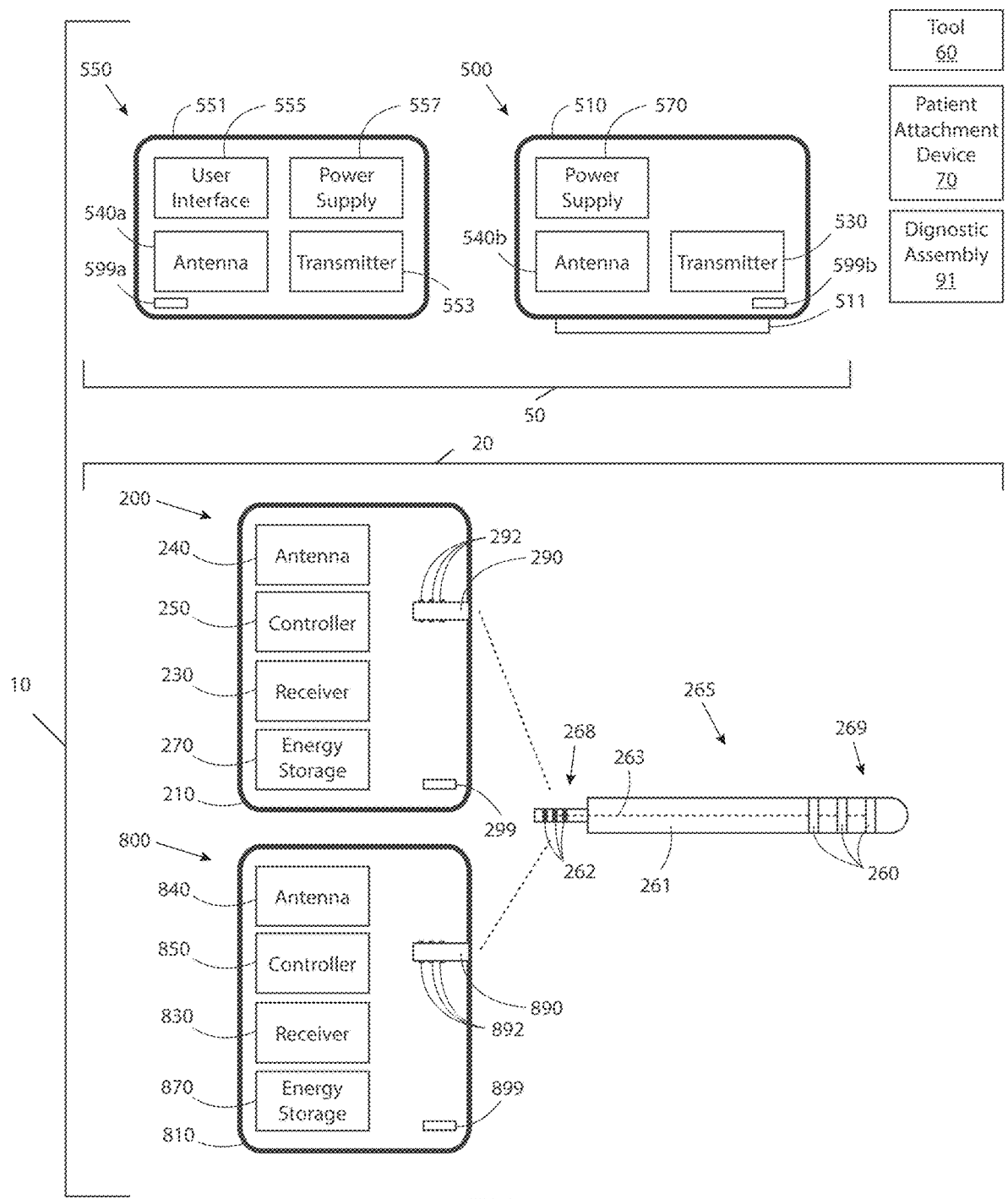
FIG. 1 is a schematic view of a medical apparatus comprising an external system and two implantable systems, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the system of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "functional element" where used herein, is the be taken to include a component comprising one, two or more of: a sensor; a transducer; an electrode; an energy delivery element; an agent delivery element; a magnetic field generating transducer; and combinations of one or more of these. In some embodiments, a functional element comprises a transducer selected from the group consisting of: light delivery element; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, a functional element comprises a needle, a catheter (e.g. a distal portion of a catheter), an iontophoretic element or a porous membrane, such as an agent delivery element configured to deliver one or more agents. In some embodiments, a functional element comprises one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); thermal energy to tissue (e.g. heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent between a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "connection", "connected", "connecting" and the like, where used herein, are to be taken to include any type of connection between two or more components. The connection can include an operable connection which allows multiple connected components to operate together such as to transfer information, power and/or material (e.g. an agent to be delivered) between the components. An operable connection can include a physical connection, such as a physical connection including one or more wires, optical fibers, wave guides, tubes such as fluid transport tubes and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

The terms "stimulation parameter", "stimulation signal parameter" or "stimulation waveform parameter" where used herein can be taken to refer to one or more parameters of a stimulation waveform (also referred to as a stimulation signal). Applicable stimulation parameters of the present inventive concepts shall include but are not limited to: amplitude (e.g. amplitude of voltage and/or current); average amplitude; peak amplitude; frequency; average frequency; period; phase; polarity; pulse shape; a duty cycle parameter (e.g. frequency, pulse width, and/or off time); inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g. the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an inter-phase gap can be present within a single pulse. The term "quiescent period" where used herein can refer to a period of time during which zero energy or minimal energy is delivered (e.g. insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. In some embodiments, the implantable system comprises a first implantable device that delivers stimulation energy via energy received wirelessly from one or more external devices, and a second implantable device that delivers stimulation energy via an integral (e.g. implanted) battery. In these embodiments, the first implantable device can be configured to deliver stimulation energy during a limited period of time (e.g. a trial period in which stimulation settings are determined and/or acceptability of the apparatus is determined), and the second implantable device can be configured to deliver stimulation energy for a prolonged period of time in which long-term stimulation therapy is provided to a patient. In these embodiments, a single implantable lead comprising one or more stimulation energy delivery elements (e.g. electrodes) can be connected to the first implantable device and then the second implantable device. In some embodiments, a first implantable device can be configured to remain implanted in the patient for a limited period of time, such as to reduce cost of manufacture, and a second implantable device is configured for a longer implant life. The first implantable device can be used in a trialing procedure in which the stimulation apparatus is assessed for acceptable use (e.g. by the patient and/or clinician) and/or one or more stimulation settings are optimized or otherwise determined.

Each implantable device can comprise one or more implantable antennas configured to receive power and/or data. In some embodiments, a first implantable device receives power and data, and a second implantable device receives data (e.g. without receiving power). Each implantable device can comprise an implantable receiver configured to receive the power and/or data from the one or more implantable antennas. Each implantable device can comprise one or more implantable functional elements. An implantable functional element can be configured to interface with the patient (e.g. interface with tissue of the patient or interface with any patient location). Alternatively or additionally, an implantable functional element can interface with a portion of an implantable device (e.g. to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to and/or receive a signal from) the one or more implantable functional elements. In some embodiments, an implantable controller of a first implantable device is configured to control one or more other implantable devices. Each implantable device can comprise an implantable energy storage assembly (e.g. a battery and/or a capacitor) configured to provide power to the implantable controller (e.g. a controller comprising a stimulation waveform generator), the implantable receiver and/or the one or more implantable functional elements. In some embodiments, an implantable energy storage assembly is further configured to provide power to an assembly that transmits signals via the implantable antenna (e.g. when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be tethered (e.g. electrically tethered) to the implantable housing. In some embodiments, one or more implantable functional elements are positioned on an implantable lead, such as a flexible lead mechanically fixed or attachable to the implantable housing and operably connected (e.g. electrically, fluidly, optically, and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded. In some embodiments, the implantable lead is configured to operably attach to and/or detach from, multiple implantable devices.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g. when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set and/or modify one or more treatment and/or data recording settings of the medical apparatus of the present inventive concepts. In some embodiments, the external programmer is configured to provide control signals to one or more external devices (e.g. one or more external devices that provide at least power to a first implantable device), and to provide control signals to an implantable device (e.g. a second implantable device that does not receive power from an external device). In some embodiments, the external programmer can be configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system comprising at least one implantable device configured to receive the power from the external system and to deliver stimulation energy to tissue. The implantable system can further comprise one or more additional implantable devices that do not receive power from the external system (e.g. implantable devices that have an internal battery or other power source that provides the stimulation energy). The delivered stimulation energy can comprise one or more stimulation waveforms, such as a stimulation waveform configured to enhance treatment of pain while minimizing undesired effects. The stimulation signal (also referred to as "stimulation energy" herein) delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic view of a stimulation apparatus for providing a therapy to a patient is illustrated, consistent with the present inventive concepts. Apparatus 10 comprises implantable system 20 and external system 50. External system 50 transmits transmission signals to one or more components of implantable system 20. These transmission signals can comprise power and/or data. Implantable system 20 comprises implantable device 200 which is configured to be implanted beneath the skin of a patient. In some embodiments, implantable system 20 comprises multiple similar or dissimilar implantable devices 200 (singly or collectively implantable device 200), such as is described in applicant's co-pending application International PCT Patent Application Serial Number PCT/US2017/017978, titled "Apparatus with Enhanced Stimulation Waveforms", filed Feb. 15, 2017, the content of which is incorporated herein in its entirety for all purposes. Each implantable device 200 can be configured to receive power and data from a transmission signal transmitted by external system 50, such as when stimulation energy delivered to the patient (e.g. to nerve or other tissue of the patient) by implantable device 200 is provided via wireless transmissions signals from external system 50. In some embodiments, implantable system 20 further comprises a second implantable device, implantable device 800 shown, also configured to be implanted beneath the skin of the patient. In these embodiments, implantable device 800 can provide one or more implantable devices that deliver stimulation energy to the patient without receiving power from external system 50, such as when power is (primarily) provided from a power source internal to implantable device 800 (e.g. energy storage assembly 870 shown or other energy storage element of implantable device 800). While not receiving power, implantable device 800 can receive data (e.g. stimulation parameters or other programming data) from external system 50.

Implantable system 20 can comprise one or more implantable leads, such as implantable lead 265 shown. Lead 265 comprises one or more stimulation elements (e.g. one or more electrodes or other energy delivering elements as described herein), stimulation element 260 (three shown in FIG. 1). Alternatively or additionally, one or more stimulation elements 260 can be positioned on housing 210 of implantable device 200 and/or housing 810 of implantable device 800, for example when current is delivered in a monopolar mode (e.g. current delivered between a stimulation element 260 on lead 265 and a stimulation element 260 on housing 210 and/or 810). Implantable device 200 is configured to operably connect (e.g. electrically, optically, acoustically and/or otherwise operably connect) to lead 265, via its implantable connector, attachment port 290, such as via a connection performed by a clinician during a surgical procedure in which one or more components of implantable system 20 are implanted in the patient. Implantable device 800 is also configured to operably connect to lead 265 (e.g. the same lead 265 or a newly implanted lead 265), via its implantable connector, attachment port 890. Attachment ports 290 and 890 can be of similar or dissimilar construction. For example, attachment port 290 can be constructed and arranged to provide a contamination-preventing seal with lead 265 for a limited time period (e.g. less than 3 months), while attachment port 890 can be constructed and arranged to provide a contamination-preventing seal with lead 265 for an extended time period (e.g. at least 3 months, at least 1 year, or at least 2 years). In some embodiments, implantable device 200 is configured to disconnect from lead 265 (e.g. in a second clinical procedure performed after the implantable device 200 implantation procedure), such that implantable device 800 can subsequently be connected to the same lead 265, such as is described herebelow in reference to FIG. 2. In these embodiments, implantable device 200 can be configured to be implanted in the patient to conduct a trial procedure via lead 265 (e.g. as described herebelow in reference to FIG. 2) for a trial period, after which implantable device 800 is implanted to provide stimulation therapy to the patient for a therapy period, such as via the same, previously implanted lead 265.

External system 50 can comprise an external device 500, which includes housing 510. In some embodiments, external system 50 comprises multiple external devices 500 (singly or collectively external device 500), also as is described in applicant's co-pending application International PCT Patent Application Serial Number PCT/US2017/017978, titled "Apparatus with Enhanced Stimulation Waveforms", filed Feb. 15, 2017. Each external device 500 can be configured to transmit transmission signals that send power and/or data to one or more components of implantable system 20, such as implantable device 200. Alternatively or additionally, external system 50 can comprise external programmer, programmer 550, which can comprise a user interface, such as user interface 555. Programmer 550 can be configured to transmit transmission signals that send data to: one or more external devices 500, one or more implantable devices 200, and/or one or more implantable devices 800, such as to adjust the settings of or otherwise control these components of apparatus 10. External programmer 550 can comprise housing (housing 551), a transmitting element (transmitter 553), a battery or other power supply (power supply 557), and one or more antennas (antenna 540*a*).

Apparatus 10 can be configured to stimulate tissue (e.g. stimulate nerve tissue such as tissue of the central nervous system or tissue of the peripheral nervous system, such as to neuromodulate nerve tissue), such as by having one or more implantable devices 200 and/or implantable devices 800 deliver energy to one or more tissue locations. In some embodiments, one or more implantable devices 200 deliver energy (e.g. continuously or intermittently) to the patient while simultaneously, or relatively simultaneously (e.g. power received from external system 50 within 60 seconds, within 5 minutes and/or within 15 minutes of stimulation delivery, "simultaneously" herein) receiving power from one or more external devices 500. In some embodiments, one or more implantable devices 800 deliver energy (e.g. continuously or intermittently) to the patient, where the energy is provided by an internal power source (e.g. a battery and/or capacitor, such as energy storage assembly 870 shown) without receiving externally supplied power. For example, implantable device 800 may not receive power from any external device for a time period of at least 1 hour, at least 1 day, at least 1 month or at least 1 year, while delivering stimulation energy during those same time periods. During those time periods of no energy being provided from an external source, one or more stimulation parameters of implantable device 800 can be varied during those periods, such as a variation based on data sent by programmer 550, an external device 500 and/or other external component of apparatus 10.

In some embodiments, apparatus 10 is further configured as a patient diagnostic apparatus, such as by having one or more implantable devices 200, one or more implantable devices 800, and/or one or more external devices 500 record a patient parameter (e.g. a patient physiologic parameter) from one or more tissue locations. In some embodiments, during its use, one or more implantable devices 200 at least receives power from one or more external devices 500 (e.g. with or without also receiving data).

Alternatively or additionally, apparatus 10 can be configured as a patient information recording apparatus, such as by having one or more implantable devices 200, one or more implantable devices 800, and/or one or more external devices 500 record patient information (e.g. patient physiologic information and/or patient environment information). In some embodiments, one or more implantable devices 200, one or more implantable devices 800, and/or one or more external devices 500 further collect information (e.g. status information or configuration settings) of one or more of the components of apparatus 10.

In some embodiments, apparatus 10 is configured to deliver stimulation energy to tissue to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, dorsal root, dorsal root ganglia, spinal nerves, ganglia, and/or other nerve tissue. The delivered energy can comprise energy selected from the group consisting of: electrical energy; magnetic energy; electromagnetic energy; light energy such as infrared light energy, visible light energy, and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver energy to tissue in a form selected from the group consisting of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. The coil or other magnetic field generating element can surround (e.g. at least partially surround) the target nerve and/or it can be incorporated as part of an anchoring system to the target tissue. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to one or more implantable devices 200, and the one or more implantable devices 200 delivers stimulation energy to tissue with a stimulation signal (also referred to as a stimulation waveform), with the power signal and the stimulation signal having one or more different characteristics. The power signal can further be modulated with data (e.g. configuration or other data to be sent to one or more implantable devices 200). In these embodiments, the characteristics of the stimulation signal delivered (e.g. amplitude, frequency, duty cycle, and/or pulse width), can be independent (e.g. partially or completely independent) of the characteristics of the power signal transmission (e.g. amplitude, frequency, phase, envelope, duty cycle, and/or modulation). For example, the frequency and modulation of the power signal can change without affecting the stimulation signal, or the stimulation signal can be changed (e.g. via programmer 550), without requiring the power signal to change. In some embodiments, implantable system 20 can be configured to rectify the power signal, and produce a stimulation waveform with entirely different characteristics (e.g. amplitude, frequency, and/or duty cycle) from the rectified power signal. Each implantable device 200 can comprise an oscillator and/or controller configured to produce the stimulation signal. In some embodiments, one or more implantable devices 200 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to one or more implantable devices 200, and each implantable device 200 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL); phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and each implantable device 200 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012, the content of which is incorporated herein by reference in its entirety for all purposes. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013, the content of which is incorporated herein by reference in its entirety for all purposes.

Apparatus 10 can be configured to treat pain, such as back and/or leg pain treated by stimulating dorsal root ganglia, and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these. In some embodiments, apparatus 10 is configured to treat a patient disease or disorder selected from the group consisting of: chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more stimulation elements 260 of lead 265 can be implanted at one or more spinal cord locations. In some embodiments, stimulation elements 260 comprise two or more stimulation elements (e.g. electrodes) that span multiple vertebra of the spinal column (e.g. multiple stimulation elements that span at least T8 to T9 and/or T-9 to T-10). Lead 265 can receive stimulation energy for a first time period from a connected implantable device 200, and subsequently for a second time period from a connected implantable device 800. One or more stimulation signals can be delivered to spinal cord tissue, such as to treat heart failure or other cardiac disease or disorder. In some embodiments, one or more stimulation elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more stimulation elements 260 of implantable system 20) are used to record a patient parameter, such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more stimulation elements 260 can be positioned proximate cardiac tissue and deliver a stimulation signal as described herein (e.g. based on power and/or data received by implantable system 20 from external system 50 or via an internal battery, such as energy storage assembly 870 of implantable device 800). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output, lung impedance and/or other properties or functions of the cardiovascular system), such as to determine an onset of cardiac activity dysfunction or other undesired cardiac state. In some embodiments, apparatus 10 is configured to both record cardiac or other information and deliver a stimulation signal to cardiac tissue (e.g. stimulation varied or otherwise based on the recorded information). For example, apparatus 10 can be configured such that external system 50 transmits power and/or data to implantable system 20 while lead 265 is attached to an implantable device 200, and transmits data (only) to implantable system 20 while lead 265 is attached to implantable device 800. Implantable system 20 monitors cardiac activity, and upon detection of an undesired cardiovascular state, implantable system 20 delivers a pacing and/or defibrillation signal to the tissue that is adjacent to one or more stimulation elements 260 configured to deliver a cardiac stimulation signal.

External device 500 can comprise a wrist band, a wrist watch or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's thigh, knee and/or ankle. In some embodiments, external device 500 comprises a band or other attachment device for positioning about the thorax, neck, groin and/or head of the patient. Power and/or data can be sent to the implantable device 200 from the external device 500, and data (e.g. blood glucose data) can be sent to external device 500 (or another component of external system 50) by implantable device 200, such as using a communication configuration known to those of skill in the art. Various closed loop sensing and stimulation delivery combinations and configurations should be considered within the spirit and scope of the present inventive concepts, including but not limited to: sensing a blood parameter such as white blood cell count and adjusting energy delivery; sensing a hormone level and adjusting energy delivery; sensing blood pressure and adjusting energy delivery; sensing neural activity and adjusting energy delivery, such as for treating epilepsy; and combinations of one or more of these.

External system 50 can be configured to transmit power and/or data (e.g. implantable device 200 configuration data) to one or more implantable devices 200 of implantable system 20. External system 50 can be configured to transmit data (e.g. implantable device 800 configuration data) to one or more implantable devices 800 of implantable system 20. Configuration data provided by external system 50 (e.g. via one or more antennas 540a of programmer 550 and/or one antennas 540b of one or more external devices 500, as described herein) can include when to initiate stimulation delivery (e.g. energy delivery), when to stop stimulation delivery, and/or data related to the value or change to a value of one or more stimulation settings as described herein. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

External system 50 can comprise one or more external devices 500 and/or one or more programmers 550. Programmer 550 can comprise one or more antennas 540a. Each external device 500 can comprise one or more antennas 540b. The one or more antennas 540a and/or 540b (generally antenna 540) can transmit power and/or data to one or more antennas 240 of each implantable device 200 and/or one or more antennas 840 of each implantable device 800, such as when a single implantable device 200 and/or a single implantable device 800 comprises one or more antennas 240 and/or 840 respectively, or when multiple implantable devices 200 and/or 800 (singly or collectively implantable device 200/800) each comprise one or more antennas 240 and/or 840 (singly or collectively antenna 240/840), respectively. In some embodiments, one or more antennas 540 define a radiation footprint (e.g. a footprint defining a volume, such as a volume of tissue, in which electromagnetic transmissions radiated by antennas 540 can be properly received by antennas 240/840), such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes.

External system 50 transmits power and/or data with a transmission signal comprising at least one wavelength, $\lambda$. External system 50 and/or implantable system 20 can be configured such that the distance between an external antenna 540 transmitting the power and/or data and one or more implantable antennas 240/840 receiving the power and/or data transmission signal is equal to between $0.1\lambda$ and $10.0\lambda$, such as between $0.2\lambda$ and $2.0\lambda$. In some embodiments, one or more transmission signals are delivered at a frequency range between 10 MHz and 10.6 GHz, such as between 0.1 GHz and 10.6 GHz, between 10 MHz and 3.0 GHz, between 40 MHz and 1.5 GHz, or between 0.902 GHz and 0.928 GHz, or in a frequency range proximate to 40.68 MHz, proximate to 866 MHz, or approximately between 863 MHz and 870 MHz.

In addition to transmitting power and/or data to implantable system 20, external system 50 can be further configured to provide information (e.g. patient information and/or apparatus 10 performance information) to one or more other devices of apparatus 10, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200/800. In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200/800 (e.g. via data transmitted by one or more antennas 240/840).

Each external device 500 can comprise housing 510, power supply 570, a transmitter 530, and/or one or more antennas 540b, as described herein.

One or more housings 510 (singly or collectively housing 510) of each external device 500 can comprise one or more rigid and/or flexible materials which surround various components of external device 500 such as antenna 540b, transmitter 530 and/or power supply 570. In some embodiments, a single external device 500 comprises multiple discrete (i.e. separate) housings 510, two or more of which can transfer data or other signals via a wired or wireless connection. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540b.

Housing 510 can comprise an adhesive element, not shown but such as an adhesive element configured to temporarily attach an external device 500 to the patient's skin. Housing 510 can be constructed and arranged to engage (e.g. fit in the pocket of) a patient attachment device, such as patient attachment device 70 described herebelow.

One or more antennas 540a and/or 540b (singly or collectively antenna 540) can each comprise one, two, three or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240/840, such as to adjust for movement of the array of the antennas 540 relative to the implanted antennas 240/840. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. One or more antennas 540 can be positioned in a housing (e.g. housing 510 or housing 551) that is otherwise void of other components (e.g. void of power supply 570 and transmitter 530), such as when an antenna 540 is positioned within a first housing 510 and communicates with components positioned in a second housing 510.

In some embodiments, a spacer 511 is positioned between antenna 540b and the patient's skin, such as a spacer comprising a thickened portion of housing 510 or a discrete spacer 511 placed on a side of housing 510 (as shown) or on a side of antenna 540b. Spacer 511 can comprise one or more materials that match the impedance of antenna 540b to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. when spacer 511 comprises a thermally insulating material). Alternatively, or additionally, housing 510 can comprise a heat insulating and/or dissipating material. Spacer 511 can comprise a soft or otherwise compressible material (e.g. foam) for patient comfort. Spacer 511 can be inflatable, such as to control the separation distance of an external antenna 540b from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; a loop antenna (e.g. a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm. Antenna 540 can be further configured to receive a signal, such as when an antenna 240/840 is configured to transmit data to an external device 500 and/or programmer 550. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200/800 (e.g. each containing one or more antennas 240/840). In some embodiments, a single external device 500, comprising one or more antennas 540b, can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 and/or programmer 550 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510) and/or a single programmer 550 (e.g. within housing 551). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200/800 operation depth; polarization; power efficiency; a radiation footprint; directional gain; beam shaping and/or focusing; sensitivity to implantable device 200/800 placement; patient comfort; patient usability; data transfer; and combinations of one or more of these. In some embodiments, the first antenna 540 can be optimized for a different design parameter than the second antenna 540, and each antenna 540 can be activated independently or simultaneously to realize both benefits. In some embodiments, the first antenna 540 can be similar to the second antenna 540 and placed in an array to increase the radiation footprint or placed in different external locations to operate with multiple implantable devices 200/800 implanted at different sites.

In some embodiments, a first external antenna 540 and a second external antenna 540 transmit power and/or data to a single implantable antenna 240 or 840. In some embodiments, a first antenna 540 and a second antenna 540 can transmit power and/or data to two or more antennas 240/840, the transmissions occurring simultaneously or sequentially. In sequential power and/or data transfers, a first external device 500 comprising a first one or more antennas 540b can be replaced (e.g. swapped) with a second external device 500 comprising a second one or more antennas 540b. Alternatively or additionally, sequential power and/or data transfer can be initiated by one or more of the following conditions: when the first external antenna 540 moves (e.g. moves relative to the implanted antenna 240/840); when a second external device 500 comprising a second antenna

540b is turned on or otherwise activated; when a second antenna 540 provides improved power and/or data transfer to the antenna 240/840 than is provided by a first antenna 540; and/or when power received from a first antenna 540 decreases (e.g. decreases below a threshold). In some embodiments, an antenna 240 receives power from a first antenna 540 and a second antenna 540, but only receives data from the first antenna 540. In some embodiments, a first antenna (e.g. an antenna 240, an antenna 840, or an antenna 540) is driven with a different carrier signal than a second antenna (e.g. an antenna 240, an antenna 840, or an antenna 540). The two carrier signals can comprise differences in amplitudes and/or relative phases as compared to each other. Each carrier signal can include a data transmission signal (e.g. data to be transmitted to an implantable device 200/800 from an external device 500 or to an external device 500 from an implantable device 200/800).

As described herein, one or more programmers 550 and/or external devices 500 can be configured to transmit data (e.g. configuration data) to one or more implantable devices 200/800. In programmer 550, antenna 540a transmits the data-based transmission signal produced by transmitter 553. In external device 500, antenna 540b transmits the data-based transmission signal produced by transmitter 530. In some embodiments, a transmitter 553 and/or a transmitter 530 (singly or collectively transmitter 553/530) is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, programmer 550 and/or one or more external devices 500 transmit data to one or more implantable devices 200/800 using time division multiple access (TDMA). In some embodiments, one or implantable devices 200/800 are independently addressable through unique identification (ID) codes. Alternatively or additionally, transmitters 553/530 can be configured to transmit one or more data signals with a bandwidth between 1 kHz and 100 MHz, between 0.1 MHz and 100 MHz, or between 1 MHz and 26 MHz.

One or more transmitters 553/530 can each comprise one or more external transmitters that drive one or more antennas 540. In some embodiments, transmitter 553/530 comprises a transmitter that operates in a frequency range between 10 MHz and 10.6 GHz, such as a transmitter that operates in a frequency range between 0.1 GHz and 10.6 GHz, between 10 MHz and 3.0 GHz, between 40 MHz and 1.5 GHz, or between 0.902 GHz and 0.928 GHz, or in a frequency range proximate to 40.68 MHz, proximate to 866 MHz, or approximately between 863 MHz and 870 MHz. Transmitter 553/530 can comprise a transmitter that produces a transmission signal with a power level between 0.1 W and 4.0 W, such as a transmission signal with a power level between 0.1 W and 2.0 W or between 0.2 W and 1.0 W.

As described herein, one or more external devices 500 can be configured to transmit power to one or more implantable devices 200, such as via a power transmission produced by transmitter 530 and sent to one or more antennas 540b. One or more transmitters 530 can deliver power to one or more implantable devices 200 simultaneously or sequentially. In some embodiments, one or more transmitters 530 are configured to adjust the level of power transmitted to one or more implantable devices 200/800, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g. when one or more implantable devices 200/800 are further configured to transmit data to external system 50); set a power transfer based on charge information and/or discharge information related to an implantable device 200/800 (e.g. charge rate and/or discharge rate of an implantable energy storage assembly 270 and/or 870); and combinations of one or more of these. In some embodiments, implantable system 20 comprises a first receiver 230 (e.g. of a first implantable device 200) and a second receiver 230 (e.g. of a second implantable device 200). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 553/530 (and/or another component of external system 50) is further configured as a receiver, such as to receive data from implantable system 20. For example, a transmitter 553/530 can be configured to receive data via one or more antennas 240/840 of one or more implantable devices 200/800. Data received can include patient information (e.g. patient physiologic information, patient environment information or other patient information) and/or information related to an implantable system 20 parameter (e.g. an implantable device 200/800 stimulation parameter and/or other configuration parameter as described herein).

In some embodiments, transmitter 553/530 comprises a first transmitter to transmit power and/or data to one implantable device 200 or 800, and a second transmitter to transmit data to a different device. In these embodiments, a second transmitter of transmitter 553/530 can be configured to transmit data to tool 60 or another device such as: external device 500 (e.g. when the transmission emanates from transmitter 553 of programmer 550); programmer 550 (e.g. when the transmission emanates from transmitter 530 of external device 500); a cell phone; a computer; a tablet; a computer network such as the internet or a LAN; and combinations of one or more of these. In some embodiments, the second transmitter of transmitter 553/530 comprises a wireless transmitter; a Bluetooth transmitter; a cellular transmitter; and combinations of one or more of these. In some embodiments, a functional element 599 (e.g. functional element 599a of programmer 550 and/or functional element 599b of external device 500) comprises a transmitter such as a Bluetooth transmitter.

Each power supply 557 and/or 570 (singly or collectively power supply 557/570) can be operably attached to a transmitter 553/530, and one or more other electrical components of programmer 550 or external device 500, respectively. Power supply 557/570 can comprise a power supplying and/or energy storage element selected from the group consisting of: battery; replaceable battery (e.g. via a battery door of housing 551 or 510, respectively); rechargeable battery; AC power converter; capacitor; and combinations of one or more of these. In some embodiments, power supply 557/570 comprises two or more batteries, such as two or more rechargeable batteries, such as to allow the first battery to be replaced (e.g. serially replaced) by the second battery. In some embodiments, power supply 557/570 is configured to provide a voltage of at least 3V. In some embodiments, power supply 557/570 is configured to provide a capacity between 1 Watt-hour and 75 Watt-hours, such as a battery or capacitor with a capacity of approximately 5 Watt-hours. In some embodiments, power supply 557/570 comprises an AC power source.

Each programmer 550 (singly or collectively programmer 550) comprises a programming device configured to control one or more components of apparatus 10, such as implantable device 200/800. Programmer 550 can comprise a user interface 555. Programmer 550 can send and/or receive commands to and/or from one or more external devices 500, such as via a wireless or wired connection (wired connection not shown but such as one or more insulated conductive wires). In some embodiments, one or more external devices 500 comprise programmer 550, such as when user interface 555 is integrated into housing 510 of external device 500. In some embodiments, apparatus 10 comprises multiple programmers 550.

Programmer 550 can be configured to adjust one or more parameters of apparatus 10, such as a stimulation parameter (e.g. a stimulation waveform parameter as described herein); a sensing parameter; a therapy parameter; a data recording parameter (e.g. a patient data recording parameter and/or an implantable device 200/800 data recording parameter); power transfer; data rate; activity of one or more external transmitters 553/530; activity of one or more external antennas 540; a stimulation element 260 parameter; a functional element 599 parameter; and combinations of one or more of these. Programmer 550 can be further configured to provide information, such as patient physiologic information recorded by one or more implantable devices 200/800, or apparatus 10 information, such as performance and/or configuration information (singly or collectively "status information") of one or more external devices 500 and/or implantable devices 200/800. In some embodiments, the programmer 550 uses information recorded by one or more implantable devices 200, implantable device 800, apparatus 10 information, and/or information from external devices 500 to adapt configuration parameters of one or more components of apparatus 10.

In some embodiments, programmer 550 comprises a lookup table of stimulation signal waveform patterns, such as to allow a clinician, patient and/or other operator of apparatus 10 to select a predetermined stimulation pattern. In some embodiments, programmer 550 comprises a set of adjustable stimulation signal parameters configured to be varied to allow an operator to construct customized waveforms, such as to vary one or more stimulation parameters described hereabove. In some embodiments, the programmer 550 is configured to allow an operator to create a customized waveform by specifying an amplitude of one or more discrete pulses or steps of a stimulation signal to be delivered by an implantable device 200/800.

In some embodiments, programmer 550 comprises a transmitter 553 configured to transmit data to tool 60 or another device such as a cell phone; computer; tablet; computer network such as the internet or a LAN; and combinations of one or more of these. In these embodiments, transmitter 553 can comprise a wireless transmitter; a Bluetooth transmitter; a cellular transmitter; and combinations of one or more of these. In some embodiments, programmer 550 comprises a receiver configured to receive data, or a transceiver configured to both transmit and receive data.

User interface 555 of programmer 550 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 599, such as functional elements 599a and/or 599b (singly or collectively functional element 599), shown positioned in programmer 550 and in external device 500, respectively. In some embodiments, one or more components of implantable system 20 can comprise one or more functional elements, such as functional element 299 of implantable device 200 and functional element 899 of implantable device 800, each shown in FIG. 1. Each functional element 299, 599 and/or 899 (singly or collectively functional element 299/599/899) can be configured as defined hereabove (e.g. a sensor, a transducer, and/or other functional element as described herein).

In some embodiments, a functional element 599 comprises one or more sensors configured to monitor performance of external device 500 and/or programmer 550 (e.g. to monitor the voltage of power supply 570, quality of transmission of power and/or data to implantable system 20, temperature of a portion of an external device 500, and the like).

In some embodiments, the functional element 299/599/899 can comprise an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more stimulation elements 260 and/or one or more functional elements 299/599/899.

In some embodiments, one or more functional elements 299/599/899 comprise a sensor, such as a sensor configured to record data related to a patient parameter (e.g. a patient physiologic parameter), an external system 50 parameter and/or an implantable system 20 parameter. In some embodiments, operation of one or more implantable devices 200/800 (e.g. stimulation energy delivered by one or more implantable devices 200/800) is configured to be delivered based on the data recorded by one or more sensor-based functional elements 299/599/899, such as in a closed-loop energy delivery mode.

Functional element 299/599/899 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity; electrical activity produced by skeletal muscles (e.g. as measured using electromyography, EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 299/599/899 can comprise one or more sensors configured to record data representing a parameter of external system 50, implantable system 20, and/or any component of apparatus 10. Functional element 299/599/899 can comprise one or more sensors selected from the group consisting of: an energy sensor; a voltage sensor; a current sensor; a temperature sensor (e.g. a temperature of one or more components of external device 500, programmer 550, and/or implantable device 200/800); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250 and/or 850 described herebelow) the data recorded by functional element 299/599/899 to assess one or more of: power transfer; link gain; power use; energy within power supply 557/570; performance of power supply 557/570; expected life of power supply 557/570; discharge rate of power supply 557/570; ripple or other variations of power supply 557/570; matching of antennas 240/840 and 540; communication error rate between implantable device 200/800 and external device 500; integrity of transmission between implantable device 200/800 and external device 500; and combinations of one or more of these.

In some embodiments, functional element 299 and/or functional element 899 (singly or collectively 299/899) comprises a sensor configured to produce a signal relating to the level of contamination in an undesired location (e.g. within implantable device 200/800 and/or within the connection between implantable device 200/800 and lead 265). For example, functional element 299/899 can comprise a contamination-detecting sensor selected from the group consisting of: pH sensor; optical sensor; chemical sensor; and combinations of one or more of these. In these embodiments, apparatus 10 can be configured to enter an alarm state (e.g. produce an audible, tactile or visual alarm such as an alarm produced by external device 500, controller 550 and/or implantable device 200/800) when a contamination level exceeds a threshold.

In some embodiments, one or more functional elements 599 are positioned on housing 551 and/or 510 (singly or collectively housing 551/510). A functional element 599 can comprise a body conduction sensor, such as a body conduction sensor configured to record and/or receive data via skin conduction. A functional element 299/599/899 can be configured to record data associated with stimulation delivered by one or more implantable devices 200/800 (e.g. record data associated with stimulation energy delivered by one or more stimulation elements 260), such as to provide closed loop or semi-closed loop stimulation. A functional element 299/599/899 can be configured to record temperature, such as when apparatus 10 is configured to deactivate or otherwise modify the performance of programmer 550, external device 500 and/or implantable device 200/800 when the recorded temperature (e.g. patient temperature, programmer 550 temperature, external device 500 temperature, and/or implantable device 200/800 temperature) exceeds a threshold.

In some embodiments, programmer 550, external device 500, and/or implantable device 200/800 comprises a temperature sensor, such as functional elements 299/599/899. The temperature-based functional element 299/599/899 can be positioned proximate one or more portions of programmer 550, external device 500, and/or implantable device 200/800. In these embodiments, the temperature data recorded by the functional element 299/599/899 is used to adjust one or more of: matching network; stimulation level (e.g. stimulation energy delivered by one or more implantable devices 200/800); power transmission level (e.g. level of power transmitted between one or more external devices 500 and one or more implantable devices 200/800); and combinations of one or more of these. In some embodiments, the temperature sensor-based functional element 299/599/899 is a part of a safety mechanism that deactivates programmer 550, external device 500, and/or implantable device 200/800 if the recorded temperature exceeds a threshold. Alternatively or additionally, a temperature sensor-based functional element 299/599/899 can be configured to measure temperature of the patient, such as when placed on housing 551/510, housing 210 and/or housing 810 (singly or collectively housing 210/810), such as to adjust energy delivery performed by implantable device 200/800 based on the recorded patient temperature.

In some embodiments, implantable system 20 comprises multiple implantable devices 200, and implantable system 20 comprises a "multi-point ready" system in which the operation (e.g. energy delivery, data recording and/or other function) of the multiple implantable devices 200 is performed simultaneously, asynchronously, and/or sequentially. The implantable devices 200 can be part of a network including one or more external devices 500 in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single or multiple external devices 500, which can further be synchronized to a single clock. Each implantable device 200 of implantable system 20 can receive a power signal and/or a data signal from one or more external devices 500. In some embodiments of the multi-point ready implantable system 20, each implantable device 200 comprises a unique ID, such that each implantable device 200 can be individually addressed (e.g. receive unique signals from external system 50). In some embodiments, external system 50 transmits high-bandwidth signals to implantable system 20, such that time-domain multiple access communication can be performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200.

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

In some embodiments, one or more implantable devices 200/800 are further configured to transmit data to programmer 550 and/or one or more external devices 500, such as via one or more antennas 240/840 transmitting a signal to one or more antennas 540. Data transmitted by an implantable device 200/800 can comprise patient information (e.g. patient physiologic information recorded by one or more stimulation elements 260 or functional elements 299/599/899 configured as a physiologic sensor), or implantable device 200/800 information (e.g. data recorded by one or more sensors positioned in implantable device 200/800, or other implantable device 200/800 configuration and/or performance data).

Housing 210/810 of each implantable device 200/800, can comprise one or more rigid and/or flexible materials. Housing 210 can surround various components of implantable device 200, such as antenna 240, energy storage assembly 270, controller 250 and/or receiver 230. Housing 810 can surround various components of implantable device 800, such as antenna 840, energy storage assembly 870, controller 850 and/or receiver 830. In some embodiments, one or more stimulation elements 260 are positioned in, on and/or within housing 210/810. In some embodiments, housing 210/810 surrounds a substrate, such as a flexible and/or foldable printed circuit board, such as multiple discrete or continuous printed circuit boards positioned in different planes (e.g. a flexible or foldable printed circuit board).

Housing 210/810 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210/810 can comprise a major axis and a minor axis, as defined hereabove. In some embodiments, housing 210/810 comprises a major axis less than or equal to 20 mm, such as a major axis less than or equal to 15 mm, 12 mm or 10 mm. In some embodiments, housing 210/810 comprises a minor axis less than or equal to 8 mm, such as a minor axis less than or equal to 6 mm, or less than or equal to 5 mm Housing 210/810 can comprise a wall thickness between 0.1 mm and 1.0 mm, such as a wall thickness between 0.2 mm and 0.5 mm, such as a wall thickness of approximately 0.3 mm Housing 210/810 can comprise a displacement volume less than or equal to 2000 $mm^3$, such as less than or equal to 600 $mm^3$.

Housing 210/810 can comprise one or more portions that are transmissive to radiofrequency (RF) signals. In some embodiments, housing 210/810 comprises glass. In some embodiments, housing 210/810 comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations of one or more of these. In some embodiments, one or more portions of housing 210/810 comprises one or more coatings, such as one or more coatings configured to cause or prevent a physiologic reaction and/or a coating configured to block (e.g. shield) an electromagnetic transmission.

Housing 210/810 can comprise one or more passageways or other feedthroughs, such as for the passage of a lead, wire, optical fiber, fluid delivery tube, mechanical linkage and/or other conduit through a wall of housing 210/810, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes. In some embodiments, housing 210 comprises an array of feedthroughs. In some embodiments, housing 210/810 is surrounded by a covering, such as a flexible and/or non-conductive covering, such as a covering made of an elastomer.

In some embodiments, one or more implantable devices 200/800 comprises one or more anchor elements configured to secure one or more portions of implantable device 200/800 to tissue. The one or more anchor elements can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

One or more antennas 240/840 can be configured to receive power and/or data, and receiver 230 and/or receiver 830 (singly or collectively receiver 230/830) can receive the power and/or data from the one or more antennas 240/840, respectively. Each antenna 240/840 can comprise one or more implantable antennas, such as one or more antennas positioned within housing 210/810, and/or one or more antennas electrically attached to a connecting filament. In some embodiments, one or more implantable devices 200/800 comprise at least two antennas 240/840, or at least three antennas 240/840. Antenna 240/840 can be configured to receive power and/or data from one or more external devices 500 and/or programmer 550, such that an attached receiver 230/830 receives the power and/or data. In some embodiments, receiver 830 is not configured to receive power, simply data. In some embodiments, implantable system 20 comprises at least two implantable devices 200/800, each of which comprise one or more (e.g. two or three) antennas 240/840 which are positioned within a housing 210/810 and/or electrically tethered to a housing 210/810. In some embodiments, an implantable device 200/800 comprises a first antenna 240/840 positioned in a first plane and a second antenna 240/840 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200/800 comprises a first antenna 240/840 positioned in a first plane, a second antenna 240/840 positioned in a second plane, and a third antenna 240/840 positioned in a third plane.

In some embodiments, implantable device 200/800 comprises one or more antennas 240/840 positioned on a substrate, such as a printed circuit board (PCB), a flexible printed circuit board and/or a foldable substrate (e.g. a substrate comprising rigid portions and hinged portions). In some embodiments, the substrate can be folded or otherwise pivoted to position the various antennas 240/840 on differently oriented planes, such as multiple planes oriented between 5° and 90° relative to each other, such as two antennas 240/840 positioned on two planes oriented between 30° and 90° or between 40° and 90° relative to each other, or three antennas 240/840 positioned on three planes oriented between 5° and 60° relative to each other. Two or more antennas 240/840 can be positioned on two or more different planes that are approximately 45° relative to each other, or approximately 60° or approximately 90° relative to each other.

Implantable device 200/800 can comprise three antennas 240/840. In some embodiments, a first antenna 240/840 can comprise an electrical dipole antenna, and the second and third antennas 240/840 can be positioned in different planes than the first antenna 240/840. In some embodiments, the three antennas 240/840 each comprise a loop antenna, such as when each loop antenna is positioned on a different plane. In some embodiments, a first antenna 240/840 comprises an electrical dipole antenna, and a second antenna 240/840 and a third antenna 240/840 each comprise a loop antenna. In these embodiments, the second antenna 240/840 and the third antenna 240/840 can be positioned relatively orthogonal to each other (e.g. positioned on two relatively orthogonal planes). In some embodiments, a first antenna 240/840 (e.g. an electrical dipole antenna) is positioned outside of housing 210/810, while a second antenna 240/840 (e.g. a loop antenna) and a third antenna 240/840 (e.g. a loop antenna) are each positioned on, in and/or within housing 210/810. In some embodiments, implantable device 200/800 can comprise one or more antennas 240/840 in which any combination of antenna types (as described herein) are used in combination.

One or more antennas 240/840 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240/840 can comprise a loop antenna, such as an elongated loop antenna or a multiple-turn loop antenna.

One or more antennas 240/840 can comprise a multi-turn spiral loop antenna, such as a multi-turn spiral loop antenna configured to desensitize coupling sensitivity and/or boost input voltage. In some embodiments, one or more antennas 240/840 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

One or more antennas 240/840 can comprise a minor axis and a major axis. In some embodiments, one or more antennas 240/840 comprise a minor axis between 1 mm and 8 mm, such as between 2 mm and 5 mm. In some embodiments, one or more antennas 240/840 comprise a major axis between 3 mm and 15 mm, such as between 4 mm and 8 mm. In some embodiments, one or more antennas 240/840 comprise a major axis above 3 mm, such as between 3 mm and 15 mm, such as when the antenna 240/840 is positioned outside of housing 210/810.

One or more antennas 240/840 can comprise a foldable and/or unfoldable antenna, such as is described in applicant's co-pending U.S. patent application Ser. No. 14/975,358, titled "Method and Apparatus for Minimally Invasive Implantable Modulators", filed Dec. 18, 2015, the content of which is incorporated herein by reference in its entirety for all purposes.

One or more antennas 240/840 can be positioned inside of housing 210/810. Alternatively or additionally, one or more antennas 240/840 can be positioned outside of housing 210/810.

Implantable system 20, one or more implantable devices 200/800 and/or one or more antennas 240/840 can be configured to be positioned at a desired depth beneath the patient's skin, such as at a depth between 0.5 cm and 7.0 cm, such as a depth of between 1.0 cm and 3.0 cm. In some embodiments, one or more antennas 840 are positioned at a deeper implant location than the depth at which one or more antennas 240 are implanted.

One or more energy storage assemblies 270 and/or 870 (singly or collectively energy storage assembly 270/870) can comprise one or more implantable energy storage components, such as one or more batteries (e.g. rechargeable batteries) and/or capacitors (e.g. a supercapacitor). Energy storage assembly 270/870 can be configured to provide power to one or more of: one or more stimulation elements 260; controller 250/850; receiver 230/830; and combinations of one or more of these. In some embodiments, energy storage assembly 270/870 further provides power to one or more antennas 240/840 and/or circuitry configured to transmit data via antenna 240/840. In some embodiments, energy storage assembly 270/870 includes digital control for charge/discharge rates, voltage outputs, current outputs, and/or system power distribution and/or management.

Energy storage assembly 270/870 can comprise one or more capacitors with a single or collective capacitance between 0.01 µF and 10F, such as a capacitance between 1 µF and 1.0 mF, or between 1 µF and 10 µF. Energy storage assembly 270/870 can comprise one or more capacitors with a capacitance between 1 mF and 10 F, such as when energy storage assembly 270/870 comprises a super-capacitor and/or an ultra-capacitor. Such large capacitance can be used to store sufficient charge to maintain operation (e.g. maintain delivery of stimulation energy and/or delivery of an agent) without the use (e.g. sufficient proximity) of an associated power-providing external device 500. A capacitor or other energy storage element (e.g. a battery) can be chosen to provide sufficient energy to maintain operation for at least 30 seconds, at least 2 minutes, at least 5 minutes, at least 30 minutes, and/or up to several hours or more (e.g. during showering, swimming or other physical activity). In some embodiments, energy storage assembly 270/870 is configured to provide continuous and/or intermittent stimulation energy for at least one charge-balanced pulse (e.g. for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year (e.g. when implantable device 800 is configured to provide long term stimulation without externally received power). Energy storage assembly 270/870 can comprise one or more capacitors with a breakdown voltage above 1.0V, such as a breakdown voltage above 1.5V, 4.0V, 10V, or 15V. In some embodiments, energy storage assembly 270/870 can comprise capacitors distributed outside of housing 210/810, such as when one or more capacitors are distributed along lead 265. Energy storage assembly 270/870 can comprise one or more capacitors with low self-leakage, such as to maintain stored energy for longer periods of time.

In some embodiments, energy storage assembly 270/870, particularly energy storage assembly 270, comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 sending power to an implantable device 200 that is not in place, such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more stimulation elements 260 to deliver stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

In some embodiments, implantable device 200 receives power regularly from external system 20 (e.g. relatively continuously while implantable device 200 delivers stimulation energy), and energy storage assembly 270 comprises a relatively small battery or capacitor, such as a battery or capacitor that has an energy storage capacity of less than or equal to 0.6 Joules, 7 Joules or 40 Joules. In these embodiments, implantable device 800 can receive no or minimal power regularly from external system 20 (e.g. stimulation energy delivered by implantable device 800 is provided by energy storage assembly 870), and energy storage assembly 870 comprises a larger battery or capacitor than energy storage assembly 270. For example, energy storage assembly 870 can be configured to store at least 10 times the power stored in energy storage assembly 270, or at least 100 times or 500 times the power stored in energy storage assembly 270. In some embodiments, energy storage assembly 870 has a capacity of at least 60 Joules, 700 Joules, or 4,000 Joules.

One or more controllers 250 and/or 850 (singly or collectively controller 250/850) can be configured to control one or more stimulation elements 260, such as a stimulation element 260 comprising an energy-delivering transducer (e.g. an electrode or other energy delivery element) and/or a sensor (e.g. a physiologic sensor and/or a sensor configured to monitor an implantable device 200/800 parameter). In some embodiments, controller 250/850 is configured to transmit a stimulation signal (e.g. transmit stimulation energy configured in one or more stimulation waveforms) to one or more stimulation elements 260 (e.g. one or more stimulation elements 260 comprising an electrode and/or other energy delivery element), independent of the power signal received by one or more antennas 240/840 (e.g. independent of power transmitted by external system 50), such as by using energy stored in energy storage assembly 270/870. In these embodiments, the power signal and/or the RF path for the power signal can be adjusted to optimize power efficiency (e.g. by tuning matching network on transmitter 530 and/or receiver 230/830; configuring antennas 540 and/or 240/840 in an array; tuning operating frequency; duty cycling the power signal; adjusting antenna 540 and/or 240/840 position; and the like), and a stimulation signal can be precisely delivered (e.g. by using energy stored on energy storage assembly 270/870 and generating a stimulation signal locally on the implantable device 200/800) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200/800 can be insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250/850 can receive commands from receiver 230/830, such as one or more commands related to one or more implantable device 200/800 configuration parameters selected from the group consisting of: stimulation parameter; data rate of receiver; data rate of data transmitted by implantable antenna 240/840; stimulation element 260 configuration; state of controller 250/850; antenna 240/840 impedance; clock frequency; sensor configuration; electrode configuration; power management parameter; energy storage assembly parameter; agent delivery parameter; sensor configuration parameter; and combinations of one or more of these.

In some embodiments, one or more stimulation elements 260 comprise a stimulation element configured to deliver energy (e.g. one or more electrodes configured to deliver monopolar or bipolar electrical energy) to tissue, and controller 250/850 is configured to control the energy delivery, such as to control one or more stimulation parameters as described herein. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described in applicant's co-pending International PCT Patent Application Serial Number PCT/US2017/017978, titled "Apparatus with Enhanced Stimulation Waveforms", filed Feb. 15, 2017, the content of which is incorporated herein by reference in its entirety for all purposes. In some embodiments, stimulation (e.g. stimulation comprising high frequency and/or low frequency signal components) is varied randomly to eliminate or at least reduce synchrony of neuronal firing with the stimulation signal (e.g. to reduce paresthesia or other patient discomfort). In some embodiments, one or more stimulation elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: stimulation element 260 size and/or configuration (e.g. electrode size and/or configuration); stimulation element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more stimulation elements 260 comprise an element configured to deliver electrical energy to tissue (e.g. one or more electrodes configured to deliver monopolar or bipolar electrical energy), and controller 250/850 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.01 mA and 12 mA, or between 0.01 mA and 10 mA), depending on the treatment, the error in charge balance can be on the order of 0.001% to 0.01%. Alternatively or additionally, controller 250/850 can comprise AC coupling capacitors that are configured to balance stimulation waveforms passively. The AC coupling capacitance can be fairly large (e.g. greater than 10 µF), in order to pass the stimulation waveform with minimal filtering. In some embodiments, apparatus 10 can be configured to perform active charge balancing. In some embodiments, an implantable device 200/800 can comprise a precise resistor in series with a stimulation electrode-based stimulation element 260. The precise resistor can be used to measure outflow and inflow currents, such as when controller 250/850 comprises an analog to digital converter (ADC). Controller 250/850 can integrate current over time during a first phase in which stimulation energy is delivered, and during a second phase in which a reverse current is applied (e.g. a reverse current used to balance charge). Controller 250/850 can be configured to balance the total charge in the two phases, to ensure that the net DC current is approximately zero. The integration can be achieved using an analog integrator and/or a digital summer of controller 250/850, with controller 250/850 keeping track of one or more parameters of the pulses delivered (e.g. pulses delivered within a train or a burst). Implantable device 200/800 can comprise a precise series resistance comprising an on-chip trimmed resistor or an off chip resistor. In some embodiments, implantable device 200/800 comprises a bank of trimmed resistors that are used to control the net series resistance, such as to adjust resistance based on stimulation amplitude requirements (e.g. to take advantage of the full dynamic range of an ADC of controller 250/850). In some embodiments, controller 250/850 comprises a shunt path with an RC-based low pass filter used for both outflow and inflow of current. RC elements of controller 250/850 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250/850 keeps track of the number of times the capacitor has been charged and reset. By resetting the capacitor through a low resistance path, the discharge time can be insignificant compared to the charge time, reducing the error due to the discharge period. Since the net charge equivalent to full scale voltage on the ADC can be divided into multiple cycles, the required resolution of the ADC to achieve the same residual error can be divided by the number of cycles.

In some embodiments, controller 250/850 is configured to produce a stimulation signal comprising a waveform or a waveform pattern (hereinafter stimulation waveform), for one or more stimulation elements 260 configured as a stimulation element (e.g. such that one or more stimulation elements 260 deliver stimulation energy comprising or at least resembling that stimulation waveform). Controller 250/850 can produce a stimulation signal comprising a waveform selected from the group consisting of: square wave; rectangle wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250/850 is configured to produce a stimulation signal comprising a waveform including a combination of two or more waveforms selected from the group consisting of: square wave; rectangle wave; sine wave; triangle wave (symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250/850 is configured to construct a custom waveform (e.g. an operator customized waveform), such as by adjusting amplitude at specified time steps (e.g. for one or more pulses). In some embodiments, controller 250/850 is configured to generate a waveform including one or more random parameters (e.g. random timing of pulses or random changes in frequency, rate of change or amplitude).

In some embodiments, controller 250/850 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250/850 is configured to produce a stimulation signal comprising a frequency between 1 Hz and 1000 Hz, such as a stimulation signal with a frequency between 10 Hz and 500 Hz. In some embodiments, controller 250/850 is configured to produce a stimulation signal comprising a duty cycle between 0.1% and 99%, such as a duty cycle between 1% and 10% or between 1% and 25%. In some embodiments, controller 250/850 is configured to produce a stimulation signal comprising a frequency modulated stimulation waveform, such as a stimulation waveform comprising a frequency component (e.g. signal) between 1 kHz and 20 kHz. In some embodiments, controller 250/850 is configured to produce a stimulation signal comprising a mix and/or modulation of low frequency and high frequency signals, which can be of any of the waveform types, shapes and other configurations as described herein. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250/850 can comprise a clamping circuit configured to allow fast charging and/or discharging of the energy storage assembly 270/870, stimulation element 260 drivers (e.g. electrode drivers) of controller 250/850, and/or other components of implantable device 200/800. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 µs rise and/or fall time for a 10 µs stimulation pulse).

In some embodiments, controller 250/850 comprises a matching network configured to match the impedance of a first antenna 240/840 with the impedance of the receiver 230/830. In these embodiments, controller 250/850's matching network can be adjustable. Alternatively or additionally, controller 250/850 can comprise an adjustable loading impedance to stabilize the load seen at an antenna 240/840 under different operating conditions. In some embodiments, the adjustable loading impedance is controlled according to the charge rate of the energy storage assembly 270/870.

Controller 250/850 and/or any other component of each implantable device 200/800 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230/830 can each comprise one or more components, such as a demodulator, a rectifier and/or a power converter. In some embodiments, receiver 230/830 can comprise a DC-DC converter such as a boost converter. Receiver 230/830 can comprise a data receiver, such as a data receiver including an envelope detector and demodulator and/or an envelope averaging circuit. In some embodiments, one more antennas 240/840 separately connect to one or more receivers 230/830. In some embodiments, one or more antennas 240/840 connect to a single receiver 230/830, such as via a series connection or a parallel connection.

One or more implantable devices 200/800 can be configured to transmit a data signal to external system 50. In some embodiments, receiver 230/830 is configured to drive one or more antennas 240/840 to transmit data to external system 50 (e.g. to an antenna 540a of programmer 550 or antenna 540b of an external device 500). Alternatively or additionally, implantable device 200/800 can be configured to transmit a data signal by having receiver 230/830 adjust a load impedance to backscatter energy, such as a backscattering of energy which can be detected by external system 50. In some embodiments, data transmission is accomplished by receiver 230/830 manipulating a signal at a tissue interface, such as to transmit a data signal using body conduction.

In some embodiments, receiver 230/830 comprises a matching network, such as a matching network configured to detune to prevent oversaturation. For example, implantable system 20 can comprise two or more implantable devices 200/800, and each of which can include a receiver 230/830 comprising a matching network. A first implantable device 200/800's receiver 230/830's matching network can be configured to detune based on power received by the second implantable device 200/800's receiver 230/830.

A demodulator portion of receiver 230/830 can comprise circuitry that asynchronously recovers signals modulated on the power signal provided by external system 50, and converts the modulated signals into digital signals. In some embodiments, the demodulator asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, the demodulator recovers a digital signal that can be used as timing information for an implantable device 200/800, similar to an on-chip clock. The recovered clock signal can also be used to synchronize an on-chip clock generator of controller 250/850, such as through the use of a frequency and/or phase locked loop (FLL or PLL).

A rectifier portion of receiver 230/830 can comprise a power signal rectifier, such as to provide power to the energy storage assembly 270/870 and/or controller 250/850. In some embodiments, the rectifier comprises one or more self-driven synchronous rectifier (SDSR) stages connected in charge-pump configuration, to boost the voltage from an input RF amplitude to the rectifier, to a higher voltage. The boosted voltage can directly charge energy storage assembly 270/870, or be further boosted by a DC-DC converter or boost converter. In some embodiments, the rectifier can comprise diode-capacitor ladder stages instead of, or in addition to, SDSR stages. On-chip diodes, such as Schottky diodes, or off-chip diodes can be used in one or more rectifier stages. For maximum efficiency, the rectification elements, such as diodes, can be optimized to minimize forward conduction and/or reverse conduction losses by properly sizing the components and selecting appropriate number of stages based on the input RF voltage and load current.

A power converter portion of receiver 230/830 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters can interface with energy storage assembly 270/870 and charge up associated energy storage components to desired voltages. In some embodiments, a power converter receives control signals from controller 250/850, such as to configure voltages, currents, charge/discharge rates, switching frequencies, and/or other operating parameters of the power converter.

One or more implantable leads 265 (singly or collectively lead 265) can be attached to one or more housings 210/810, such as at attachment port 290 of implantable device 200 and/or attachment port 890 of implantable device 800. In some embodiments, various components of implantable system 20 are implanted in multiple clinical procedures, such as is described herebelow in reference to FIG. 2. For example, implantable device 200 can be implanted in a first clinical procedure in which lead 265 is also implanted. In this first clinical procedure, lead 265 is operably attached to implantable device 200 via attachment port 290. After the first clinical procedure, a "trial period" ensues in which stimulation is provided in order to evaluate use of apparatus 10 to provide therapy to the patient. During the trial period, stimulation settings can be varied (e.g. variations of: stimulation element 260 positions, configurations and/or combinations; stimulation frequencies; stimulation waveform shapes; and/or stimulation pulse width and/or amplitude). Today's clinical practice can include use of an external stimulator during an evaluation period (e.g. similar to the "trial period" described herein) of a future implanted stimulator, such as an external stimulator that attaches to an implanted lead (e.g. a lead similar to lead 265), via a transcutaneous conduit. This external stimulator approach during the evaluation period has numerous disadvantages including risk of infection, which limits the duration of the evaluation period. Apparatus 10 of the present inventive concepts includes implantable stimulator 200, which is implanted in the patient for use in the trial period, avoiding any transcutaneous conduits. Use of the implanted stimulator of the present inventive concepts during an evaluation phase can provide numerous advantages, including but not limited to extended length of the trial period (e.g. due to the decreased risk of infection of a fully implanted device), such as a trial period that lasts at least 1 week, at least 2 weeks, at least 1 month, at least 2 months, and/or at least 3 months, greatly reduced risk of dislocating the implanted lead (e.g. a dislocation which could occur with inadvertent tugging on a transcutaneous conduit), simplification of patient bathing (e.g. due to avoidance of transcutaneous conduit), and/or improved patient experience with apparatus (since long term device similarly does not include transcutaneous conduit). Use of implantable stimulator 200 versus an external simulator, during a trialing period as described herein, provides the patient with a similar experience to that which will be encountered with implantable stimulator 800 (e.g. since both are implanted). During the trialing period, implantable device 200 receives power and data from one or more external devices 500, as is described herein, avoiding the need for a large capacity energy storage assembly 270 (e.g. reducing the volume of implantable device 200). After the trialing period, in a second clinical procedure, implantable device 200 is detached from lead 265, and implantable device 800 is attached to lead 265 and implanted in the patient (in any order). After implantation, implantable device 800 provides long-term therapy to the patient for a therapy period (e.g. a period of at least 1 month, at least 6 months, at least 1 year or at least 2 years). During the therapy period, implantable device 800 may not receive any power from external system 50, such as when energy storage assembly 870 comprises a capacity sufficient to deliver stimulation for the entire therapy period. In alternative embodiments, energy storage assembly 870 is recharged periodically (e.g. not continuously), such as via a wireless recharge (e.g. via a RF or other wireless transmitter, magnetic coupling, inductive coupling, capacitive coupling and/or other wireless power transmission means).

Lead 265 comprises proximal portion 268, distal portion 269, and a shaft (e.g. a flexible shaft), shaft 261. Lead 265 comprises at least one stimulation element 260, such as two, three, four or more stimulation elements (three shown positioned on distal portion 269 in FIG. 1). Stimulation elements 260 can comprise electrodes or other energy delivering elements. Stimulation element 260 can comprise two or more electrodes configured to deliver energy in monopolar or bipolar energy delivery modes. In some embodiments, one or more stimulation elements 260 and/or other component of implantable device 200/800 (e.g. functional elements 299 and/or 899) can be configured as a physiologic sensor (e.g. an electrode configured to record electrical activity of tissue or other physiologic sensor as described herein). One or more stimulation elements 260 can be configured to transmit signals through tissue to one or more components of external system 50, such as through body conduction.

Stimulation elements 260 are operatively connected (e.g. electrically, optically, and/or acoustically connected) to contacts 262 via conduit 263 (e.g. one or more wires, optical fibers, wave guides, and the like). Contacts 262, shown positioned on proximal portion 268 of lead 265, are constructed and arranged to operatively connect to contacts 292 of attachment port 290 (e.g. in a first clinical procedure), and contacts 892 of attachment port 890 (e.g. in a subsequent, second clinical procedure). Contacts 292 and/or 892 (contacts 292/892 herein) are operatively connected with various components of implantable device 200/800 such that stimulation energy can be provided by implantable device 200/800 to stimulation elements 260 via attachment port 290/890 and conduit 263.

In some embodiments, lead 265 comprises a removable stylet configured to aid in the implantation of lead 265, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes. In some embodiments, implantable system 20 comprises more than one lead 265, each comprising one or more stimulation elements 260 and attached to one or more attachment ports 290/890 of one or more implantable devices 200/800.

In some embodiments, lead 265 comprises a diameter between 1 mm and 4 mm, such as a diameter between 1 mm and 2 mm. In some embodiments, lead 265 comprises a length between 3 cm and 60 cm, such as a length between 6 cm and 30 cm. One or more leads 265 can include between 2-64 stimulation elements 260, such as when a lead 265 comprises between 2 and 64 electrodes, such as between 4 and 32 electrodes. In some embodiments, lead 265 comprises a paddle lead. In some embodiments, stimulation element 260 comprises one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, stimulation element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the knee, the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ;

the heart; the liver; the kidney; an artery; a vein; bone; and combinations of one or more of these, such as to stimulate and/or record data from the tissue and/or location in which the stimulation element 260 is positioned proximate to and/or within. In some embodiments, apparatus 10, implantable device 200, implantable device 800, and/or stimulation element 260 are configured to stimulate spinal nerves, peripheral nerves and/or other tissue as described in applicant's co-pending application International PCT Patent Serial Number PCT/US2016/051177, titled "Apparatus for Peripheral or Spinal Stimulation", filed Sep. 9, 2016.

In some embodiments, stimulation element 260 or a component of implantable device 200/800 comprises one or more sensors configured to record data representing a physiologic parameter of the patient. Stimulation element 260 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor; bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 and stimulation element 260 can be configured to record a patient parameter (e.g. patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, apparatus 10 comprises tool 60. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 557 and/or 570 comprising a rechargeable battery or capacitor.

In some embodiments, tool 60 comprises an implantation tool, such as an introducer or other implantation tool constructed and arranged to aid in the implantation of housing 210, housing 810, implantable antenna 240, implantable antenna 840, lead 265 and/or one or more stimulation elements 260.

In some embodiments, lead 265 comprises a paddle lead or other stimulating lead and tool 60 comprises an introducer (e.g. a needle or an extended-width introducer) configured to deliver at least a distal portion of lead 265 into an epidural space of a patient. Tool 60 can comprise an introducer comprising a Tuohy needle, such as a Tuohy needle of 12 gauge or smaller. Tool 60 can comprise a handle for manipulating lead 265. Tool 60 can be configured to place lead 265 at an entry point above the lumbar spinal column (e.g. between L1 and L2 vertebrae). Tool 60 can include extension tubing used to insert lead 265. Tool 60 can further comprise a tool configured to anchor lead 265, such as when tool 60 comprises sutures, clips, other anchoring elements and/or an anchor securing tool (e.g. a needle or a stapling device), such as to secure lead 265 in subcutaneous tissue. Lead 265 and/or tool 60 can comprise extension tubing used to place lead 265, such as extension tubing that remains in place after removal of an introducer of tool 60. Tool 60 can be configured to place lead 265 against the dura of the spinal cord of the patient.

In some embodiments, tool 60 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can be placed via tool 60 such that one or more stimulation elements 260 (e.g. electrodes) are positioned within the multifidus muscle structures. One or more stimulation elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Stimulation elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, stimulation elements 260 are positioned to cause transvascular stimulation (e.g. transvascular stimulation from arteries and/or veins in a leg or arm). In some embodiments, stimulation elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, stimulation elements 260 are configured to deliver stimulation energy to contract the multifidus muscle. In some embodiments, stimulation elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool 60 comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g. an RF transmitter), magnetic coupling, inductive coupling, capacitive coupling and/or other wireless transmission means.

Apparatus 10 can include one or more devices, such as patient attachment device 70 shown in FIG. 1, that is used to attach one or more portions of external system 50 to a location on or proximate the patient. In some embodiments, patient attachment device 70 is constructed and arranged as described in applicant's co-pending U.S. patent application Ser. No. 15/385,729, titled "Method and Apparatus for Neuromodulation Treatments of Pain and Other Conditions", filed Dec. 20, 2016.

Patient attachment device 70 can comprise one or more elements configured to attach one or more external devices 500 and/or programmer 550 at one or more locations on or proximate the patient's skin, that are relatively close to one or more implantable devices 200/800 that have been implanted in the patient. Patient attachment device 70 can comprise a component selected from the group consisting of: belt; belt with pockets; belt with adhesive; adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540a and/or 540b mounted to or otherwise positioned on a printed circuit board such as a flexible printed circuit board). Patient attachment device 70 can include one or more pockets, such as one or more pockets configured to collectively surround one or more of: external device 500; programmer 550; one or more antennas 540; power supply 570; power supply 557; and combinations of one or more of these. In some embodiments, patient attachment device 70 comprises multiple pockets, such as to allow repositioning of an external antenna 540, programmer 550, external transmitter 530, power supply 570, and/or power supply 557 to various different locations, such as to improve transmission of power and/or data to one or more implantable devices 200/800 and/or to improve patient comfort. In some embodiments, one or more antennas 540, power supplies 570, power supplies 557, transmitters 530, and/or transmitters 553 are connected through flexible cables positioned in patient attachment device 70. In some embodiments, the flexible cables are small coax cables that can accommodate the power levels and frequencies of the carried signals. In some embodiments, the one or more antennas 540 are connected to one or more additional components of external device 500 and/or programmer 550 through a single cable with a local power splitting component and/or active matching element that adjusts signal power to each of the one or more antennas 540.

In some embodiments, one or more implantable devices 200/800 of implantable system 20 can comprise an implantable transmitter configured to transmit data, such as to transmit data (e.g. stimulation information, patient physiologic information, patient environment information, implantable device 200/800 performance and/or configuration information, and the like) to one or more external devices 500 and/or programmer 550. In these embodiments, receiver 230/830 can be configured as both a receiver and a transmitter. One or more implantable devices 200/800 can be configured to transmit data by sending a signal to (i.e. "driving") one or more antennas 240/840 or another antenna of implantable device 200/800. An implantable device 200/800 can be configured to transmit data using one or more of: load modulation; a signal carrier; and/or body conduction. An implantable device 200/800 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 91 shown in FIG. 1. In some embodiments, programmer 550 and/or implantable controller 250/850 comprise all or a portion of diagnostic assembly 91. Diagnostic assembly 91 can be configured to assess, monitor, determine and/or otherwise analyze patient information and/or implantable device 200/800 information, such as when one or more stimulation elements 260 or functional elements 299/599/899 are configured as a sensor that records patient information (e.g. patient physiologic information and/or patient environment information) and/or apparatus 10 information (e.g. implantable device 200/800 information) as described herein. Diagnostic assembly 91 can be configured to analyze communication and/or the power link between an implantable device 200/800 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the controller 250/850 or programmer 550, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270/870. Similar to the communication link, the power link status and/or trending can be monitored and recorded for link adjustment and/or feedback purposes. Diagnostic assembly 91 can be configured to analyze a result of stimulation energy delivered by implantable device 200/800, such as when a stimulation element 260 comprises an electrode to record electrical activity of tissue (e.g. in addition to delivering electrical energy to stimulate tissue). A stimulation element 260 and/or functional element 299/599/899 can comprise a sensor configured to record neural activity and/or muscular activity, and diagnostic assembly 91 can be configured to analyze the recorded sensor data. In some embodiments, diagnostic assembly 91 can be configured to analyze impedance, such as when a stimulation element 260 and/or a functional element 299/599/899 comprises a sensor configured to record data related to impedance, such as when implantable device 200/800 performs a frequency sweep, performs an impulse response and/or compares voltage and current of a stimulation waveform. In some embodiments, diagnostic assembly 91 is configured to assess the impedance of one or more implantable antennas 240/840 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 91 is configured to test or otherwise assess the link between one or more implantable antennas 240/840 and one or more external antennas 540 (e.g. during a procedure in which one or more implantable devices 200/800 are implanted in a patient). In these embodiments, diagnostic assembly 91 can be configured to perform a test prior to anchoring housing 210/810 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210/810 in its implant location, diagnostic assembly 91 can be configured to confirm that one or more external antenna 540 transmission links to one or more implantable antennas 240/840 are above an efficiency threshold, for example such that sufficient power will be received by the one or more implantable devices 200/800. Additionally, the procedure can be performed to optimize or otherwise improve the position of the one or more implantable devices 200/800 to be implanted and subsequently secured to tissue.

In these link testing embodiments, diagnostic assembly 91 can comprise a handheld assembly (e.g. a sterile assembly comprising a wand or other handheld housing). Diagnostic assembly 91 can be configured to send a simple signal to one or more implantable devices 200/800 (e.g. a diagnostic assembly 91 with similar power and/or data transmission capabilities as an external device 500). Each implantable device 200/800 can respond (e.g. via data sent via an implantable antenna 240/840 or other transmitter) with information related to the quality of the transmission link (e.g. information about the power received by the one or more implantable devices 200/800). Diagnostic assembly 91 could provide a user interface (e.g. a speaker, a text screen and/or a video display) that provides quality or other information (go/no go information, digital or other discrete level information, and/or analog information). Diagnostic assembly 91 could be further configured to provide information confirming detection of one or more implantable devices 200/800, status of one or more implantable devices 200/800 (e.g. parameter level and/or fault detection status), and/or self-diagnostic status (i.e. diagnostic assembly 91 status).

Each implantable device 200/800 can be configured to specifically identify and/or specifically reply to diagnostic assembly 91 (e.g. in a different form than communications with an external device 500). Each implantable device 200/800 can be configured to provide information related to one or more of: the charge and/or discharge rate of energy storage assembly 270/870 (e.g. the charge and/or discharge rate of a capacitor or battery of energy storage assembly 270/870); or the frequency of a voltage-controlled oscillator that is driven by an unregulated voltage of a power converter of receiver 230/830. Diagnostic assembly 91 can be configured to perform numerous performance tests (e.g. of one or more implantable devices 200/800 or implantation locations for one or more implantable devices 200/800), prior to completion of the implantation procedure (e.g. prior to closing one or more incisions).

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200/800, via one or more of its stimulation elements 260 (e.g. electrodes) can be configured to provide localized (e.g. targeted) magnetic and/or electrical stimulation. Combined electrical field stimulation and magnetic field stimulation can be applied by using superposition, and can reduce the overall energy requirement. In some embodiments, implantable apparatus 10 comprises one or more stimulation elements 260 comprising a magnetic field generating transducer (e.g. microcoils or cuff electrodes positioned to partially surround or otherwise be proximate to one or more target nerves). Stimulation elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises dorsal root ganglia (DRG) tissue, and the non-target tissue comprises ventral root tissue (e.g. when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240/840 can degrade over time due to physical misalignment of the antennas, relative orientation change between antennas and/or relative angular misalignment between antennas. In order to compensate for misaligned antennas, electrical beam steering can be included in apparatus 10. Antennas comprising a multi-feed antenna structure and/or an array of antennas can be incorporated (e.g. into external antenna 540, implantable antenna 240/840 or both) for electrical beam steering. Alternatively or additionally, mechanical antenna steering can be implemented to physically realign one or more external antennas 540 with one or more implanted antennas 240/840 (or vice versa). A substrate of an implantable antenna 240/840 and/or an external antenna 540 can be flexible and/or rigid (e.g. a substrate comprising polyamide, polyimide, liquid crystal polymer (LCP), Rogers, FR4, or a similar material). One or more antennas 540 can be connected to electronics (e.g. a transmitter, receiver or transceiver) using a flexible waveguide or cable (e.g. 50 ohm 0.047" coaxial cable designed to provide patient comfort) and/or a flexible PCB substrate transmission line. Mechanical or physical realignment of antennas 240/840 and/or 540 can be accomplished using one or more of: use of motorized positioners, such as a mechanism including one or more small pulleys and/or tensioners used to translate one or more antennas 240/840 and/or 540 about one or more axes; an actuator (e.g. a piezoelectric actuator) with directional gears configured to translate one or more antennas 240/840 and/or 540 about one or more axes; a micro-pump with fluid reservoir (e.g. liquid or gas reservoir) configured to hydraulically and/or pneumatically translate one or more antennas 240/840 and/or 540 about one or more axes, such as by creating a local pressure difference. In some embodiments, a micro-pump with fluid reservoir can be used to move one or more antennas 240/840 and/or 540, such as to move an external antenna 540 away from tissue to reduce specific absorption rate (SAR). In these embodiments, external antenna 540 can be positioned in mechanical contact with an expandable reservoir (e.g. a balloon) positioned between external antenna 540 and tissue. The reservoir can be inflated or deflated to control separation distance of the external antenna 540 from the patient's skin surface. In some embodiments, apparatus 10 comprises one or more algorithm positioning algorithms, beam steering functionality and/or mechanical antenna steering as described in applicant's co-pending U.S. patent application Ser. No. 14/975,358, titled "Method and Apparatus for Minimally Invasive Implantable Modulators", filed Dec. 18, 2015, or International PCT Patent Application Serial Number PCT/US2016/016888, titled "Medical Apparatus including an Implantable System and an External System", filed Feb. 5, 2016, the content of each of which is incorporated herein in its entirety for all purposes.

In some embodiments, implantable system 20 of apparatus 10 is configured to provide paresthesia-reduced (e.g. paresthesia-free) high frequency pain management and rehabilitation therapy (e.g. via delivery of a stimulation signal above 600 Hz or 1 kHz, or other stimulation signal resulting in minimal paresthesia). Apparatus 10 can be configured to provide both low frequency (e.g. <1 kHz) stimulation and high frequency stimulation, such as when providing low frequency stimulation to elicit feedback from a patient during intraoperative or other (e.g. post-implantation) stimulation configuration. For example, programmer 550 and/or an external device 500 can be used during an intra-operative titration of stimulation configuration using low frequency stimulation (e.g. to position and/or confirm position of one or more stimulation elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g. via low frequency stimulation and/or high frequency stimulation) is beneficial during stimulation element 260 (e.g. electrode) implantation because a patient can provide feedback to the implanting clinician to ensure that the stimulation elements 260 are positioned close to the target neuromodulation or energy delivery site. This implantation position-optimizing procedure can advantageously reduce the required stimulation energy due to stimulation elements 260 being closer to target tissue, since a minimum threshold for efficacious stimulation amplitude is proportional to the proximity of stimulation elements 260 to target tissue (e.g. target nerves). The patient can inform the clinician of the sensation of paresthesia coverage, and the clinician can adjust stimulation element 260 position to optimize stimulation element 260 location for efficacious treatment while minimizing unintentional stimulation of non-target tissue (e.g. motor nerves or other nerves which are not causing the patient's pain). These paresthesia-inducing techniques (e.g. using low frequency stimulation and/or high frequency stimulation) can be used during or after implantation of one or more implantable devices 200/800.

In some embodiments, apparatus 10 is configured to deliver low frequency stimulation energy (e.g. electrical energy comprising a low frequency signal provided by implantable device 200 and/or implantable device 800) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g. electrical energy) to induce paresthesia, which can also be accompanied by the delivery of high frequency stimulation (e.g. to suppress and/or control pain). In some embodiments, apparatus 10 is configured to deliver low frequency stimulation (e.g. electrical energy comprising a low frequency signal) and burst stimulation, delivered simultaneously or sequentially. The low frequency stimulation and the burst stimulation can be delivered on similar and/or dissimilar stimulation elements 260 (e.g. similar or dissimilar electrode-based stimulation elements 260).

Apparatus 10 can be configured to treat neuropathy, neuralgia and/or other nerve pain that is related to: surgery; trauma; infection (e.g. a herpetic infection); and/or diabetes (e.g. diabetic neuropathy). One or more stimulation elements 260 can be configured to deliver stimulation energy (e.g. electrical energy, magnetic energy, light energy, thermal energy, sound energy, and/or chemical energy (e.g. energy from a drug or reagent) to nerve tissue such as tissue of the central nervous system and/or peripheral nervous system. One or more leads 265 (each comprising one or more stimulation elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

To treat pain related to hernia or hernia repair, one or more stimulation elements 260 (e.g. on a lead 265 and/or on a housing 210) can be positioned to stimulate tissue of the peripheral nervous system and/or the central nervous system. In some embodiments, one or more stimulation elements 260 are positioned to stimulate the cutaneous branch of the ilioinguinal, inguinal and/or genital branch of the genitofemoral nerves. In some embodiments, one or more stimulation elements 260 are positioned to stimulate corresponding branches of spinal nerves correlating to one or more dermatomes related to pain associated with at least one of hernia or hernia repair. Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these. In some embodiments, apparatus 10 is configured to treat hernia pain by delivering a low frequency stimulation signal (e.g. an electrical signal less than or equal to 1 kHz delivered by one or more electrode-based stimulation elements 260).

Alternatively or additionally, apparatus 10 can treat hernia pain with a high frequency stimulation signal, such as a signal comprising a frequency greater than 1 kHz. Stimulation can be accomplished either via subcutaneous field stimulation and/or by stimulation elements 260 positioned adjacent or at least near the nerves and/or their branches. In some embodiments, stimulation is accomplished transvascularly (e.g. stimulation including low and/or high frequencies).

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based stimulation elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more stimulation elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based stimulation elements 260 can be placed over the dorsal columns, over the dorsal roots and/or in the dorsal root entry zone, in a unilateral, bilateral and/or midline fashion.

To treat occipital neuralgia, also known as C2 neuralgia, one or more stimulation elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more stimulation elements 260, can be implanted transversely, either unilaterally or bilaterally, at the level of the appropriate target cervical nerve (C1, C2, etc.). The C1, C2, C3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more stimulation elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more stimulation elements 260 can be positioned to stimulate corresponding branches of the spinal nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. One or more leads 265 (e.g. each including one or more stimulation-delivering stimulation elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction). The tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more stimulation elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat pelvic dysfunction, overactive bladder, and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more stimulation elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more stimulation elements 260 can be positioned to stimulate tibial nerve tissue and/or sacral nerve tissue (e.g. at least the S3 nerve root) to treat overactive bladder. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210/810 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210/810 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more stimulation elements 260 are positioned proximate (e.g. in contact) with the sacral nerve root(s). The housing 210/810 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210/810 can be inserted and connected to lead 265 (e.g. via port 290/890 as described herein). Alternatively, housing 210/810 can be inserted at another internal location. If lead 265 is already connected (e.g. attached in manufacturing) to housing 210/810, lead 265 can be advanced in the opposite direction, such as from the third incision, to the second incision, to the first incision (if three incisions are made), or housing 210/810 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 210/810 are implanted. In some embodiments, a first lead 265 and a first housing 210/810 (pre-attached or attachable) are utilized in a dose titration or other "trialing procedure" (e.g. during a trial period of the present inventive concepts), and a second lead 265 and housing 210/810 (pre-attached or attachable) are implanted in the patient for subsequent treatment of the patient (e.g. during a therapy period of the present inventive concepts).

In some embodiments, one or more stimulation elements 260 are positioned to perform posterior tibial nerve stimulation (PTNS), also referred to as percutaneous tibial nerve stimulation, such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more stimulation elements 260 can be positioned to perform retrograde stimulation of the sacral nerve plexus and restore the balance between bladder inhibitory and excitatory control systems of the bladder. One or more stimulation elements 260 can be positioned above the ankle, proximate and/or into the tibial nerve. Implantable device 200/800 can deliver stimulation energy to the stimulation elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, implantable system 20 is configured to deliver a series of repeated stimulation periods, such as a regimen of approximately weekly thirty minute sessions of stimulation for twelve weeks. In some embodiments, implantable system 20 is configured to provide daily or hourly sessions that deliver stimulation for between 10 minutes and 60 minutes. In some embodiments, apparatus 10 is configured to achieve an approximate 50% reduction in urinary urge incontinence and/or urinary urgency/frequency episodes.

In some embodiments, apparatus 10 is configured to provide temporary stimulation therapy of tissue to treat overactive bladder, such as by using one or more external devices 500, such as to provide power and/or data to one or more implantable devices 200/800 to confirm acceptable improvement of the patient's overactive bladder (e.g. successful stimulation of one or more sacral nerves, tibial nerves or other tissue), before closing an incision or otherwise fully implanting one or more implantable devices 200/800. In some embodiments, a temporary stimulation therapy is provided for: up to one week, up to one month, more than 1 month, more than 2 months, or more than 3 months. In some embodiments, one or more implantable devices 200/800 are left in place if the temporary stimulation therapy period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more stimulation elements 260 are positioned to stimulate periurethral muscles. In some embodiments, one or more stimulation elements 260 are positioned to stimulate tissue of the vagina or anus. In some embodiments, one or more stimulation elements 260 are positioned to stimulate sphincter muscles for controlling the bladder, such as two stimulation elements 260 positioned on either side of the urethral orifice. In these embodiments, housing 210/810 can be implanted in suprapubic region or in the perineum. In some embodiments, lead 265 comprises (e.g. on a distal portion) a pessary ring comprising two stimulation elements 260. In some embodiments, stimulation elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more stimulation elements 260 (e.g. one or more electrical, magnetic, light or other energy delivery elements) of one or more leads 265 and/or one or more implantable devices 200/800 are configured to stimulate tissue to treat fecal incontinence, such as to treat tissue selected from the group consisting of:

sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more stimulation elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 stimulation elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 μsec and 240 μsec (or between 1 μsec and 200 μsec); provides electrical stimulation energy with an amplitude of approximately 0.1V to 8.5V (e.g. providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off); delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more stimulation elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more stimulation elements 260 are positioned to stimulate nerve tissue.

In some embodiments, apparatus 10 is configured to treat neuralgia, such as a neuralgia resulting from groin surgery (e.g. hernia or other groin surgery), and one or more stimulation elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more stimulation elements 260 are positioned to stimulate axial nerve tissue (e.g. one or more stimulation elements 260 positioned on a lead 265 implanted in a suprascapular location).

In some embodiments, apparatus 10 is configured to treat neuralgia, such as a neuralgia resulting from lung surgery, and one or more stimulation elements 260 are positioned to stimulate intercostal nerve tissue.

In some embodiments, apparatus 10 is configured to treat neuralgia, such as a neuralgia associated with carpal tunnel syndrome, and one or more stimulation elements 260 are positioned to stimulate median nerve tissue.

In some embodiments, apparatus 10 is configured to treat neuralgia, such as a neuralgia associated with temporomandibular joint disorder (TMJ), and one or more stimulation elements 260 are positioned to stimulate V2 of trigeminal nerve tissue.

In some embodiments, apparatus 10 is configured to treat neuralgia, such as a facial neuralgia, and one or more stimulation elements 260 are positioned to stimulate trigeminal nerve tissue.

In some embodiments, apparatus 10 is configured to treat neuralgia, such as a leg (sciatic) neuralgia, and one or more stimulation elements 260 are positioned to stimulate nerve tissue proximal a contributing lesion.

In some embodiments, apparatus 10 is configured to treat pelvic pain, such as interstitial cystitis and/or bladder pain, and one or more stimulation elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more stimulation elements 260 are positioned to stimulate peripheral nerve tissue such as pudendal tissue and/or S-2, S-3 and/or S-4 roots.

In some embodiments, apparatus 10 is configured to treat subcutaneous pain, and one or more stimulation elements 260 (e.g. paddle electrodes) are positioned to stimulate nerve tissue.

In some embodiments, apparatus 10 is configured to treat diabetic neuropathy, such as painful diabetic neuropathy, and one or more stimulation elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more stimulation elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more stimulation elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more stimulation elements 260 can comprise a paddle electrode, such as one or more paddle electrodes implanted in the foot, leg and/or arm. Lead 265 and/or one or more stimulation elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g. each including one or more stimulation elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off of the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, stimulation element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off of the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more stimulation elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more stimulation elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 can be configured to transvascularly stimulate at least one of a median nerve, an ulnar nerve or a radial nerve, and stimulation element 260 can comprise one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 can be configured to transvascularly stimulate at least one of a median nerve or an ulnar nerve, and stimulation element 260 can comprise one or more electrodes positioned in a vessel selected from the group consisting of: brachial vein; brachial artery; and combinations of one or more of these. In some embodiments, apparatus 10 can be configured to transvascularly stimulate the radial nerve, and stimulation element 260 can comprise one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and stimulation element 260 can comprise one or more electrodes positioned in the basilic vein. In some embodiments, apparatus 10 is configured to transvascularly stimulate the ulnar nerve, and stimulation element 260 can comprise one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and stimulation element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more stimulation elements 260 (e.g. one or more electrodes) are positioned from T5-S5, such as to capture the area of pain or reduced circulation of the leg or foot. One or more stimulation elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more stimulation elements 260 (e.g. one or more electrodes attached to one or more leads 265) can be positioned to transvascularly stimulate one or more nerves, such as one or more nerves in the foot, leg and/or arm, such as when the one or more stimulation elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more stimulation elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more stimulation elements 260 (e.g. one or more electrodes attached to one or more leads 265) can be positioned to stimulate dorsal root ganglia that supply the following nerves (e.g. to treat the leg and/or foot): common peroneal (L4-S2); tibial (L4-S3); femoral (L2-L4); and combinations of one or more of these. One or more stimulation elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e. stump pain), such as by using a high frequency alternating current (HFAC) block approach. In these embodiments, one or more leads 265 can be implanted such that one or more stimulation elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more stimulation elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgical (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more stimulation elements 260 are implanted in a blood vessel). Housing 210/810 can be implanted anywhere in the head under the skin, including: behind the ear, back of the head, the neck, in the face, and the like, where an one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210/810 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approach. In these embodiments, one or more leads 265 can be implanted such that one or more stimulation elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more stimulation elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these. In these embodiments, apparatus 10 can be configured to deliver stimulation to median nerve tissue; ulnar nerve tissue and/or radial nerve tissue.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, apparatus 10 is configured to treat knee pain. Knee pain from joint degeneration or join replacement surgery can be treated via stimulation of the nerves innervating the knee and/or via stimulation of the tissue surrounding the knee (sometimes referred to as peripheral field stimulation). Apparatus 10 can comprise between one and eight leads 265 whose stimulation elements 260 are placed near and around the knee. In some embodiments, four leads 265 are placed, in locations medial, lateral, superior and inferior to the knee. The leads 265 can be placed subcutaneously for field stimulation, or they can be placed directly adjacent to specific nerve targets. Applicable nerve targets are as follows: medial knee can include medial femoral cutaneous and infrapatellar cutaneous branches of saphenous nerve; lateral knee can include constant articular branches of common peroneal, lateral retinacular nerve; anterior knee can include lateral, medial, and anterior cutaneous femoral nerve, infrapatellar branch of saphenous nerve, medial and lateral retinacular nerve and articular branches of peroneal nerve; posterior knee can include obturator, posterior tibial and sciatic nerves. In addition, the following nerves can be stimulated via stimulation elements 260 to treat knee pain: nerves arising from the tibial nerve such as the superior, middle and inferior genicular nerves; nerves arising from the common peroneal such as the superior lateral, inferior lateral, and recurrent genicular nerves; and nerves arising from the obturator nerve such as the genicular branch of obturator; and nerves arising from the femoral nerve such as the saphenous nerve. Each of these targets can be stimulated transvascularly by one or more stimulation elements 260.

In some embodiments, one or more implantable devices 200/800 are configured to deliver stimulation energy (e.g. via one or more stimulation elements 260 comprising an electrode) with a stimulation waveform comprising one or more high frequency signals (e.g. a signal comprising one or more high frequency components). For example, one or more implantable devices 200/800 can deliver one or more stimulation waveforms comprising one or more signals above 600 Hz, such as one or more signals above 1.0 kHz, 1.2 kHz, 5 kHz, 10 kHz or 25 kHz. In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200/800 can be configured to deliver stimulation energy with a stimulation waveform that varies over time. In some embodiments, one or more stimulation parameters of the stimulation waveform are randomly varied over time, such as by using a probability distribution as described in applicant's co-pending application International PCT Patent Application Serial Number PCT/US2017/017978, titled "Apparatus with Enhanced Stimulation Waveforms", filed Feb. 15, 2017. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g. a pulse comprising at least a cathodic portion and an anodic portion). In some embodiments, single or groups of pulses are provided at time-varying modes of repetition (e.g. regular intervals for a period, then a period of irregular intervals) or at regular intervals with occasional (random) spurious pulses inserted (creating a single irregular event in an otherwise regular series). Non-limiting examples of waveform variations include: a variation in frequency (e.g. frequency of one or more signals of the waveform); variation of a signal amplitude; variation of interval time period (e.g. at time period between pulses or a time period between pulse trains); variation of a pulse width; multiple piecewise or continuous variations of one of more stimulation parameters in a single pulse (e.g. multi-step, multi-amplitude in one "super-pulse"); variation of pulse symmetry (e.g. via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200/800 can be configured to vary a stimulation waveform "systematically" such as a variation performed temporally (e.g. on predetermined similar or dissimilar time intervals) and/or a variation performed based on a parameter, such as a measured parameter that can be based on a signal produced by a sensor of implantable device 200/800 or another component of apparatus 10 (e.g. one or more of functional element 299/599/899). Alternatively or additionally, apparatus 10 and/or implantable device 200/800 can be configured to vary a stimulation waveform randomly. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters as described herein. One or more stimulation parameters can be varied randomly through the use of one or more probability distributions, as described herebelow.

In some embodiments, the amplitude of a signal delivered by one or more implantable devices 200/800 is adjusted to prevent discomfort to the patient (e.g. paresthesia or other undesired condition) from the stimulation signal. In some embodiments, the amplitude of the stimulation signal can be ramped (e.g. up and/or down), a single time or multiple times (e.g. continuously or intermittently). In some embodiments, a titration procedure can be performed (e.g. the trial period of the present inventive concepts) to "set" one or more stimulation parameters based on avoiding patient discomfort.

In some embodiments, one or more implantable devices 200/800 are configured to deliver stimulation energy (e.g. via one or more stimulation elements 260 comprising an electrode) with a stimulation waveform comprising one or more waveforms configured to one or more specific conditions of a patient. Each stimulation waveform can comprise a series of continuous pulses, intermittent pulses, and/or spurious pulses (e.g. occasional events in an otherwise continuous stream). Each pulse can comprise a pulse train that is repeatedly delivered by implantable device 200/800, the train comprising one or more cathodic pulses and/or one or more anodic pulses. In some embodiments, implantable device 200/800 delivers a multiphasic pulse comprising at least two cathodic pulses and/or anodic pulses, with or without any time between each pulse. For example, implantable device 200/800 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g. comprise an exponential portion), such as dynamic return pulses that exceed a minimum current (e.g. at least 1 mA, 10 mA or 50 mA) for a short duration (e.g. for approximately 1 μsec), and then decay to lower current levels (e.g. a level of approximately 100 nA), with a time constant on the order of 1 μsec to 100 μsec.

The stimulation waveforms delivered by implantable device 200/800 can comprise one or more high frequencies (e.g. as described herein). The stimulation waveform frequency or other stimulation parameter can be set and/or adjusted (hereinafter "adjusted") to optimize therapeutic benefit to the patient and minimize undesired effects (e.g. paresthesia or other patient discomfort). In some embodiments, a stimulation waveform is adjusted based on a signal produced by a sensor of apparatus 10 (e.g. a sensor of implantable device 200/800, such as a stimulation element 260 or functional element 299/899 configured as a sensor). Adjustment of a stimulation waveform parameter can be performed automatically by the implantable device 200/800 and/or via an external device 500 and/or programmer 550.

In some embodiments, a pulse shape of a stimulation waveform can be varied, such as a pulse shape comprising: a sinusoidal geometry; a square geometry (e.g. a waveform comprising a square wave); a rectangular geometry; a triangular geometry; (e.g. symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g. anodal phase) of a stimulation waveform is varied by implantable device 200/800.

Inter-pulse gap, the time between one or more pulses (e.g. a biphasic or other multiphasic pulse that is repeated continuously), can be varied systematically and/or randomly by implantable device 200/800. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly. such as a random variation based on a distribution (e.g. a probability distribution with a pre-determined shape) as described herebelow.

In some embodiments, implantable device 200/800 delivers a stimulation waveform comprising a series of frequency modulated (FM) pulses, such that the frequency of stimulation varies. Implantable device 200/800 can be configured to deliver a frequency modulated stimulation waveform comprising a carrier signal, at a carrier frequency, that is modulated continuously between a first frequency and a second frequency. For example, implantable device 200/800 can deliver a stimulation waveform that modulates between 2.0 kHz and 3.0 kHz every second (e.g. comprising a carrier signal at 2.5 kHz that is modulated at 1 Hz) with a modulation range (the excursion from the carrier signal) of +/−500 Hz. In some embodiments, implantable device 200/800 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200/800 delivers a stimulation waveform comprising a series of amplitude modulated (AM) pulses, such that the amplitude of stimulation varies (e.g. varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g. a signal comprising a modulation frequency of 1 Hz). In these embodiments, the depth of modulation would be 33%, where depth of modulation is equal to 1−[lower range/upper range]. In some embodiments, amplitude of delivered current fluctuates between 1 mA and 3 mA (i.e. a depth of modulation of 66%), while in other embodiments, current fluctuates between 0 mA and 3 mA (e.g. a depth of modulation of 100%). In some embodiments, implantable device 200/800 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

In some embodiments, implantable device 200/800 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g. a quiescent period) can be included. In some embodiments, controller 250/850 comprises one or more reconfigurable stimulation blocks including one or more Howland or other current sources. The one or more current sources (e.g. two or more current sources) can each be attached to a stimulation element 260 (e.g. in a monopolar configuration when the current source is also connected to housing 210/810 or in a bipolar configuration when the current source is connected to a pair of stimulation elements 260). Alternatively, controller 250/850 can comprise one or more current sources that are attached to a matrix of switches that selectively connect the one or more current sources to multiple stimulation elements 260 (e.g. connect a single current source to 2, 4, 8, 12 or 16 electrodes). In some embodiments, controller 250/850 is configured such that a stimulation waveform signal provided to the current source passes through a capacitor (e.g. capacitor C1 shown), the capacitor providing DC balance.

In some embodiments, implantable device 200/800 delivers a stimulation waveform comprising delivery of multiple trains of pulses that are delivered intermittently, a "burst stimulation" waveform as defined hereabove. For example, implantable device 200/800 can be configured to deliver a series or train of five pulses, each with a 1 msec pulse width, and each of the five pulses can be separated by an inter-pulse gap of 4 msec, creating a train-on period of 16 msec. These five pulses can be repeated every 25 msec (the "inter-train period"). In some embodiments, implantable device 200/800 can be configured to deliver a burst stimulation waveform comprising a pulse width between 5 μsec and 1 msec. Implantable device 200/800 can deliver a train or burst stimulation waveform comprising pulses with constant pulse widths and/or varying pulse widths, such as when the pulse widths (and/or other stimulation parameters) are varied randomly and/or systematically. Implantable device 200/800 can deliver a train or burst stimulation waveform with a varied or constant pulse shape selected from the group consisting of: sinusoid; square, rectangle; triangle (symmetric or asymmetric); trapezoid; sawtooth; ramp (e.g. a linear ramp); exponential curve; piece-wise step function; and combinations of one or more of these. Implantable device 200/800 can deliver a train or burst stimulation waveform with an inter-pulse gap less than inter-train period. The inter-pulse gap can be relatively constant or it can be varied, such as when implantable device 200/800 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200/800 can deliver a train stimulation waveform with an inter-pulse gap between 1 μsec and 1 second. Implantable device 200/800 can deliver a burst stimulation waveform with an inter-train period between 1 μsec and 1 second. Implantable device 200/800 can deliver a burst stimulation waveform with an inter-burst period between 20 μsec and 24 hours. The inter-burst period can be relatively constant or it can be varied, such as when implantable device 200/800 randomly varies the inter-burst period or varies the inter-burst period systematically. In some embodiments, inter-burst period is varied by the user, such as via a user using programmer 550. In these embodiments, user activation can be regulated with one or more safeguards or other limits such as those incorporated into patient controlled analgesia devices. The inter-train period can be varied between 1 μsec and 24 hours. Implantable device 200/800 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant or it can be varied, such as when implantable device 200/800 randomly varies the train-on and/or burst-on period or varies the train-on and/or burst-on period systematically. Implantable device 200/800 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g. linear ramp); and combinations of one or more of these. Implantable device 200/800 can deliver a train and/or burst stimulation waveform with a train ramp duration or burst ramp duration between 1 μsec to 10 minutes. Implantable device 200/800 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period as described herein. The amplitude of the signal contained in these quiescent period may be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g. electrical energy comprising a low frequency signal) and burst stimulation; burst stimulation (e.g. burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more stimulation elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters to optimize (e.g. balance the benefits of): therapeutic benefit, system efficiency, stimulation efficiency, avoidance and/or reduction of paresthesia, and/or reduction of charge.

Figure 1A:
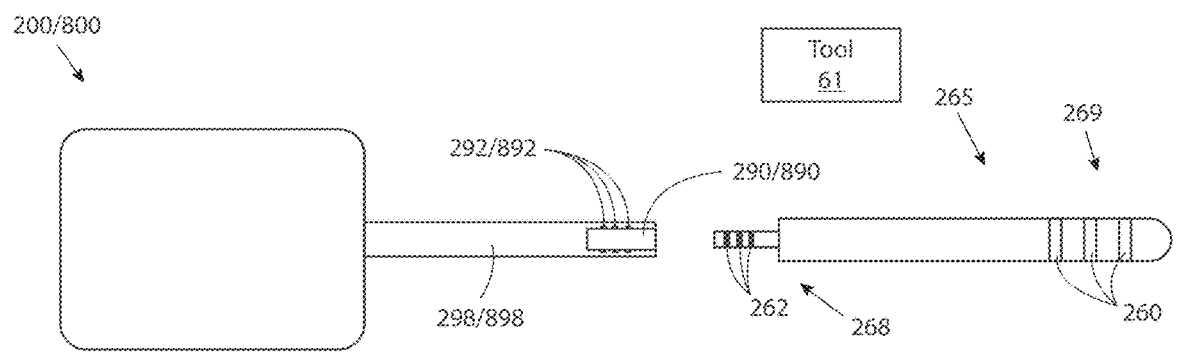
FIG. 1A is a schematic view of an implantable device comprising an extending conduit for attachment to a lead, consistent with the present inventive concepts.

In some embodiments, implantable device 200/800 comprise a filament (e.g. a flexible filament comprising one or more wires, optical fibers, wave guides, and the like), conduit 298/898, which extends from housing 210/810 as shown in FIG. 1A. Port 290/890 is positioned on an end of conduit 298/898. As described above, lead 265 can be operably attached to implantable device 200/800 via port 290/890 in one or more clinical procedures (e.g. a first clinical procedure in which lead 265 is attached to implantable device 200 at port 290 of conduit 298 and a subsequent second clinical procedure in which lead 265 is attached to implantable device 800 at port 890 of conduit 898, such as is described herein in reference to FIGS. 1 and/or 2). Lead 265 is shown prior to attachment to port 290/890 in FIG. 1A. A tool, tool 61, can be included to assist in the attachment of lead 265 to port 290/890, such as tool 61 described herebelow.

Figure 1B:
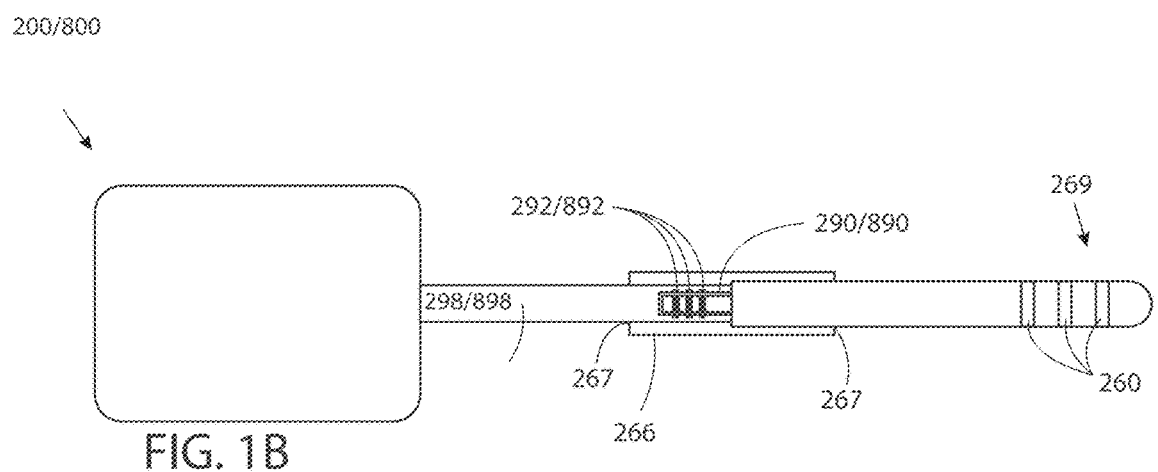
FIG. 1B is a schematic view of an implantable device comprising an extending conduit for attachment to a lead and a contamination-limiting fitting, consistent with the present inventive concepts.

In some embodiments, implantable device 200/800 comprises both conduit 298/898, and a sleeve, collar or other attachment element, fitting 266, which is used to create a seal, seal 267, between lead 265 and port 290/890. In FIG. 1B, lead 265 has been connected to port 290/890, and fitting 266 has been positioned about the connection, such as to create seal 267. Seal 267 can be configured to prevent significant contamination from interfering with the operable connection (e.g. to prevent shorting of contacts, preventing loss or degradation of an electrical, optical and/or acoustic connection, and/or prevent another undesired effect). In some embodiments, implantable system 20 does not include fitting 266, and a seal is provided between one or more portions of lead 265 and implantable device 200/800. Fitting 266 and/or seal 267 can be configured to significant contamination for a limited period of time (e.g. seal 267 comprises a "temporary seal"), for example less than 1 week, less than one month, less than 2 months, and/or less than 3 months, such as when fitting 266 and/or seal 267 is present for a limited period of time (e.g. a limited period of time in which implantable device 200 and corresponding attachment port 290 are attached to lead 265 during a trial period as described herein).

Figure 1C:
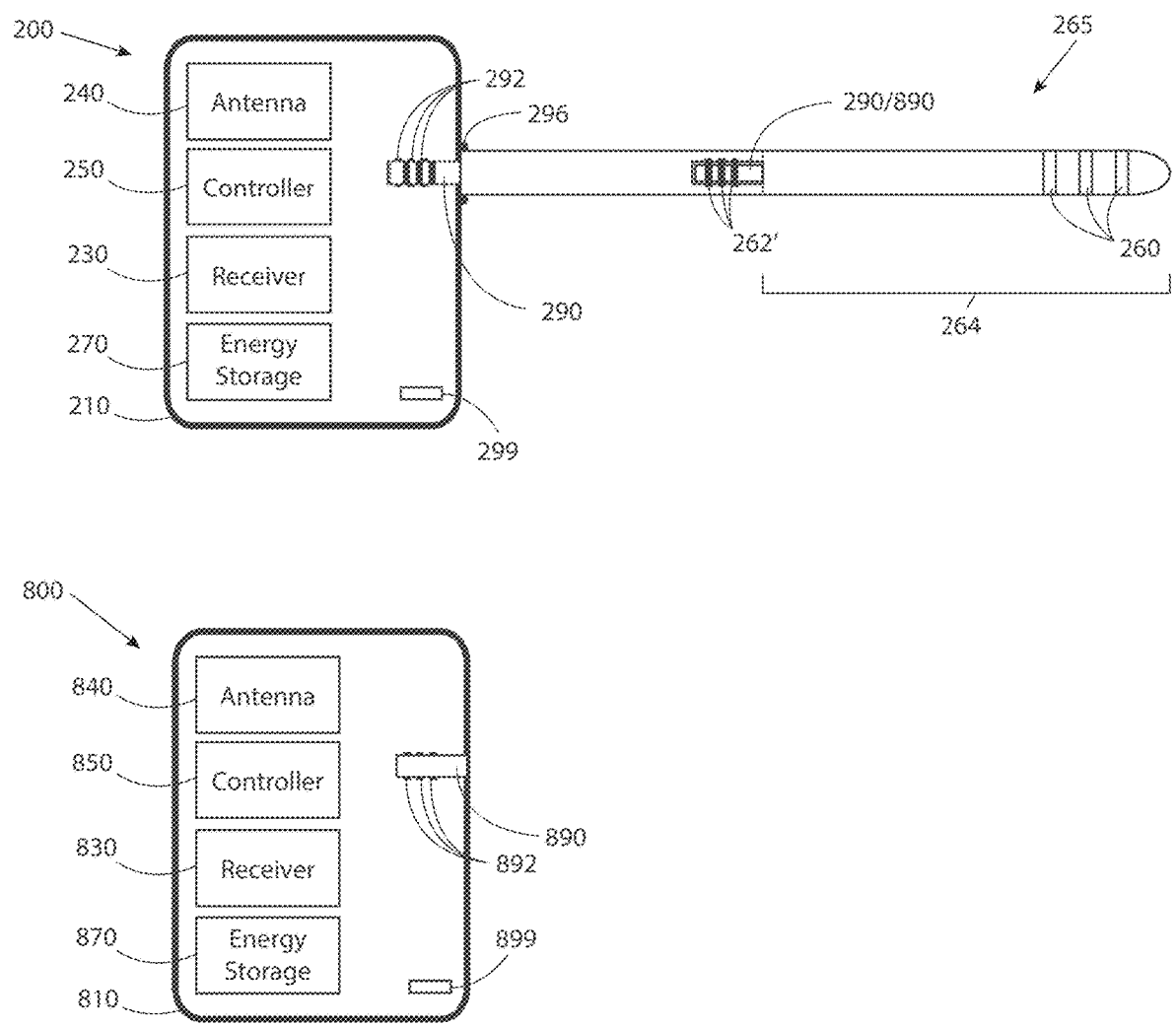
FIG. 1C is a schematic view of two implantable devices, the first implantable device comprising a pre-attached lead, the lead comprising a removable portion, consistent with the present inventive concepts.

Referring now to FIG. 1C, a schematic view of two implantable devices is illustrated, the first implantable device comprising a pre-attached lead and the lead comprising a removable portion, consistent with the present inventive concepts. Implantable device 200 and implantable device 800 can be of similar construction and arrangement to those described hereabove in reference to FIG. 1. Lead 265 is shown attached to implantable device 200, such as a permanent attachment made in a manufacturing process of implantable device 200. In some embodiments, one or more gaskets, gasket 296 shown, is used to seal lead 265 to housing 210. Lead 265 comprises one or more stimulation elements 260 (e.g. electrodes), which are operably connected to one or more internal components of implantable device 200 via conduit 263. Implantable device 200 and attached lead 265 can be implanted in the patient, such as to perform a trialing procedure of the present inventive concepts.

Lead 265 can comprise a removable distal portion 264, such that detachment of distal portion 264 from the remainder of lead 265 exposes contacts 262'. For example, after a trial procedure is performed with implantable device 200 and lead 265 (e.g. in the condition shown in FIG. 1C), distal portion 264 can be detached from the more proximal portion of lead 265 (and thus from implantable device 200), such that contacts 262' can be advanced into connector 890 of implantable device 800 such that contacts 262' operably connect to contacts 890. In some embodiments, lead 265 comprises a sleeve, or other seal-creating element, surrounding the junction of distal portion 264 and the remaining (proximal) portion of lead 265, not shown but such as sleeve 266 described hereabove in reference to FIG. 1B.

Figure 2:
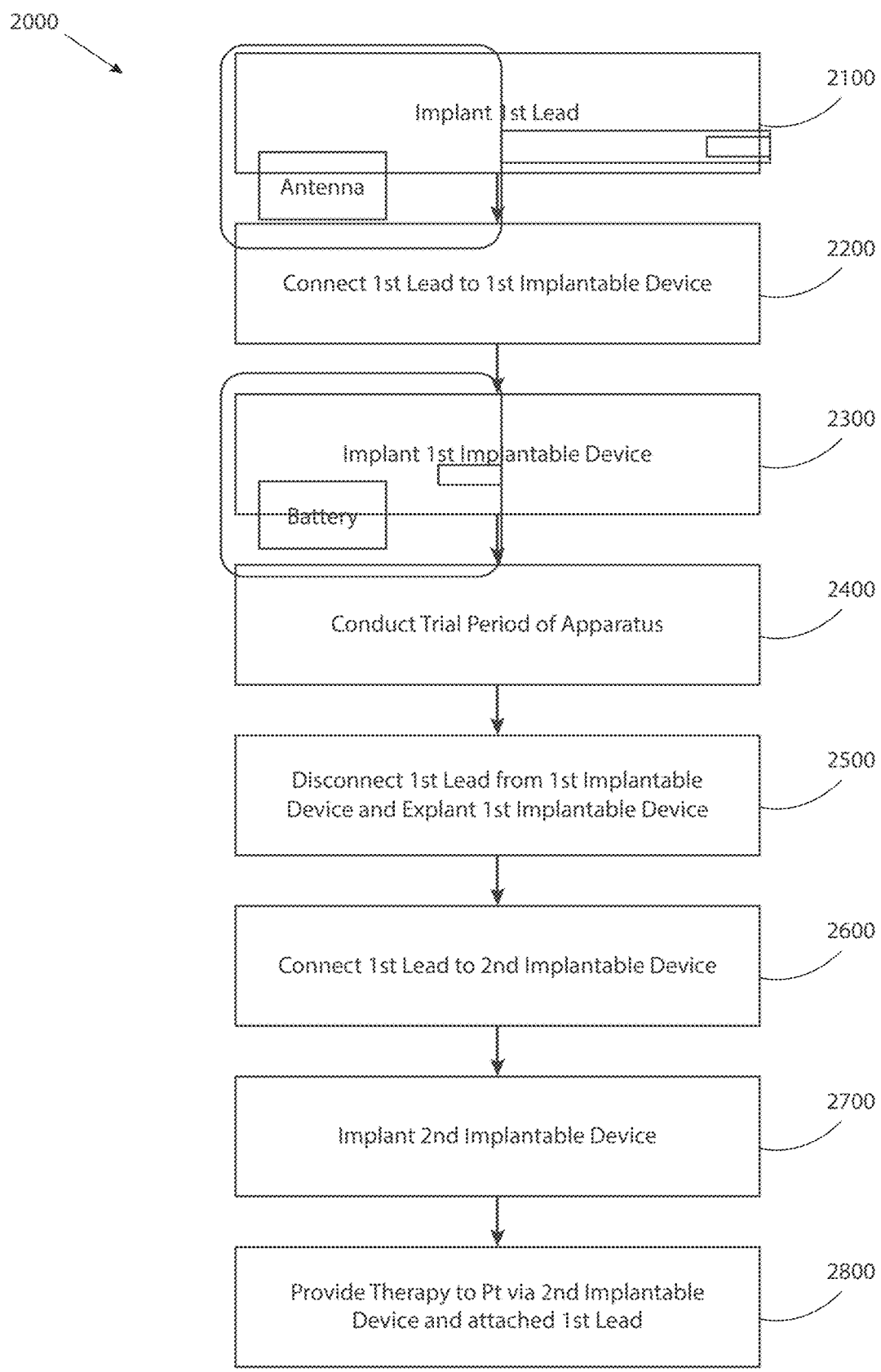
FIG. 2 is a flow chart of a method of providing stimulation for an initial trial period, and a subsequent therapy period, consistent with the present inventive concepts.

Referring now to FIG. 2, a flow chart of a method of providing stimulation for an initial trial period, and a subsequent therapy period is illustrated, consistent with the present inventive concepts. The method 2000 of FIG. 2 can be accomplished with apparatus 10 and any of its components as described in reference to the associated figures, and will be described using those components. STEPS 2100, 2200 and 2300 represent a first clinical procedure (e.g. a surgery such as a minimally invasive surgery) performed on a patient to receive stimulation via apparatus 10. In STEP 2100, lead 265 is implanted in the patient. In STEP 2200, lead 265 is attached to one or more implantable stimulation devices, such as when lead 265 is attached to implantable device 200 at attachment port 290. In STEP 2300, implantable device 200 is implanted in the patient. STEPs 2100, 2200 and 2300, can be performed in any order.

In STEP 2400, a trial period is performed in which implantable device 200 delivers stimulation energy to the patient, such as to attempt to provide pain relief or other therapy as described herein. During the trial period of STEP 2400, stimulation can be provided in order to evaluate use of apparatus 10 to provide therapy to the patient, such as is described hereabove in reference to FIG. 1. During the trial period, stimulation settings can be varied (e.g. variations of: stimulation element 260 positions, configurations and/or combinations; stimulation frequencies; stimulation waveform shapes; and/or stimulation pulse widths and/or amplitudes), such as to optimize or at least improve therapeutic benefit to the patient. The trial period of STEP 2400 can have a duration of at least 1 week, at least 2 weeks, at least 1 month, at least 2 months, and/or at least 3 months. During the trialing period, implantable device 200 receives power and data from external system 50 (e.g. from one or more external devices 500), as is described herein, avoiding the need for a large capacity energy storage assembly 270 (e.g. reducing the volume of implantable device 200).

STEPS 2500, 2600 and 2700 represent a second clinical procedure (e.g. a surgery such as a minimally invasive surgery) performed on the patient. In STEP 2500, lead 265 is disconnected from implantable device 200 (e.g. disconnected from attachment port 290), and implantable device 200 is explanted from the patient. In STEP 2600, lead 265 is attached to one or more other implantable stimulation devices, such as when lead 265 is attached to implantable device 800 at attachment port 890. In STEP 2700, implantable device 800 is implanted in the patient. STEPs 2500, 2600 and 2700 can be performed in any order.

In STEP 2800, a therapy period is performed in which implantable device 800 delivers stimulation energy to the patient, such as to provide pain relief or other therapy as described herein. Implantable device 800 can provide long-term therapy to the patient for a therapy period of at least 1 month, at least 6 months, at least 1 year and/or at least 2 years. During the therapy period, implantable device 800 may not receive any power from external system 50, such as when energy storage assembly 870 comprises a capacity sufficient to deliver stimulation for the entire therapy period. In alternative embodiments, energy storage assembly 870 is recharged periodically (e.g. not continually), such as via a wireless recharge (e.g. via a RF or other wireless transmitter, magnetic coupling, inductive coupling, capacitive coupling and/or other wireless power transmission means).

In some embodiments, the therapy period of STEP 2800 is stopped due to one or more of: patient therapy is no longer needed; energy storage assembly 870 is depleted (e.g. after a period of at least 1 year); and/or an infection or other patient complication occurs. In these embodiments, all or a portion of the method of FIG. 2 can be repeated, such as by returning to STEP 2100, 2200 or 2300, or returning directly to STEP 2500, 2600 or 2700.

In some embodiments, after completion of STEP 2400, use of apparatus 10 is stopped, such as when adequate therapeutic results are not achieved in STEP 2400 (e.g. despite various changes in stimulation parameters). Alternatively, after completion of STEP 2400, if adequate therapy is achieved, long-term therapy can continue to be provided by implantable device 200, without the need for the second clinical procedure of STEPs 2500, 2600 and 2700 nor the use of a second implantable device such as implantable device 800.

Figure 3:
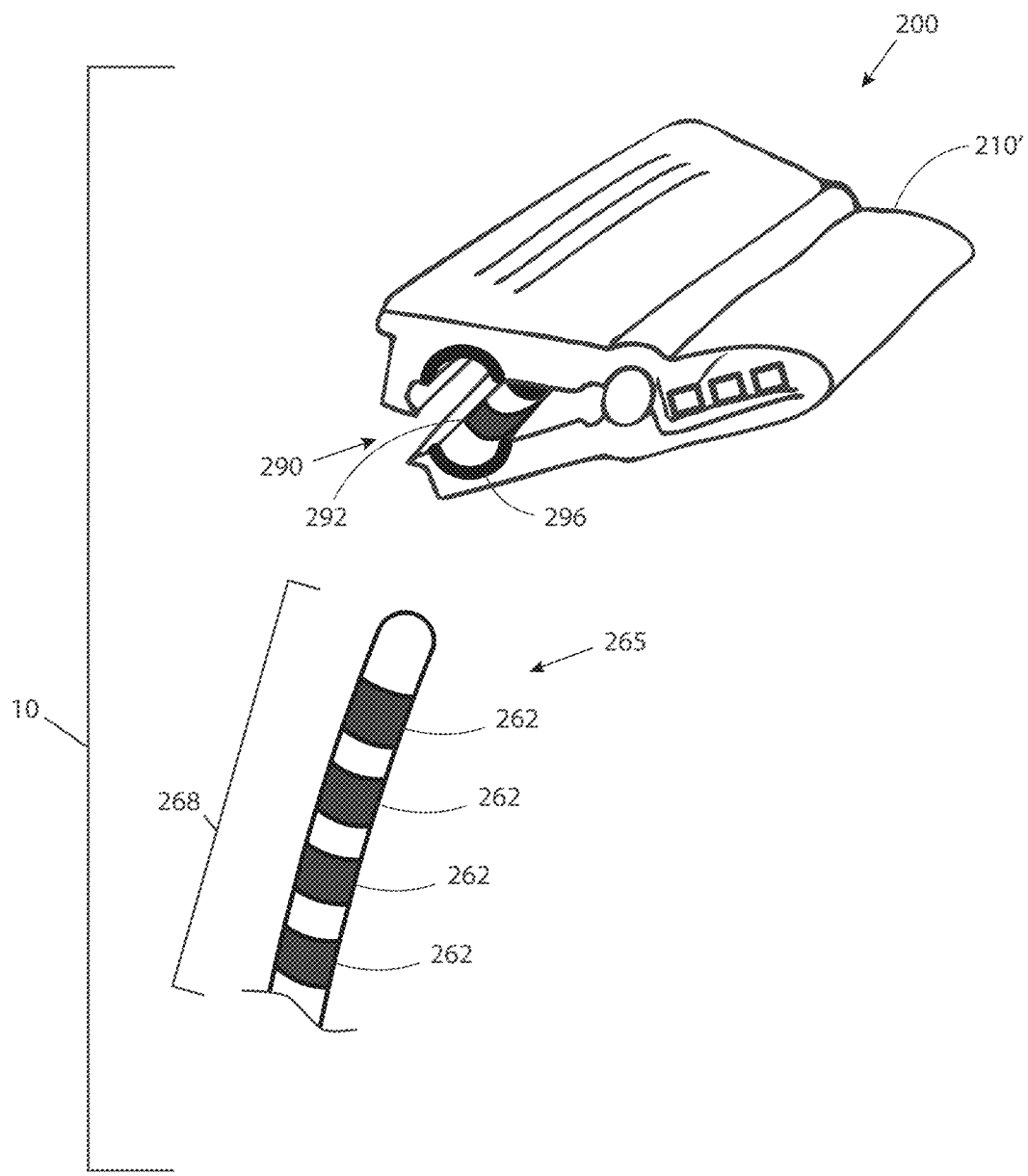
FIG. 3 is a perspective view of an apparatus comprising a temporary implantable device and an attachable lead for use in a trialing period, consistent with the present inventive concepts.

Referring now to FIG. 3, a perspective view of an apparatus comprising a temporary implantable device and an attachable lead for use in a trialing period is illustrated, consistent with the present inventive concepts. Apparatus 10 comprises implantable device 200, lead 265, and other components of similar construction and arrangement to those described hereabove in reference to FIG. 1. Implantable device 200 of FIG. 3 comprises a clam-shell shaped housing, housing 210'.

During a clinical procedure, the proximal portion 268 of lead 265 is inserted into attachment port 290 comprising two hinged portions (e.g. two flexible-hinge portions) of housing 210' in a clam-shell arrangement. Housing 210' is compressed to make electrical, optical, acoustic, mechanical and/or other operable connection with proximal portion 296 of lead 265, as well as sealingly surround proximal portion 268, such that contacts 262 are maintained within housing 210' and a seal (e.g. a temporary seal as described herein) is maintained to at least temporarily prevent contamination from interfering with the connection between contacts 262 and correspondingly aligned contacts 292 of attachment port 290. Implantable device 200 can comprise one or more gaskets and/or other sealing material, gasket 296 shown, to assist in creating the seal between lead 265 and implantable device 200.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 4A:
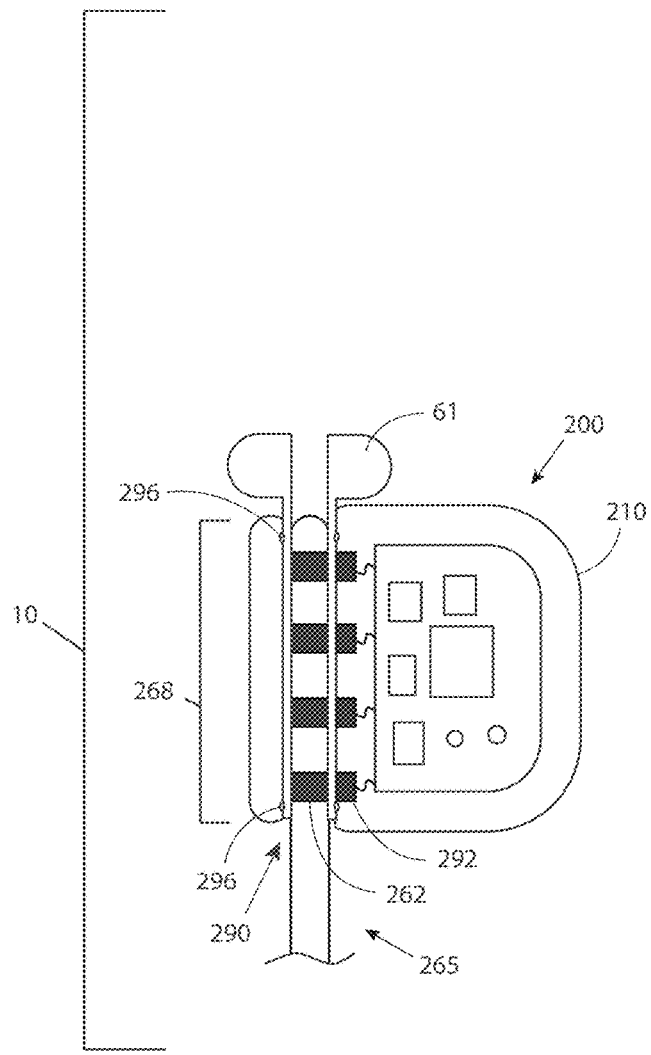
FIGS. 4A-B are top views of an apparatus comprising a temporary implantable device and an attachment lead for use in a trialing period, consistent with the present inventive concepts.
Figure 4B:
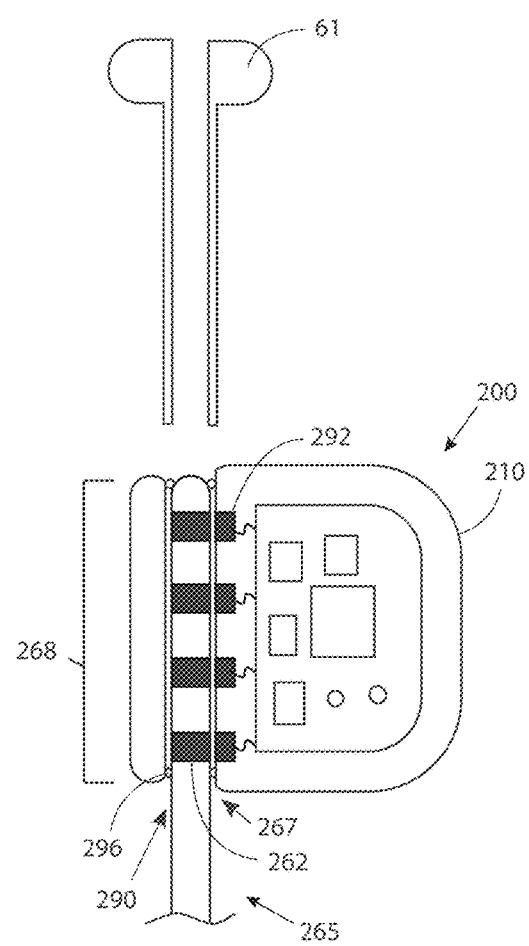

Referring now to FIGS. 4A-B, top views of an apparatus comprising a temporary implantable device and an attachment lead for use in a trialing period is illustrated, consistent with the present inventive concepts. Implantable device 200 of FIGS. 4A-B is shown with the top portion of housing 210 removed for illustrative clarity. Apparatus 10 comprises implantable device 200, lead 265, and other components of similar construction and arrangement to those described hereabove in reference to FIG. 1. Implantable device 200 of FIGS. 4A-B comprises attachment port 290 which extends from the bottom to the top of implantable device 200, such as to receive the proximal portion of lead 265 including all contacts 262.

Apparatus 10 can include tool 61, configured to slidingly engage and expand (e.g. radially expand) attachment port 290, such that proximal portion 268 can be inserted into tool 61, while tool 61 is in place within attachment port 290, as shown in FIG. 4A. Radial expansion of attachment port 290 can include expansion and/or displacement of one or more of: housing 210; and/or one or more gaskets within attachment port 290, gasket 296. Subsequently, tool 61 can be removed from attachment port 290, such that attachment port 290 radially contracts, as shown in FIG. 4B. After removal of tool 61, seal 267 is created, such as a temporary seal as described herein. With tool 61 removed, contacts 262 of lead 265 are operably connected (e.g. electrically, optically, mechanically, and/or acoustically connected) to contacts 292 of attachment port 290, such as to create an operable connection with one or more internal components of implantable assembly 200.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 5A:
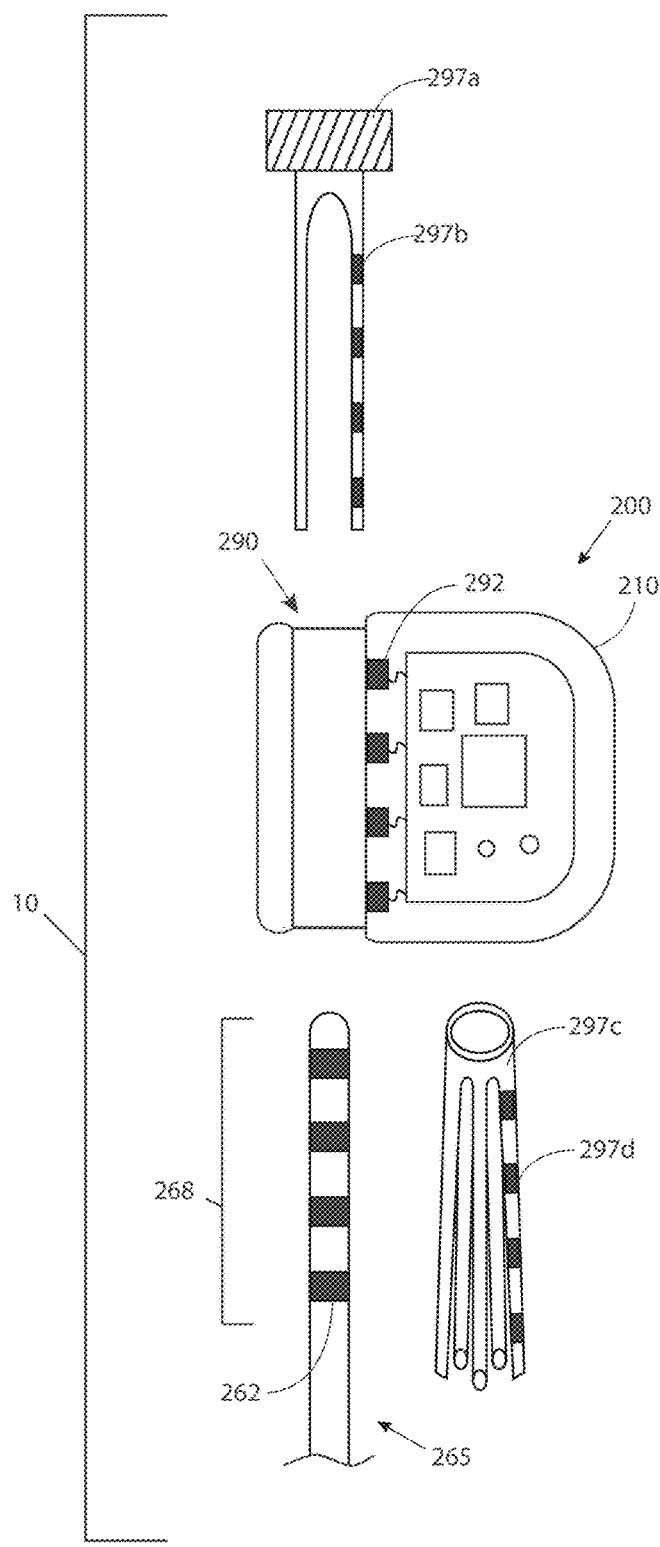
FIGS. 5A-B are top views of an apparatus comprising a temporary implantable device and an attachment lead for use in a trialing period, consistent with the present inventive concepts.
Figure 5B:
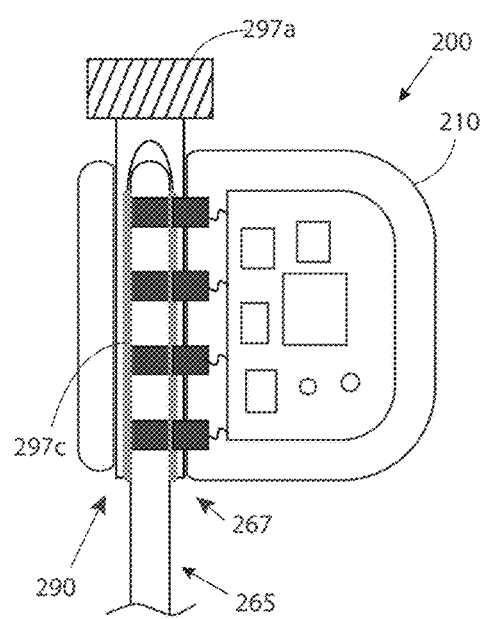

Referring now to FIGS. 5A-B, top views of an apparatus comprising a temporary implantable device and an attachment lead for use in a trialing period is illustrated, consistent with the present inventive concepts. Implantable device 200 of FIGS. 5A-B is shown with the top portion of housing 210 removed for illustrative clarity. Apparatus 10 comprises implantable device 200, lead 265, and other components of similar construction and arrangement to those described hereabove in reference to FIG. 1. Implantable device 200 of FIGS. 5A-B comprises attachment port 290 which extends from the bottom to the top of implantable device 200, such as to receive the proximal portion 268 of lead 265 including all contacts 262.

Implantable device 200 includes a connecting and inserting component, sleeve 297a, configured to slidingly engage attachment port 290, such that proximal portion 268 can be positioned within sleeve 297a while sleeve 297a is in place within attachment port 290. In some embodiments, sleeve 297a is positioned within attachment port 290, after which lead 265 is inserted into sleeve 297a. Alternatively, lead 265 can be inserted into attachment port 290, after which sleeve 297a can be inserted between lead 265 and attachment port 290. Sleeve 297a comprises connecting segments 297b (e.g. conductive material) which are positioned to align with contacts 262 of lead 265 and contacts 292 of attachment port 290, such as to provide an operable connection between contacts 262 and contacts 292 when lead 265 and sleeve 297a are in place within implantable device 200.

In some embodiments, sleeve 297a further comprises a compressible gasket, gasket 297c. Gasket 297c can be fixedly attached to sleeve 297a, or it can be a separate component as shown in FIG. 5A. In some embodiments, gasket 297c is a separate component that is positioned about proximal portion 268 of lead 265, after which it is inserted into sleeve 297a (which is already positioned in attachment port 290) or into attachment port 290 (after which sleeve 297a is inserted). Gasket 297c comprises connecting segments 297d (e.g. conductive material) which are positioned to align with connecting segments 297b of sleeve 297a, contacts 262 of lead 265, and contacts 292 of attachment port 290, such as to provide an operable connection between contacts 262 and contacts 292 when lead 265, sleeve 297a, and gasket 297c are in place within implantable device 200 (as shown in FIG. 5B).

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 6A:
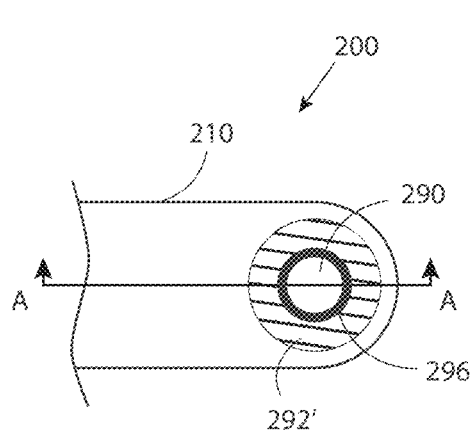
FIGS. 6A-C are a side view, a sectional view, and a perspective view, respectively, of an attachment port of an implantable device, consistent with the present inventive concepts.
Figure 6B:
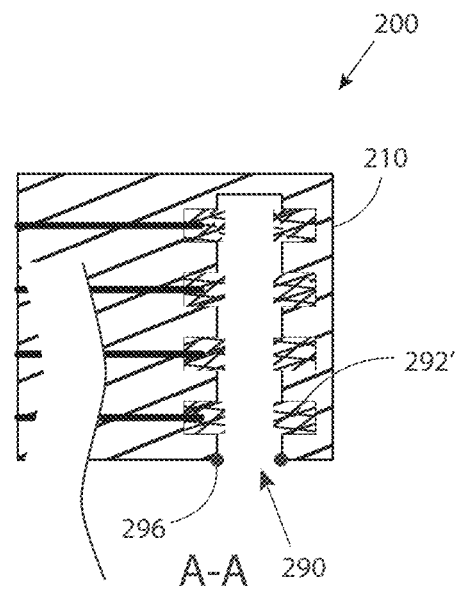
Figure 6C:
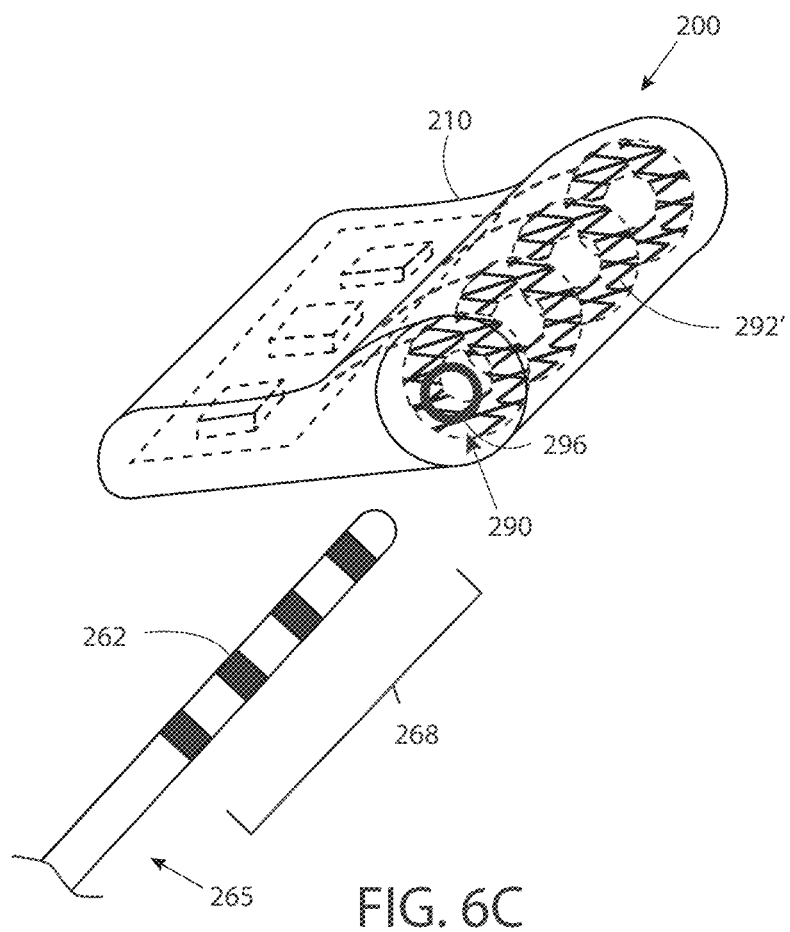

Referring now to FIGS. 6A-C, a side view, a sectional view, and a perspective view, respectively, of an attachment port of an implantable device are illustrated, consistent with the present inventive concepts. Apparatus 10 comprises implantable device 200, lead 265, and other components of similar construction and arrangement to those described hereabove in reference to FIG. 1. Implantable device 200 of FIGS. 6A-C comprises attachment port 290 which extends within implantable device 200, such as to receive the proximal portion 268 of lead 265 including all contacts 262. Attachment port 290 includes contacts 292' comprising frictionally engaging contacts (e.g. brush-like contacts), such as electromechanical brushes used in electrical motors or any other common form of interference connector (e.g. canted springs, conductive mesh, deformable fingers, and the like). Contacts 292' are each electrically attached to one or more electrical components of implantable device 200, such as via electrical wires as shown. Attachment port 290 and contacts 292' are configured to slidingly receive and frictionally engage proximal portion 268 of lead 265, and to provide an electrical connection between contacts 262 and one or more electrical-based internal components of implantable device 200. Attachment port 290 can include one or more gaskets, gasket 296 shown, to provide a seal around the entry point of lead 265 into attachment port 290. Gasket 296 can also include one or more gaskets positioned between each of the adjacent contacts 292', such as to minimize fluid conduction pathways between contacts 292'.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 7A:
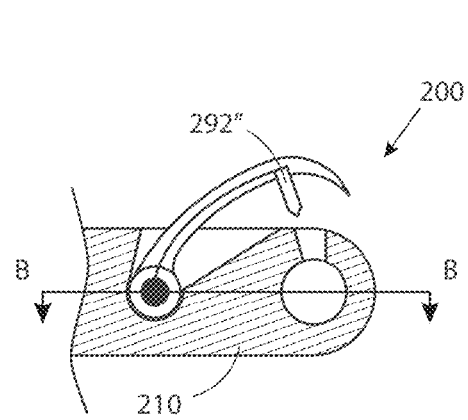
FIGS. 7A-C are a side sectional view, a sectional view, and a perspective view, respectively, of an attachment port of an implantable device consistent with the present inventive concepts.
Figure 7B:
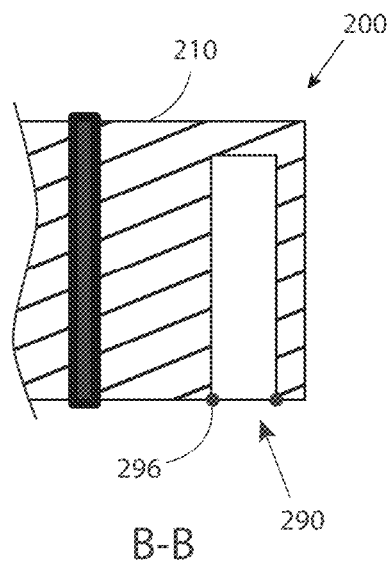
Figure 7C:
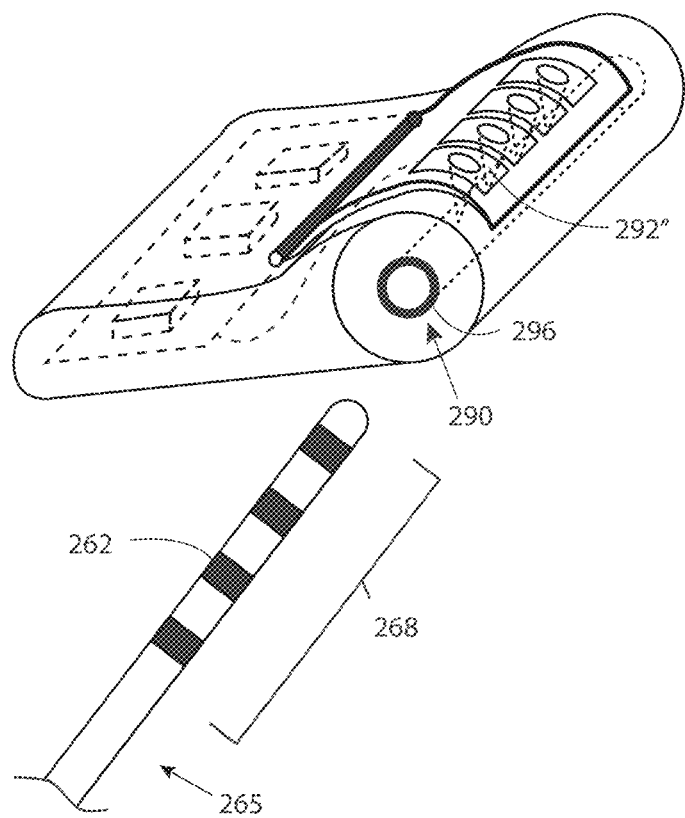

Referring now to FIGS. 7A-C, a side sectional view, a sectional view, and a perspective view, respectively, of an attachment port of an implantable device are illustrated, consistent with the present inventive concepts. Apparatus 10 comprises implantable device 200, lead 265, and other components of similar construction and arrangement to those described hereabove in reference to FIG. 1. Implantable device 200 of FIGS. 7A-C comprises attachment port 290 which extends within implantable device 200, such as to receive the proximal portion 268 of lead 265 including all contacts 262. Attachment port 290 includes rotating contacts 292", each (four shown) comprising a hinge, an extension arm, and a conductive pin. The conductive pin of contacts 292" are each electrically attached to one or more electrical components of implantable device 200, such as via electrical wires as shown. Attachment port 290 is configured to slidingly receive proximal portion 268 of lead 265, after which contacts 292" can be rotated such that its pins frictionally engage and electrically connect to contacts 262 of lead 265, providing an electrical connection between contacts 262 and one or more electrical-based internal components of implantable device 200. The pins can pass through preformed holes (e.g. vias) and/or puncture through housing 210 in order to make the connection. Attachment port 290 can include one or more gaskets, gasket 296 shown, to provide a seal around the entry point of lead 265 into attachment port 290. Gasket 296 can also include one or more gaskets positioned between each of the contacts 292" to minimize fluid conduction pathways between contacts 292".

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 8A:
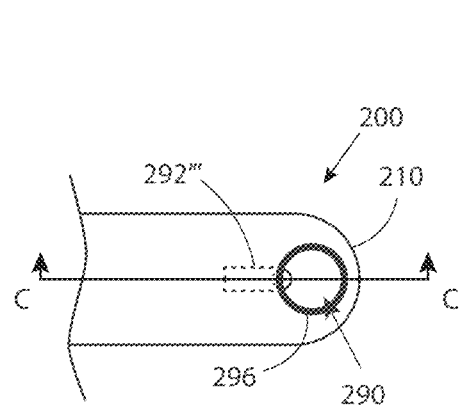
FIGS. 8A-C are a side view, a sectional view, and a perspective view, respectively, of an attachment port of an implantable device, consistent with the present inventive concepts.
Figure 8B:
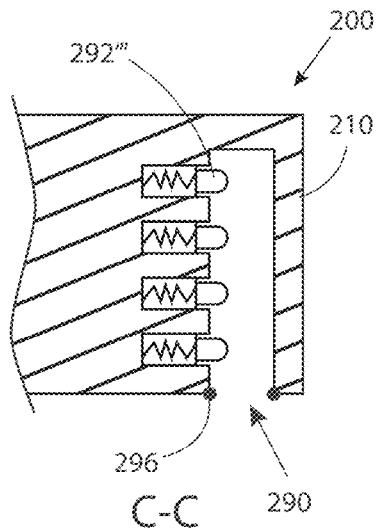
Figure 8C:
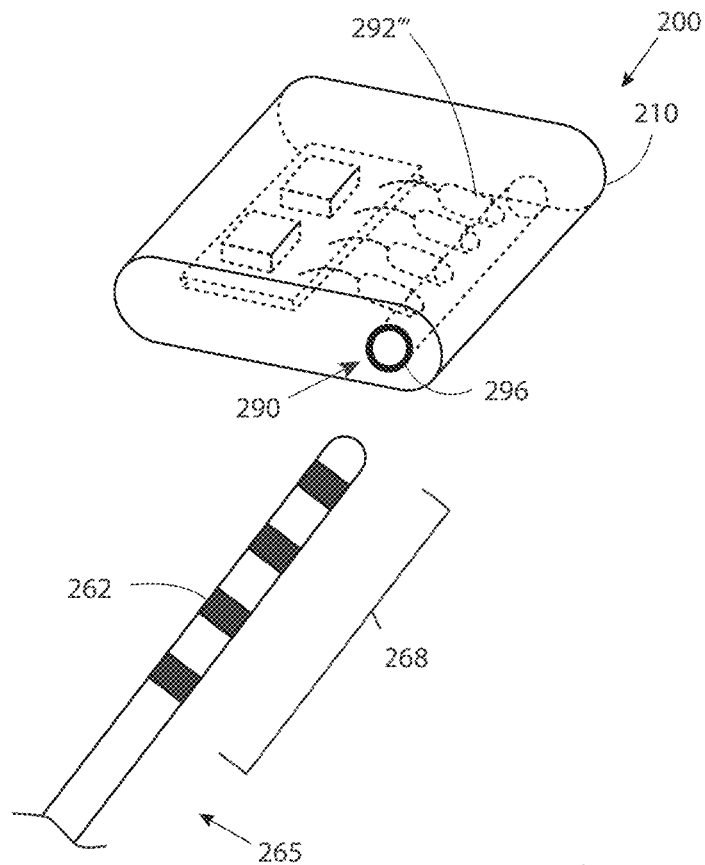

Referring now to FIGS. 8A-C, a side view, a sectional view, and a perspective view, respectively, of an attachment port of an implantable device are illustrated, consistent with the present inventive concepts. Apparatus 10 comprises implantable device 200, lead 265, and other components of similar construction and arrangement to those described hereabove in reference to FIG. 1. Implantable device 200 of FIGS. 8A-C comprises attachment port 290 which extends within implantable device 200, such as to receive the proximal portion 268 of lead 265 including all contacts 262. Attachment port 290 includes spring-loaded contacts 292''', each (four shown) comprising a conductive pin and a spring-like component configured to bias the pin in an extended position, as shown in FIG. 8B. The conductive pin of contacts 292''' are each electrically attached to one or more electrical components of implantable device 200, such as via electrical wires as shown.

Attachment port 290 and contacts 292''' are configured to slidingly receive proximal portion 268 of lead 265. Once fully inserted, contacts 292''' frictionally engage and electrically connect to contacts 262 of lead 265, providing an electrical connection between contacts 262 and one or more electrical-based internal components of implantable device 200. Attachment port 290 can include one or more gaskets, gasket 296 shown, to provide a seal around the entry point of lead 265 into attachment port 290. Gasket 296 can also include one or more gaskets positioned between each of the contacts 292''' to minimize fluid conduction pathways between contacts 292'''.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 9A:
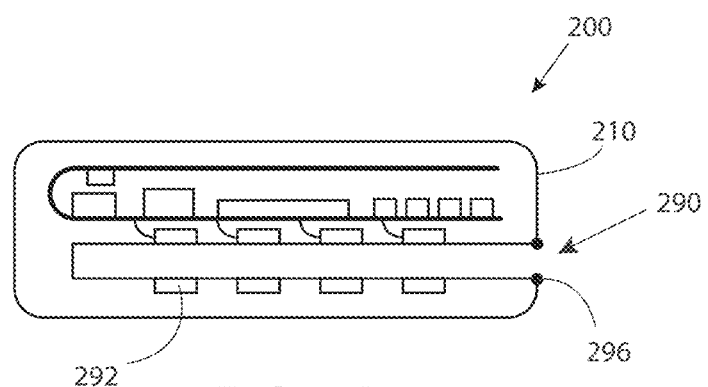
FIG. 9A-B are a side sectional view, and an end view, respectively, of an implantable device, consistent with the present inventive concepts.
Figure 9B:
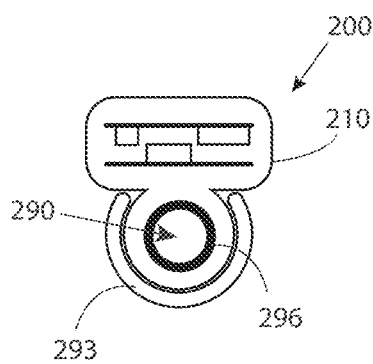

Referring now to FIGS. 9A-B, a side sectional view, and an end view, respectively, of an implantable device are illustrated, consistent with the present inventive concepts. Implantable device 200, lead 265, and other components of apparatus 10 can be of similar construction and arrangement to those described hereabove in reference to FIG. 1. Implantable device 200 of FIGS. 9 A-B comprises attachment port 290 which extends within implantable device 200, such as to receive the proximal portion of a lead 265 including all contacts 262 (not shown). Attachment port 290 includes spring-loaded contacts 292, each (four shown) comprising a conductive segment electrically attached to one or more electrical components of implantable device 200, such as via electrical wires as shown.

Attachment port 290 and contacts 292 are configured to slidingly receive proximal portion 268 of lead 265. Once fully inserted, contacts 292 frictionally engage and electrically connect to contacts 262 of lead 265, providing an electrical connection between contacts 262 and one or more electrical-based internal components of implantable device 200. Contacts 262 can be of similar construction and arrangement to any of contacts 292', 292" and/or 292''' described herein. Attachment port 290 further comprises compression element 293 which can be configured to compress (e.g. radially compress) attachment port 290 onto lead 265, such as to provide a seal at the location in which lead 265 enters attachment port 290. Alternatively or additionally, compression element 293 can be configured to create and/or improve the connection between contacts 262 and contacts 292. In some embodiments, attachment port 290 includes one or more gaskets, gasket 296 shown, to provide and/or enhance the seal between lead 265 and attachment port 290. Gasket 296 can also include one or more gaskets positioned between each of the contacts 292 to minimize fluid conduction pathways between contacts 292.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Figure 10A:
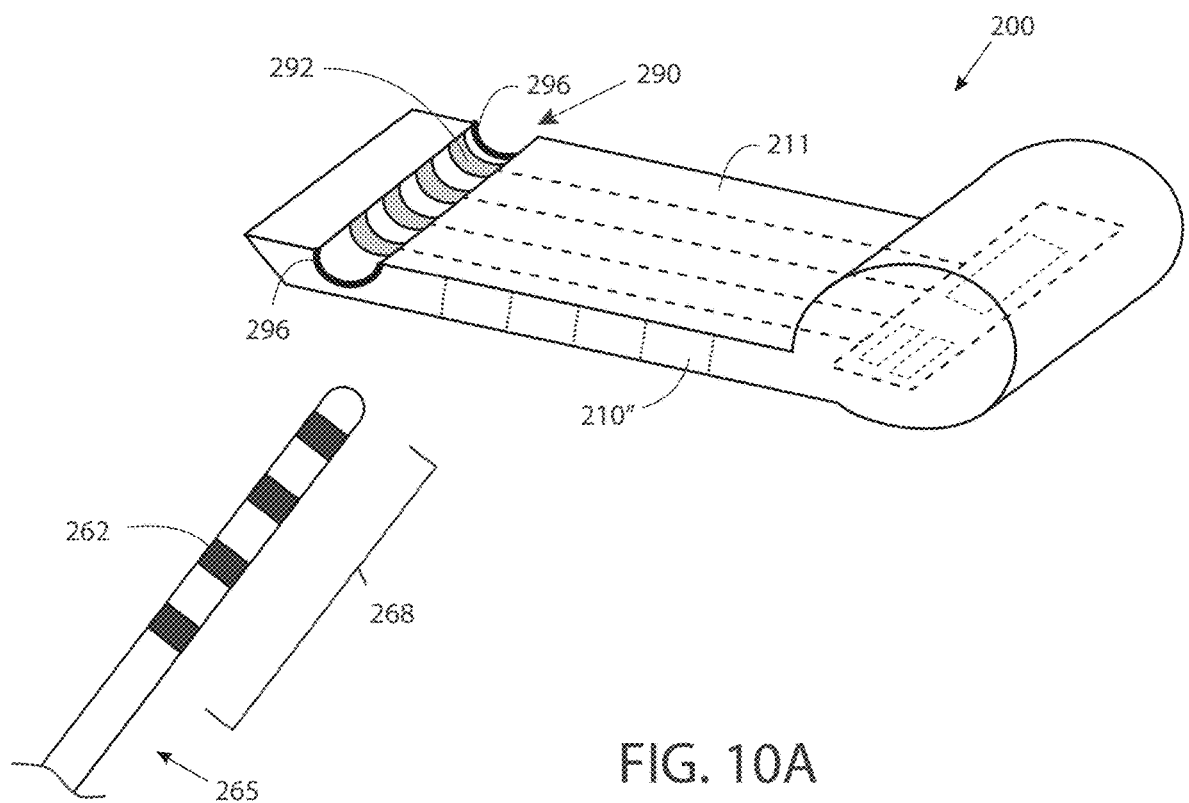
FIG. 10A-B are perspective views of an implantable device prior to and after attachment to a lead, respectively, the implantable device comprising a rollable construction for surrounding the lead, consistent with the present inventive concepts.
Figure 10B:
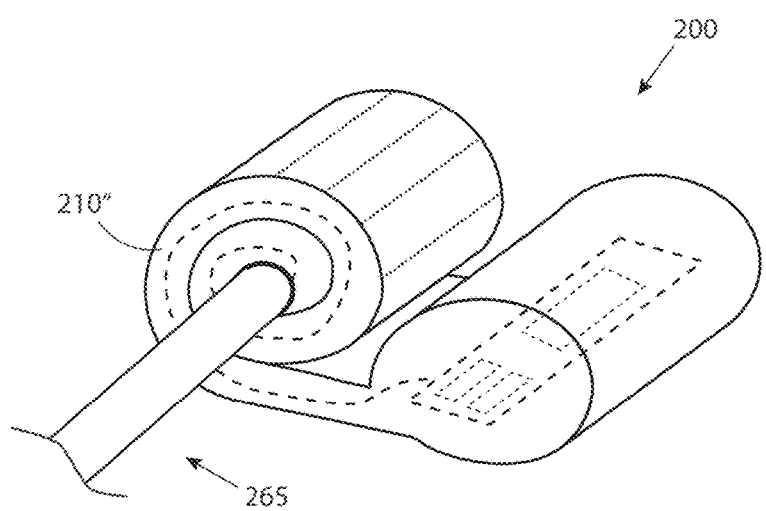

Referring now to FIGS. 10A-B, perspective views of an implantable device prior to and after attachment to a lead, respectively, are illustrated, the implantable device comprising a rollable construction for surrounding the lead, consistent with the present inventive concepts. Implantable device 200 and lead 265 can be of similar construction and arrangement to those described hereabove in reference to FIG. 1. Implantable device 200 of FIGS. 10A-B comprises a flexible housing, housing 210", which is configured to be rolled such that housing 210" circumferentially surrounds lead 265 as shown in FIG. 10B, where housing 210" circumferentially surrounds lead 265. Housing 210" can comprise a flexible material and/or it can comprise multiple hinged sections configured to be pivoted (i.e. flexed) at each hinge section.

Implantable device 200 comprises contacts 292 (four shown) which are configured to operatively connect to corresponding contacts 262 (four shown) of lead 265, such as to provide an electrical connection between contacts 262 and one or more electrical-based internal components of implantable device 200. Contacts 262 can be of similar construction and arrangement to any of contacts 292', 292" and/or 292''' described herein. In some embodiments, housing 210" comprises an adhesive portion, portion 211 shown on the top side of housing 210", which can be configured to maintain housing 210" about lead 265 (e.g. prevent unrolling of housing 210").

In some embodiments, attachment port 290 includes one or more gaskets, such as gasket 296 shown, to provide and/or enhance the seal between lead 265 and attachment port 290. Gasket 296 can also include one or more gaskets positioned between each of the contacts 292 to minimize fluid conduction pathways between contacts 292.

In some embodiments, lead 265 is configured to be detached from implantable device 200 and subsequently operatively attached to implantable device 800 (e.g. in a second clinical procedure in which implantable device 800 is implanted). In some embodiments, lead 265 comprises a removable distal portion configured to subsequently attach to second implantable stimulator 800, as described hereabove in reference to FIG. 1C.

Referring now to FIGS. 11A-D, perspective views of various embodiments of a distal portion of a stimulation lead are illustrated, consistent with the present inventive concepts. Lead 265 can comprise chronically implantable lead, such as a lead configured to provide long term therapy (e.g. a lead implanted for at least one week, at least one month, and/or at least 6 months), and/or a test lead configured to be inserted in the patient for an acute period of time (e.g. to provide temporary stimulation for less than one hour, less than one day, and/or less than one week). For example, lead 265 can comprise a needle-like construction, with the distal portion 269 constructed and arrange to be temporarily inserted proximate one or more nerves to be stimulated by stimulation apparatus 10, as described herein. In some embodiments, after implantation and/or while temporarily inserted, lead 265 can be used in a trialing procedure as described herebelow in reference to FIG. 13.

As described herebelow, lead 265 can comprise various configurations, such as varied constructions of its distal portion, such as distal portions 2691-2694 shown. The distal portions can each include one or more stimulation elements 260 configured to deliver energy to target tissue of a patient (e.g. one or more electrodes configured to deliver monopolar or bipolar electrical energy to tissue). Each lead 265 can comprise a proximal portion, such as proximal portions 2681-2683 as described herebelow in reference to FIGS. 12A-C, or other proximal portion 268 described herein. The proximal portion of each lead 265 can include one or more contacts 262 configured to operably connect to a stimulation device (e.g. to provide an electrical connection between stimulation device 200/800 and one or more stimulation elements 260 such that energy provided by the stimulation device can be delivered by the stimulation elements 260).

Figure 11A:
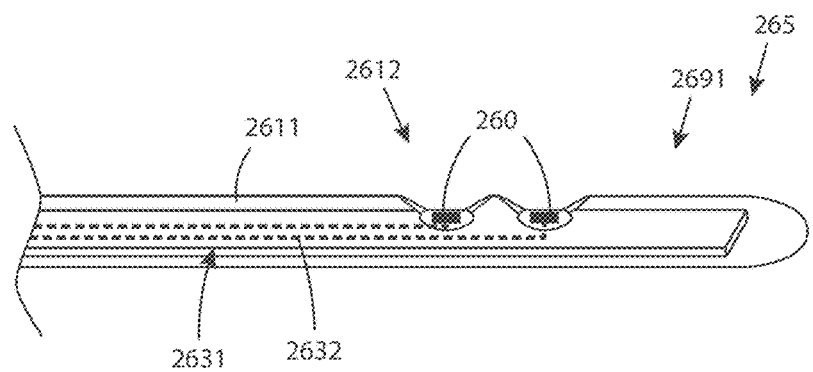
FIGS. 11A-D are perspective views of various embodiments of a distal portion of a stimulation lead, consistent with the present inventive concepts.

As shown in FIG. 11A, distal portion 2691 can comprise a flex circuit 2631 and a covering surrounding flex circuit 2631, overmold 2611. In some embodiments, one or more portions of overmold 2611 are removed (e.g. via a manufacturing process) to create one or more recesses 2612 to expose stimulation elements 260 configured to deliver energy to target tissue. Flex circuit 2631 can comprise one or more traces 2632 extending from the proximal portion of lead 265 to distal portion 2691 of lead 265. Traces 2632 can operably connect stimulation elements 260 and contacts 262 (e.g. to provide an electrical connection between stimulation elements 260 and contacts 262).

Figure 11B:
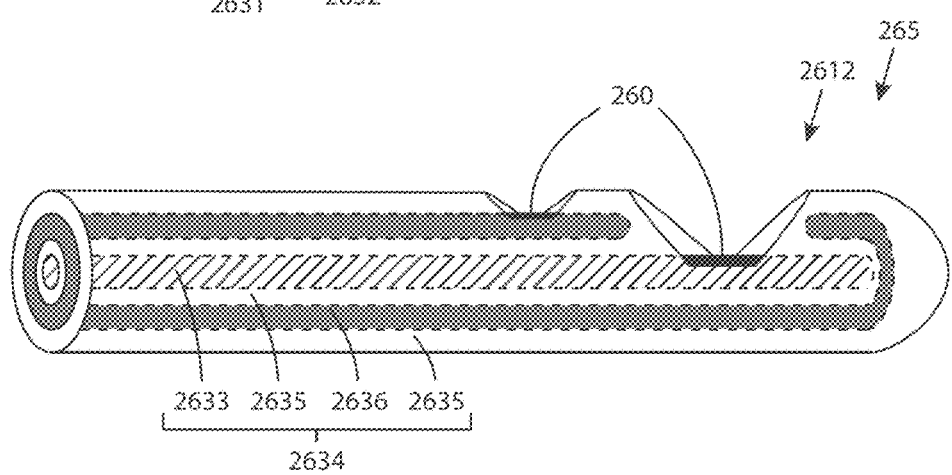

As shown in FIG. 11B, distal portion 2692 can comprise a conductive rod 2633 (e.g. a needle) with layer stack 2634 applied thereon (e.g. multiple layers applied to rod 2633). Layer stack 2634 can comprise alternating layers of an insulator 2635 and a conductor 2636, with the outer most layer comprising insulator 2635. The layers of insulator 2635 and conductor 2636 can be applied using one or more of the following deposition processes: sputtering; evaporation; dipping; plating; spraying; and chemical vapor deposition (CVD). In some embodiments, one or more portions of layer stack 2634 are removed (e.g. via a manufacturing process, such as laser ablation, wet etch, lift-off, etc.) to create one or more recesses 2612 to expose one or more portions of conductor 2636 and/or conductive rod 2633. The exposed portions of conductor 2633 and/or conductive rod 2636 can comprise metalized contacts, stimulation elements 260 that are configured to deliver energy to target tissue. Conductive rod 2633 and/or conductor 2636 can operably connect to contacts 262 (e.g. to provide an electrical connection between stimulation elements 260 and contacts 262).

Figure 11C:
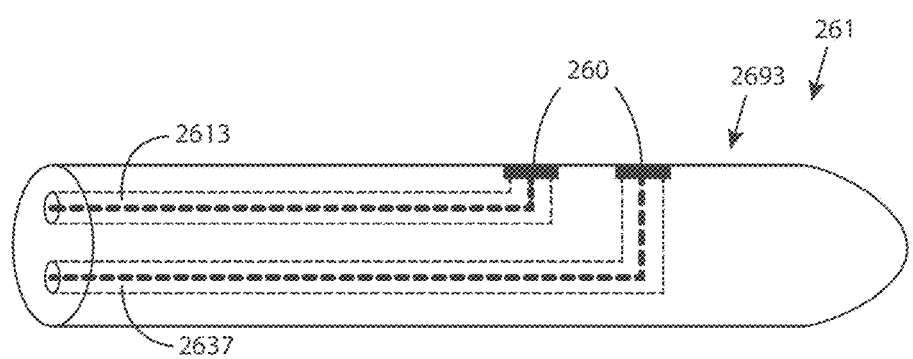

As shown in FIG. 11C, distal portion 2693 can comprise one or more lumens 2613 extending from the proximal portion of lead 265 to distal portion 2693 of lead 265. Lumens 2613 can surround one or more wires 2637 that operably connect stimulation elements 260 and contacts 262 (e.g. to provide an electrical connection between stimulation elements 260 and contacts 262).

Figure 11D:
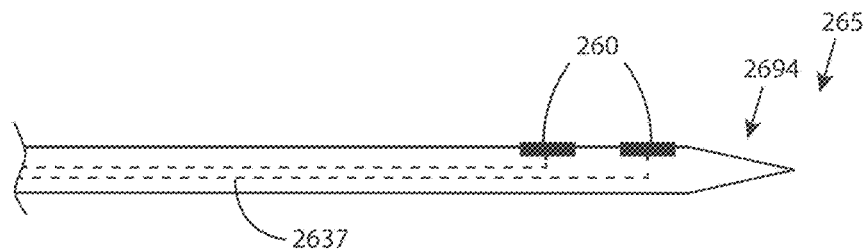

As shown in FIG. 11D, distal portion 2694 can comprise a needle-like construction, including (e.g. surrounding) one or more wires 2637 extending from proximal portion 268 to distal portion 2694 of lead 265. Wires 2637 can operably connect stimulation elements 260 and contacts 262 (e.g. to provide an electrical connection between stimulation elements 260 and contacts 262).

Figure 12A:
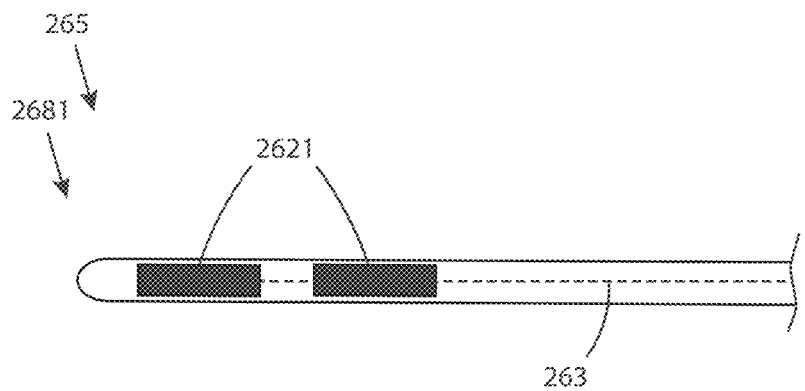
FIGS. 12A-C are side views of various embodiments of a proximal portion of a stimulation lead, consistent with the present inventive concepts.
Figure 12B:
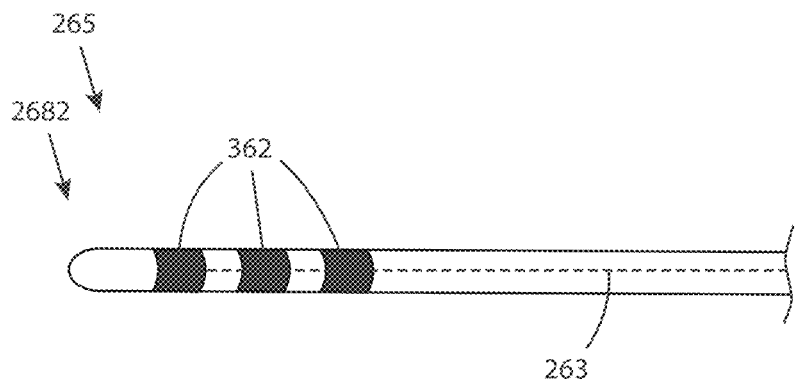
Figure 12C:
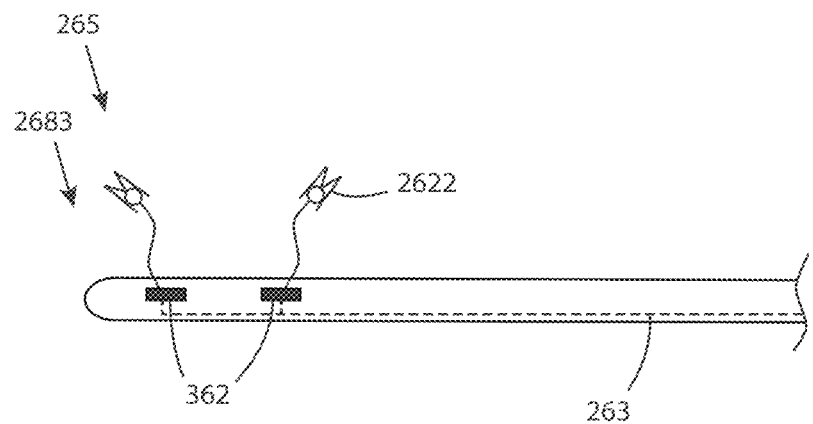

Referring now to FIGS. 12A-C, side views of various embodiments of a proximal portion of a stimulation lead are illustrated, consistent with the present inventive concepts. Lead 265 can comprise a chronically implantable lead, as described herein, and/or a test lead configured to be inserted in the patient for an acute period of time, as described herein. For example, lead 265 can comprise a needle-like construction, with its distal portion 269 constructed and arranged to be temporarily inserted proximate one or more nerves to be stimulated by stimulation apparatus 10, as described herein. In some embodiments, after implantation and/or while temporarily inserted, lead 265 can be used in a trialing procedure as described herebelow in reference to FIG. 13.

As described herebelow, lead 265 can comprise various configurations, such as varied constructions of its proximal portion, such as proximal portions 2681-2683 as shown. The proximal portions can each include one or more contacts 262 configured to operably connect to a stimulation device (e.g. to provide an electrical connection between stimulation device 200/800 and one or more stimulation elements 260 such that energy provided by the stimulation device can be delivered by the stimulation elements 260). Each lead 265 can comprise a distal portion 269, such as distal portions 2691-2694 as described hereabove in reference to FIGS. 11A-C, or other distal portions 269 described herein. Distal portion 269 can include one or more stimulation elements 260 configured to deliver energy to target tissue of a patient (e.g. one or more electrodes configured to deliver monopolar or bipolar electrical energy).

As shown in FIG. 12A, proximal portion 2681 can comprise one or more contacts 2621. Contacts 2621 can be operably attached to conduit 263. Contacts 2621 can each comprise a length of at least 0.07 inches. In some embodiments, contacts 2621 comprise a length greater than the length of contacts of commercially available stimulation leads, and/or contacts 2621 are otherwise sized such that a user can securely, repeatably, and/or reliably attach an alligator clip and/or other connection device to contact 2621 (e g minimizing the likelihood of connecting to an undesired contact of the lead).

A shown in FIG. 12B, proximal portion 2682 can comprise one or more contacts 262 operably attached to conduit 263. Proximal end 2682 can be operably insertable into a connector, such as attachment port 290 and/or 890 as described herein. Alternatively or additionally, proximal end 2682 can be operably attachable to an attachment mechanism, such as described herebelow in reference to FIGS. 15A-E.

As shown in FIG. 12C, proximal portion 2683 can comprise one or more contacts 262 that are operably attached to one or more connectors 2622. Each connector 2622 can comprise an alligator clip or other electrically-connecting element.

Figure 13:
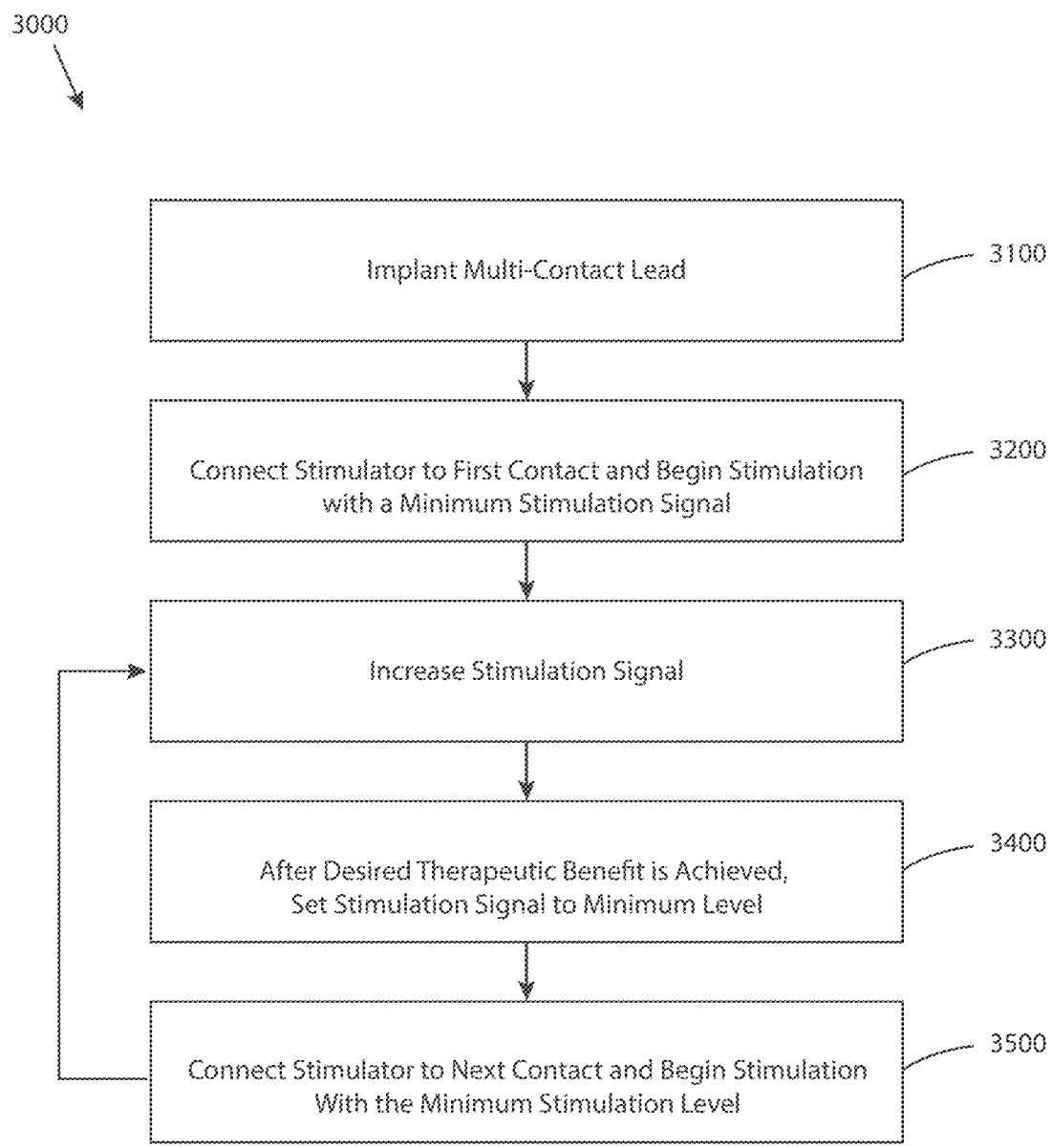
FIG. 13 is a flow chart of a method of providing stimulation during a trailing procedure, consistent with the present inventive concepts.

Referring now to FIG. 13, a flow chart of a method of providing stimulation during a trialing procedure is illustrated, consistent with the present inventive concepts. The trialing procedure comprising method 3000 of FIG. 13 can be accomplished with a stimulation device (e.g. stimulation device 200/800 described herein) and an implantable lead 265. In STEP 3100, lead 265 is implanted in the patient. In STEP 3200, a stimulation device is connected to a first contact 262 of lead 265. A trial period is initiated during which the stimulation device delivers stimulation energy with a minimum stimulation signal (e.g. a stimulation level at or close to 0). During STEP 3300, the stimulation signal is increased, such as to achieve an optimized, or at least an improved, therapeutic benefit to the patient (e.g. increased pain relief). In STEP 3400, once a desired therapeutic benefit is achieved (or a maximum stimulation level is reached with or without achieving a desired therapeutic benefit), the stimulation signal is decreased to the minimum stimulation signal. In STEP 3500, the stimulation device is disconnected from the first contact 262 and subsequently connected to a second contact 262. A trial period is initiated during which the stimulator delivers stimulation energy with the minimum stimulation signal. STEPS 3300 through 3500 can be repeated with additional contacts 262 to achieve an optimized therapeutic benefit to the patient.

After completion of STEP 3400 for the final contact 262 (e.g. each contact 262 has delivered trialing stimulation), if adequate therapy is achieved (e.g. an optimized, desired, and/or otherwise adequate therapy is achieved), long-term therapy can be implemented with implantable device 200/800 and lead 265 using the optimized stimulation signals identified in method 3000.

Referring now to FIGS. 14A-D, side views of an implantable system comprising a short-term (temporary) implantable device with an integrated lead, and a lead removal tool are illustrated, consistent with the present inventive concepts. The lead removal tool is used to remove the lead from the short-term implantable device for subsequent use with a long-term implantable device. The short-term implantable device can comprise implantable device 200, as described hereabove, such as to provide temporary stimulation therapy, as described hereabove. The long-term implantable device can comprise implantable device 800, such as to provide long-term stimulation therapy to the patient, also as described hereabove.

As shown in FIG. 14A, implantable device 200 and lead 265 are integrated (e.g. lead 265 is fixedly attached to implantable device 200, such as during a manufacturing process). Implantable device 200 can be operably attached via one or more wires 294 to one or more stimulation elements 260 of lead 265. Lead 265 comprises one or more contacts 262 which are similarly connected to stimulation elements 260. Contacts 262 can be covered by an insulating material, insulator 66, which can comprise a passivation layer applied to contacts 262 and/or an insulating sleeve. In some embodiments, implantable device 200 and lead 265 are operably attached via connector 66. Insulator 66 can extend from the most proximal contact 262 to the most distal contact 262. Insulator 66 can be configured to be removed, such as via a peeling process, to expose contacts 262, as described herebelow.

As shown in FIG. 14B, a tool 62 can slidingly receive implantable device 200 through an opening 63. In some embodiments, opening 63 can include one or more projections 64. Projections 64 can be configured to engage lead 265 at a pre-determined location, as indicated by a marker 68 on proximal portion 268 of lead 265. In some embodiments, marker 68 is positioned at a weakened portion of lead 265.

As shown in FIG. 14C, in response to an external force, projections 64 can travel inward and frictionally engage lead 265 at marker 68, to separate lead 265 from implantable device 200 (e.g. to sever and/or cause a break in lead 265). In some embodiments, insulator 66 is removed to expose contacts 262. Implantable device 200 (e.g. including a portion of wires 294), can be removed and replaced with implantable device 800, as shown in FIG. 14D. Implantable device 800 can slidingly receive the proximal portion (e.g. the remaining proximal portion) of lead 265, including contacts 262 (e.g. lead proximal portion 268). Contacts 262 each align with and operably engage associated contacts 892 of device 800, similar to as described hereabove in reference to FIG. 1.

Referring now to FIGS. 15A-E, a perspective view of a stimulator and a lead attachment assembly, and various close-up views of an attachment mechanism of the attachment assembly, are illustrated, consistent with the present inventive concepts. Attachment assembly 650 can comprise an attachment mechanism 655, and can be used to attach a lead 265 to a stimulation device 600. Stimulation device 600 can be configured to provide stimulation energy to lead 265 (similar to implantable devices 200/800), and it can include a user interface (e.g. similar to devices 500/550). In some embodiments, stimulation device 600 receives commands (e.g. wirelessly receives commands) from devices 500/550.

Figure 15A:
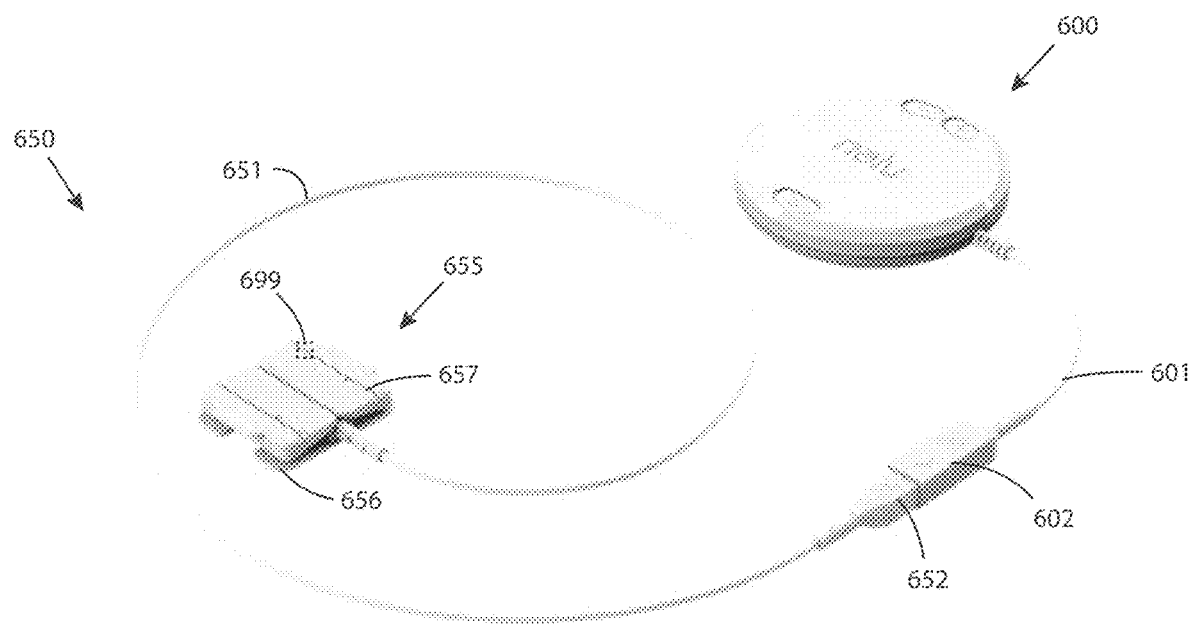
FIGS. 15A-E a perspective view of a stimulator and a lead attachment assembly, and various close-up views of an attachment mechanism of the attachment assembly, consistent with the present inventive concepts.

As shown in FIG. 15A, stimulator device 600 can include a conduit 601 (e.g. a conduit including one or more wires) with a distal end connector, connector 602. Attachment assembly 650 can include a conduit 651 with a proximal end connector, connector 652. In some embodiments, connectors 602,652 comprise pig-tail connectors configured to operably connect stimulation device 600 and attachment assembly 650. Attachment assembly 650 can comprise an attachment mechanism 655 with a base portion, base 656, and one or more hinged portions, clip 657.

Base 656 can include one or more contacts 659 operably connected to conduit 651 (e.g. to provide an electrical connection between wires of conduit 651 and contacts 659). Base 656 can slidingly receive and/or rotatably engage a portion of clip 657, such that attachment mechanism 655 can transition from an open configuration (as shown in FIGS. 15D and E) to a closed configuration (as shown in FIGS. 15B and C).

Figure 15B:
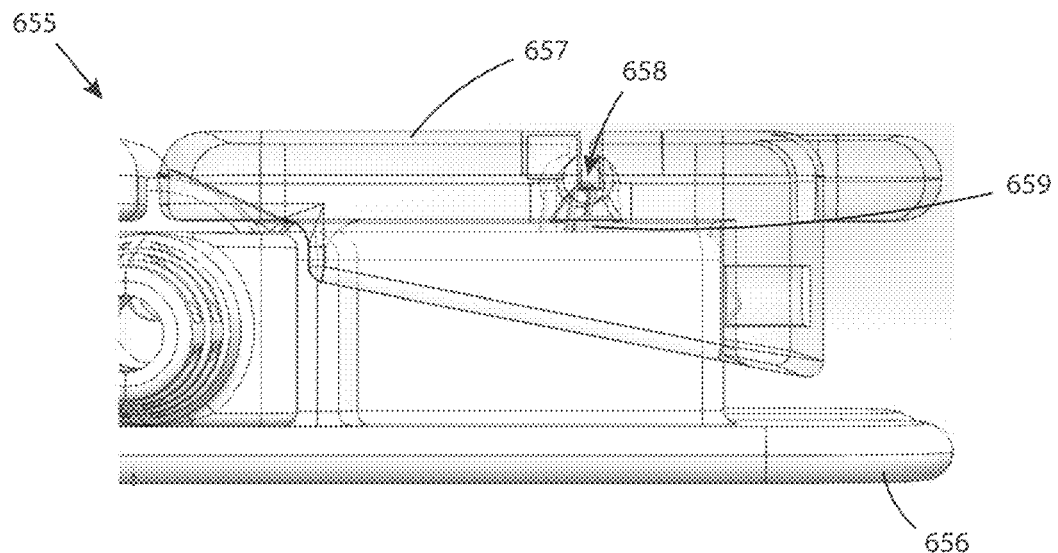

As shown in FIG. 15B, clip 657 can comprise a first recess 658 configured to slidingly receive a portion of lead 265, including contacts 262. In the closed configuration, contacts 659 can extend into recess 658 and operably connect (e.g. at least electrically connect) to contacts 262 of an inserted lead 265 (e.g. to provide at least an electrical connection between contacts 262 and 659). For example, lead 265 can be inserted into recess 658 when attachment mechanism is in an open configuration, and clip 657 can subsequently be "closed", locking lead 265 within recess 658, allowing contacts 262 and 659 to operably engage.

Figure 15C:
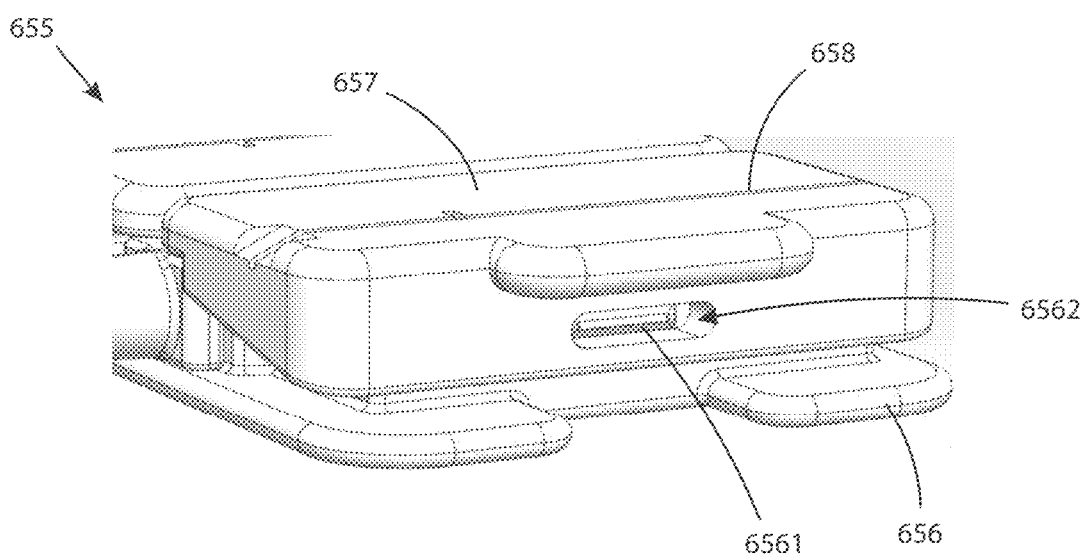
Figure 15D:
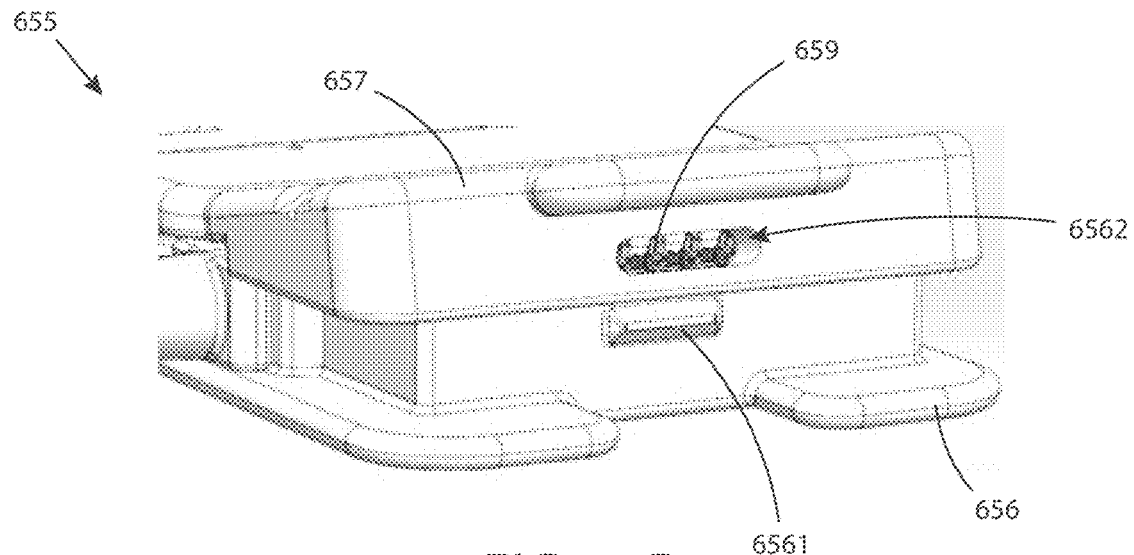

As shown in FIGS. 15C and D, attachment mechanism 655 can transition between an open configuration and a closed configuration (the open configuration shown in FIG. 15D). Base 656 and clip 657 can be configured to interlock (e.g. releasably interlock) in the closed configuration, thereby securing a portion lead 265 within attachment mechanism 655. Base 656 can include a projection 6561 configured to frictionally engage a second recess 6562 of clip 657. In some embodiments, attachment mechanism transitions from the open configuration to the closed configuration when clip 657 is depressed by a user (e.g. projection 6561 engages recess 6562). In other embodiments, attachment mechanism 655 transitions from the closed configuration to the open configuration when clip 657 is elevated by a user (e.g. projection 6561 disengages from recess 6562 when clip 657 is lifted away from base 656).

Figure 15E:
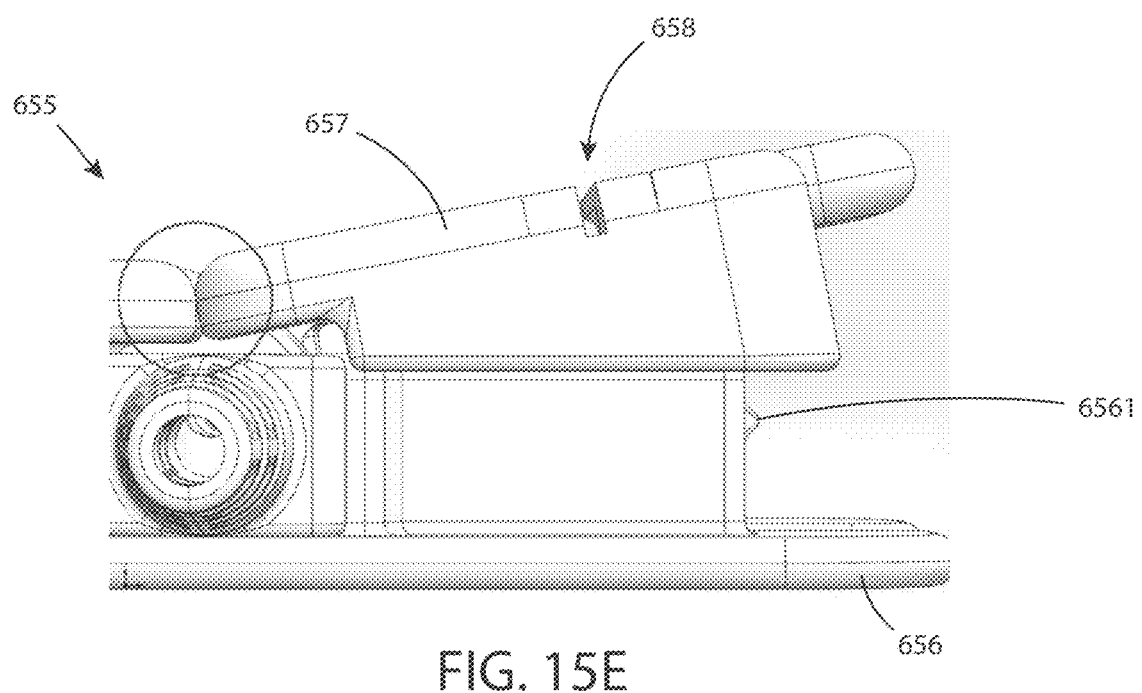

As shown in FIG. 15E, clip 657 can be configured to abut another portion of attachment mechanism 655, such as to limit the elevation of clip 657 relative to base 656. In some embodiments, attachment assembly 650 can comprise a functional element 699. Functional element 699 can comprise a sensor, configured to detect a proper (or improper) connection of a lead 265 to attachment mechanism 655 (e.g. via an impedance measurement). Additionally or alternatively, functional element 699 can comprise a transducer, such as a speaker. For example, functional element can be configured to alert the user via an audible alarm if lead 265 is dislodged from attachment mechanism 655. In some embodiments, stimulator 600 comprises functional element 699.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A method of applying stimulation therapy to a patient, the method comprising:
   implanting at least one lead under the skin of the patient, the at least one implanted lead comprising at least one stimulation element configured to deliver stimulation energy to tissue of the patient;
   implanting a first implantable device in a patient and attaching the first implantable device to the at least one implanted lead, wherein the first implantable device is configured to deliver a first stimulation energy to the at least one stimulation element of the at least one implanted lead for a first time period;
   detaching the at least one implanted lead from the first implantable device after the first time period; and
   implanting a second implantable device and attaching the second implantable device to the at least one implanted lead, wherein the second implantable device is configured to deliver a second stimulation energy to the at least one stimulation element of the at least one implanted lead for a second time period, subsequent to the first time period, and wherein the second time period is a longer period of time than the first time period.

2. The method according to claim 1, wherein the first period is less than or equal to 3 months.

3. The method according to claim 1, wherein the second time period is greater than or equal to 3 months.

4. The method according to claim 1, wherein attaching the first implantable device to the at least one implanted lead comprises operably connecting a first implantable connector of the first implantable device to the at least one implanted lead, wherein attaching the second implantable device to the at least one implanted lead comprises operably connecting a second implantable connector of the second implantable device to the at least one implanted lead, and wherein the first implantable connector and the second implantable connector comprise dissimilar construction and arrangement.

5. The method according to claim 4, wherein the first implantable connector is configured to provide a contamination-preventing seal for a limited time period, and wherein the second implantable connector is configured to provide a contamination-preventing seal for an extended time period.

6. The method according to claim 5, wherein the limited time period comprises less than 3 months, and wherein the extended time period comprises more than 3 months.

7. The method according to claim 1, wherein the at least one implanted lead is integrated into the first implantable device.

8. The method according to claim 7, further comprising detaching the at least one implanted lead from the first implantable device.

9. The method according to claim 8, wherein detaching the at least one implanted lead from the first implantable device comprises severing and/or breaking the at least one implanted lead.

10. The method according to claim 9, further comprising attaching the at least one implanted lead to the second implantable device after detaching the at least one implanted lead from the first implantable device.

11. The method according to claim 1, wherein the at least one implanted lead comprises a proximal portion and a distal portion, and further comprising detaching the distal portion from the proximal portion.

12. The method according to claim 11, wherein attaching the second implantable device to the at least one implanted lead comprises operably connecting a second implantable connector of the second implantable device to the at least one implanted lead, and wherein the method further comprises attaching the detachable distal portion to the second implantable connector.

13. The method according to claim 11, wherein the proximal portion is pre-attached to the first implantable device.

14. The method according to claim 1, wherein the first implantable device receives power and data from an external system, and wherein the second implantable device receives data from the external system.

15. The method according to claim 14, wherein the second implantable device does not receive power from the external system.

16. The method according to claim 14, wherein the external system is configured to transmit transmission signals and comprises a first external device comprising:
at least one external antenna configured to transmit the transmission signals to one or more of the first or second implantable devices;
an external transmitter configured to drive the at least one external antenna;
an external power supply configured to provide power to at least the external transmitter; and
an external controller configured to control the external transmitter.

17. The method according to claim 1, wherein the first implantable device comprises an implantable energy storage assembly.

18. The method according to claim 17, wherein the implantable energy storage assembly of the second implantable device has a greater energy storage capacity than the implantable energy storage assembly of the first implantable device.

19. The method according to claim 18, wherein the implantable energy storage assembly of the second implantable device has at least 10 times the energy storage capacity as the energy storage capacity of the implantable energy storage assembly of the first implantable device.

20. The method according to claim 17, wherein the first implantable device energy storage assembly comprises an energy storage capacity of no more than 40 Joules.

21. The method according to claim 20, wherein the second implantable device energy storage assembly comprises an energy storage capacity of at least 60 Joules.

22. The method according to claim 1, wherein the first implantable device is configured to deliver stimulation energy to the at least one stimulation element of the implanted lead and comprises:
at least one first implantable antenna configured to receive a transmission signal from an external system, the transmission signals comprising power and data;
a first implantable receiver configured to receive the transmission signals from the at least one first implantable antenna;
a first implantable controller configured to deliver energy to the at least one stimulation element of the implanted lead, the delivered energy provided by the transmission signals received from the external device; and
a first implantable housing surrounding at least the first implantable controller and the first implantable receiver.

23. The method according to claim 1, wherein the second implantable device is configured to deliver stimulation energy to the at least one stimulation element of the implanted lead and comprises:
at least one second implantable antenna configured to receive a transmission signal from an external system, the transmission signals comprising data;
a second implantable receiver configured to receive the transmission signals from the at least one second implantable antenna;
an implantable energy storage assembly comprising a battery and/or a capacitor;
a second implantable controller configured to deliver energy to the at least one stimulation element of the implantable lead, the delivered energy provided by the implantable energy storage assembly; and
a second implantable housing surrounding at least the second implantable controller and the second implantable receiver.

24. A method of applying stimulation therapy to a patient, the method comprising:
attaching a first implantable device implanted in a patient to at least one lead implanted in the patient;
delivering a first stimulation energy to at least one stimulation element of the at least one implanted lead with the first implantable device implanted in the patient and attached to the at least one implanted lead, wherein the first stimulation energy is delivered to the at least one stimulation element for a first time period;
detaching the at least one implanted lead from the first implantable device after the first time period;
attaching a second implantable device implanted in the patient to the at least one implanted lead;
delivering a second stimulation energy to the at least one stimulation element of the at least one implanted lead with the second implantable device implanted in the patient and attached to the at least one implanted lead, wherein the second stimulation energy is delivered to the at least one stimulation element for a second time period, and wherein the second time period is a longer period of time than the first time period.

25. The method according to claim 24, wherein the first period is less than or equal to 3 months.

26. The method according to claim 24, wherein the second time period is greater than or equal to 3 months.

27. The method according to claim 24, wherein attaching the first implantable device to the at least one implanted lead comprises operably connecting a first implantable connector of the first implantable device to the at least one implanted lead, wherein attaching the second implantable device to the at least one implanted lead comprises operably connecting a second implantable connector of the second implantable device to the at least one implanted lead, and wherein the first implantable connector and the second implantable connector comprise dissimilar construction and arrangement.

28. The method according to claim 27, wherein the first implantable connector is configured to provide a contamination-preventing seal for a limited time period, and wherein the second implantable connector is configured to provide a contamination-preventing seal for an extended time period.

29. The method according to claim 28, wherein the limited time period comprises less than 3 months, and wherein the extended time period comprises more than 3 months.

30. The method according to claim 24, wherein the at least one implanted lead is integrated into the first implantable device.

31. The method according to claim 24, wherein detaching the at least one implanted lead from the first implantable device comprises severing and/or breaking the at least one implanted lead.

32. The method according to claim 24, wherein the at least one implanted lead comprises a proximal portion and a distal portion, and further comprising detaching the distal portion from the proximal portion.

33. The method according to claim 32, wherein attaching the second implantable device to the at least one implanted lead comprises operably connecting a second implantable connector of the second implantable device to the at least one implanted lead, and wherein the method further comprises attaching the detachable distal portion to the second implantable connector.

34. The method according to claim 32, wherein the proximal portion is pre-attached to the first implantable device.

35. The method according to claim 24, further comprising receiving power and data from an external system with the first implantable device and receiving data from the external system with the second implantable device.

36. The method according to claim 35, wherein the second implantable device does not receive power from the external system.

37. The method according to claim 35, wherein the external system is configured to transmit transmission signals and comprises a first external device comprising:
at least one external antenna configured to transmit the transmission signals to one or more of the first or second implantable devices;
an external transmitter configured to drive the at least one external antenna;
an external power supply configured to provide power to at least the external transmitter; and
an external controller configured to control the external transmitter.

38. The method according to claim 37, wherein the first implantable device comprises an implantable energy storage assembly.

39. The method according to claim 38, wherein the implantable energy storage assembly of the second implantable device has a greater energy storage capacity than the implantable energy storage assembly of the first implantable device.

40. The method according to claim 39, wherein the implantable energy storage assembly of the second implantable device has at least 10 times the energy storage capacity as the energy storage capacity of the implantable energy storage assembly of the first implantable device.

41. The method according to claim 38, wherein the first implantable device energy storage assembly comprises an energy storage capacity of no more than 40 Joules.

42. The method according to claim 41, wherein the second implantable device energy storage assembly comprises an energy storage capacity of at least 60 Joules.

43. The method according to claim 24, wherein the first implantable device is configured to deliver stimulation energy to the at least one stimulation element of the implanted lead and comprises:
at least one first implantable antenna configured to receive a transmission signal from an external system, the transmission signals comprising power and data;
a first implantable receiver configured to receive the transmission signals from the at least one first implantable antenna;
a first implantable controller configured to deliver energy to the at least one stimulation element of the implanted lead, the delivered energy provided by the transmission signals received from the external device; and
a first implantable housing surrounding at least the first implantable controller and the first implantable receiver.

44. The method according to claim 24, wherein the second implantable device is configured to deliver stimulation energy to the at least one stimulation element of the implanted lead and comprises:
at least one second implantable antenna configured to receive a transmission signal from an external system, the transmission signals comprising data;
a second implantable receiver configured to receive the transmission signals from the at least one second implantable antenna;
an implantable energy storage assembly comprising a battery and/or a capacitor;
a second implantable controller configured to deliver energy to the at least one stimulation element of the implantable lead, the delivered energy provided by the implantable energy storage assembly; and
a second implantable housing surrounding at least the second implantable controller and the second implantable receiver.

* * * * *